(12) United States Patent
Meves et al.

(10) Patent No.: US 11,851,710 B2
(45) Date of Patent: Dec. 26, 2023

(54) METHODS AND MATERIALS FOR IDENTIFYING METASTATIC MALIGNANT SKIN LESIONS AND TREATING SKIN CANCER

(71) Applicant: Mayo Foundation for Medical Education and Research, Rochester, MN (US)

(72) Inventors: Alexander Meves, Rochester, MN (US); Ekaterina M. Nikolova, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 963 days.

(21) Appl. No.: 16/577,568

(22) Filed: Sep. 20, 2019

(65) Prior Publication Data

US 2020/0291480 A1    Sep. 17, 2020

Related U.S. Application Data

(63) Continuation of application No. 15/503,973, filed as application No. PCT/US2015/045065 on Aug. 13, 2015, now abandoned.
(Continued)

(51) Int. Cl.
*C12Q 1/6886* (2018.01)
*C07K 16/30* (2006.01)

(52) U.S. Cl.
CPC ........ *C12Q 1/6886* (2013.01); *C07K 16/3053* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS 7,695,913 B2    4/2010   Cowens et al.
2004/0010045 A1   1/2004   Yi
(Continued)

FOREIGN PATENT DOCUMENTS

WO    2014/077915 A1    5/2014
WO    2016/025717 A1    2/2016
WO    2017/196944       11/2017

OTHER PUBLICATIONS (Annex 1) American Cancer Society "Treatment of Melanoma Skin Cancer, by Stage" 4 pages, accessed Nov. 19, 2020, https://www.cancer.org/cancer/melanoma-skin-cancer/treating/by-stage.html.
(Continued)

*Primary Examiner* — Olivia M. Wise
(74) *Attorney, Agent, or Firm* — TraskBritt

(57) ABSTRACT

This document provides methods and materials for identifying metastatic malignant skin lesions (e.g., malignant pigmented skin lesions). For example, methods and materials for using quantitative PCR results and correction protocols to reduce the impact of basal keratinocyte contamination on the analysis of test sample results to identify metastatic malignant skin lesions are provided. This document also provides methods and materials for treating skin cancer. For example, methods and materials for identifying a mammal (e.g., a human) having a pre-metastatic skin lesion (e.g., pre-metastatic melanoma) and treating that mammal with pentamidine (4,4'-[pentane-1,5-diylbis(oxy)] dibenzenecarboximidamide) are provided.

9 Claims, 25 Drawing Sheets

Specification includes a Sequence Listing.

Related U.S. Application Data

(60) Provisional application No. 62/142,831, filed on Apr. 3, 2015, provisional application No. 62/037,325, filed on Aug. 14, 2014.

(56) References Cited

U.S. PATENT DOCUMENTS

| | | |
|---|---|---|
| 2004/0110221 A1 | 6/2004 | Twine et al. |
| 2006/0235001 A1 | 10/2006 | Elliott et al. |
| 2007/0154889 A1 | 7/2007 | Wang |
| 2008/0274908 A1* | 11/2008 | Chang .................... G16B 40/30 506/7 |
| 2009/0125247 A1 | 5/2009 | Baker et al. |
| 2010/0028876 A1 | 2/2010 | Gordon et al. |
| 2011/0123997 A1 | 5/2011 | Kashani-Sabet et al. |
| 2011/0159496 A1 | 6/2011 | Kashani-Sabet et al. |
| 2012/0071343 A1 | 3/2012 | Ma et al. |
| 2012/0128667 A1 | 5/2012 | Chow et al. |
| 2014/0045915 A1 | 2/2014 | Skog et al. |
| 2015/0290289 A1 | 10/2015 | Sampath |
| 2016/0115555 A1 | 4/2016 | Ma et al. |
| 2016/0222457 A1 | 8/2016 | Meves et al. |
| 2017/0275700 A1 | 9/2017 | Meves et al. |

OTHER PUBLICATIONS

Sominidi-Damodara et al. . "Stromal gene expression predicts sentinel lymph node metastasis of primary cutaneous melanoma (P)" Poster presented at 15th European Association of Dermato-Oncology (EADO) Congress; Apr. 24-27, 2019.

Timar et al. "Gene signature of the metastatic potential of cutaneous melanoma: too much for too little?", Clinical & Experimental Metastasis, Official Journal of Themetastasis Research Society, Kluwer Academic Publishers, DO. vol. 27, No. 6, Feb. 24, 2010 (Feb. 24, 2010), p. 371-387, XP019815757.

Yuan et al. "The web-based multiplex PCR primer design software Ultiplex and the associated experimental workflow: up to 100-plex multiplicity" BMC Genomics (last accessed Jan. 2021) 22:835 https://doi.org/10.1186/s12864-021-08149-1.

AJCC (American Joint Committee on Cancer) AJCC Cancer Staging Manual. Technical Manual [online]. 2002 [Retrieved on Jul. 28, 2017]. Retrieved from the Internet: <URL: https://cancerstaging.org/references-tools/deskreferences/Documents/AJCC6thEdCancerStagingManualPart2.pdf>; p. 209, Summary of Changes.

Anders and Huber, "Differential expression analysis for sequence count data," Genome Biol., 11(10):R106, Epub Oct. 27, 2010.

Balch et al., "Final version of 2009 AJCC melanoma staging and classification," J Clin Oncol., 27(36):6199-6206, Epub Nov. 16, 2009.

Balch et al., "Sentinel node biopsy and standard of care for melanoma," J Am Acad Dermatol., 60(5):872-875, May 2009.

Benjamin et al., "p53 and the Pathogenesis of Skin Cancer", Toxicol Appl Pharmacol., Nov. 1, 2007;.vol. 224 No. 3, pp. 241-248 (available in PMC Nov. 1, 2008, pp. 1-13), especially abstract, p. 2, 3rd para, p. 3, 2nd para, p. 4, last para, p. 7, last para—p. 8, 1st para.

Bernard et al., "Use of a new bioassay to study pentamidine pharmacokinetics," J Infect Dis., 152(4):750-754, Oct. 1985.

Breslow, "Thickness, cross-sectional areas and depth of invasion in the prognosis of cutaneous melanoma," Ann Surg., 172(5):902-908, Nov. 1970.

Bullard et al., "Evaluation of statistical methods for normalization and differential expression in mRNA-Seq experiments," BMC Bioinformatics 11:94, Feb. 18, 2010.

Carlson et al., "Establishment, maintenance and in vitro and in vivo applications of primary human glioblastoma multiforme (GBM) xenograft models for translational biology studies and drug discovery," Curr Protoc Pharmacol., Chapter 14:Unit 14.16, Mar. 2011.

Chan et al., "Regulation of adhesion dynamics by calpain-mediated proteolysis of focal adhesion kinase (FAK)," J Biol Chem., 285(15):11418-11426, Epub Feb. 11, 2010.

ClinicalTrials.gov Identifier: NCT00729807, "Pentamidine in Treating Patients With Relapsed or Refractory Melanoma," ClinicalTrials. gov [online] 2008 [retrieved on Mar. 26, 2015]. Retrieved from the Internet: <URL: https://www.clinicaltrials.gov/ct2/show/NCT00729807?term=NCT00729807&rank= 1>, 4 pages.

Conway et al., "Gene expression profiling of paraffin-embedded primary melanoma using the DASL assay identifies increased osteopontin expression as predictive of reduced relapse-free survival," Clin Cancer Res., 15(22):6939-6946, Epub Nov. 3, 2009.

Coppe et al., "Senescence-associated secretory phenotypes reveal cell-nonautonomous functions of oncogenic RAS and the p53 tumor sunnressor," PLoS Biol., 6(12):2853-2868, Dec. 2, 2008.

Hartman et al., "The Evolution of S100B Inhibitors for the Treatment of Malignant Melanoma", Future medicinal chemistry, Jan. 2013, vol. 5, No. 1, pp. 97-109. (available in PMC. Web pp 1-25), especially abstract, p. 5, 2nd para, p. 7, last para—p. 8, 1st par.

Infante JR et al., "Safety, pharmacokinetic, and pharmacodynamic phase I dose-escalation trial of PF-00562271, an inhibitor of focal adhesion kinase, in advanced solid tumors," J Clin Oncol., 30(13):1527-1533, Epub Mar. 26, 2012.

International Preliminary Report on Patentability received for PCT Patent Application No. PCT/US15/45065, dated Feb. 14, 2017, 11 pages.

International Search Report and Written Opinion received for PCT Patent Application No. PCT/US15/45065, dated Nov. 19, 2015, 14 pages.

Kashani-Sabet et al., "A multi-marker assay to distinguish malignant melanomas from benign nevi," Proc Natl Acad Sci U S A., 106(15):6268-6272, Epub Mar. 30, 2009.

King et al. Gene Expression Profile Analysis by DNA Microarrays. JAMA 2001, vol. 286, No. 18, pp. 2280-2288 (Year: 2001).

Lee et al., "The novel combination of chlorpromazine and pentamidine exerts synergistic antiproliferative effects through dual mitotic action," Cancer Res., 67(23):11359-11367, Dec. 1, 2007.

Meves et al., "Beta1 integrin cytoplasmic tyrosines promote skin tumorigenesis independent of their phosphorylation," Proc Natl Acad Sci U S A., 108(37):15213-15218, Epub Aug. 29, 2011.

Meves, A et al. "Tumor Cell Adhesion as a Risk Factor for Sentinel Lymph Node Metastasis in Primary Cutaneous Melanoma" Journal of Clinical Oncology. Aug. 10, 2015, vol. 33, No. 23; pp. 2509-2515; abstract; p. 2510, 1st col. 3rd paragraph; p. 2511, 2nd column, 4th paragraph; p. 2513, 2nd column, 2nd paragraph; Table 3.

Mitra et al., "Melanoma sentinel node biopsy and prediction models for relapse and overall survival," Br J Cancer., 103(8):1229-1236, Epub Sep. 21, 2010.

NEB catalog (1998/1999), pp. 121, 284. (Year: 1998).

Pathak et al., "Pentamidine is an inhibitor of PRL phosphatases with anticancer activity," Mol Cancer Ther., 1(14):1255-1264, Dec. 2002.

Ruczinski et al., "Logic regression," Journal of Computational and Graphical Statistics, 12(3):475-511, 2003.

Sanovic et al., "Time-resolved gene expression profiling of human squamous cell carcinoma cells during the apoptosis process induced by photodynamic treatment with hypericin," Int. J. Oncol., 35(4):921-39, Oct. 2009.

Seo et al., "The effect of substrate microtopography on focal adhesion maturation and actin organization via the RhoA/ROCK pathway," Biomaterials., 32(36):9568-9575, Epub Sep. 16, 2011.

Siiskonen et al., "Chronic UVR causes increased immunostaining of CD44 and accumulation of hyaluronan in mouse epidermis," J Histochem Cytochem., 59(10):908-917, Epub Aug. 10, 2011.

Simon et al., "Expression of CD44 isoforms in human skin cancer," Eur J Cancer., 32A(8):1394-1400, Jul. 1996.

Smith et al., "The effect of pentamidine on melanoma ex vivo," Anticancer Drugs, 21(2):181-185, Feb. 2010.

Sun and Zhang, "Pentamidine binds to tRNA through non-specific hydrophobic interactions and inhibits aminoacylation and translation," Nucleic Acids Res., 36(5):1654-1664, Mar. 2008.

Sun et al., "Overabundance of putative cancer stem cells in human skin keratinocyte cells malignantly transformed by arsenic," Toxicol Sci., 125(1):20-29, Epub Oct. 19, 2011.

(56) References Cited

OTHER PUBLICATIONS

Talantov et al., "Novel genes associated with malignant melanoma but not benign melanocytic lesions," Clin Cancer Res., 11(20):7234-7242, Oct. 15, 2005.

Waalkes et al., "Pentamidine: clinical pharmacologic correlations in man and mice," Clin Pharmacol Ther., 11(4):505-512, Jul.-Aug. 1970.

Warters et al., "Differential gene expression in primary human skin keratinocytes and fibroblasts in response to ionizing radiation," Radiat Res., 172(1):82-95, Jul. 2009.

Whelan et al., "A method for the absolute quantification of cDNA using real-time PCR," J. Immunol. Methods, 278(1-2):261-9, Jul. 2003.

Yoo et al., "A Comparison of Logistic Regression, Logic Regression, Classification Tree, and Random Forests to Identify Effective Gene-Gene and Gene-Environmental Interactions" International journal of applied science and technology, Aug. 2012, vol. 2, No. 7, pp. 268-284, especially abstract, p. 274, last para, p. 275, 3rd para, last para.

Riker et al. "The gene expression profiles of primary and metastatic melanoma yields a transition point of tumor progression and metastasis" BMC Medical Genomics, Apr. 28, 2008, vol. 1, Article No. 13, DOI: 10.1186/1755-8794-1-13.

Singh et al. "CXCL8 and its cognate receptors in melanoma progression and metastasis" Future Oncology, Jan. 2010, vol. 6, No. 1, pp. 111-116, DOI: 10.2217/fon.09.128.

Singh et al. "Expression of interleukin-8 in primary and metastatic malignant melanoma of the skin" Melanoma Research, Aug. 1999, vol. 9, No. 4, pp. 383-387, DOI: 10.1097/00008390-199908000-00007.

Chinese First Office Action for Chinese Application No. 201780042638.3, dated Sep. 1, 2021, 10 pages (English translation).

* cited by examiner 4-leaf Gene Model
 Best 2 tree, size 4 Model Score =
 -2.72 +
 2.67 * (lamb1 > 250 or plat > 427) +
 3.28 * (itgb3 > 10 and (tp53 ≤ 50))

5-leaf Gene Model
 Best 2 tree, size 5 Model Score =
 -3.22 +
 2.50 * (lamb1 > 250 or plat > 427) +
 3.28 * (itgb3 > 10 and (tp53 ≤ 50) or AGRN > 548.5)

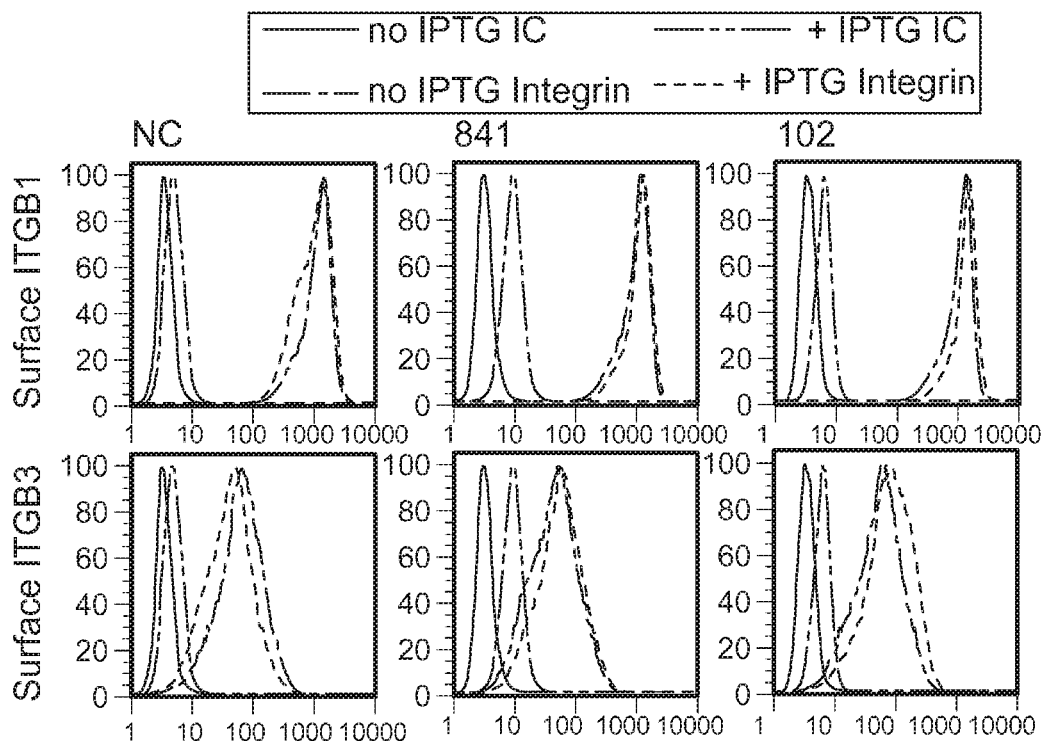
FIG. 13C
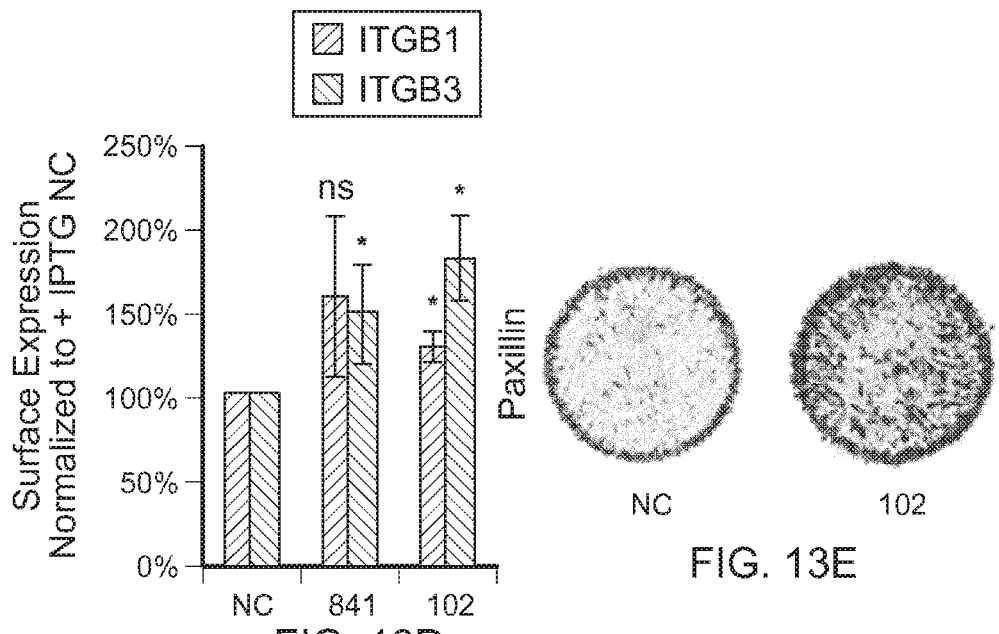
FIG. 13D
FIG. 13E

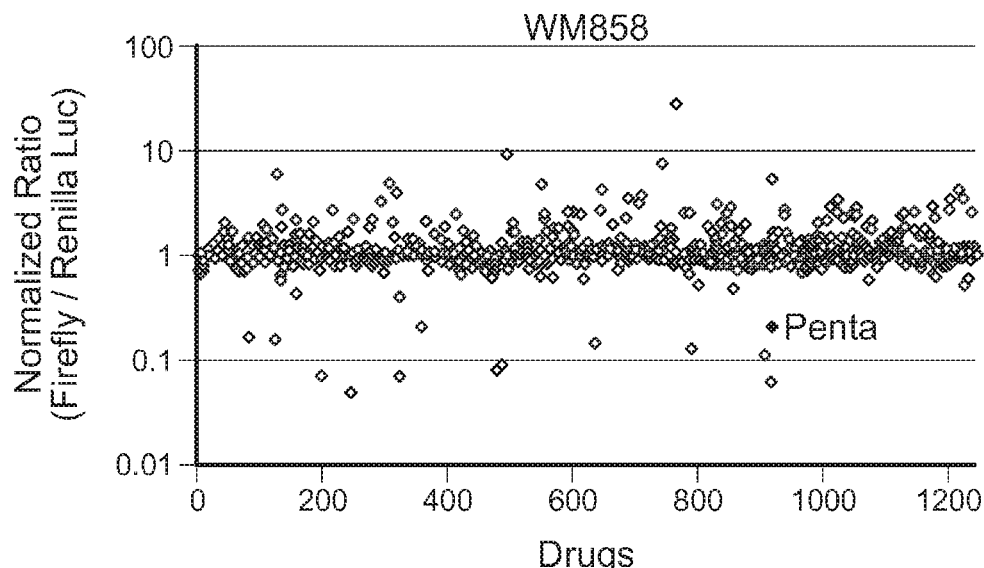
FIG. 15A
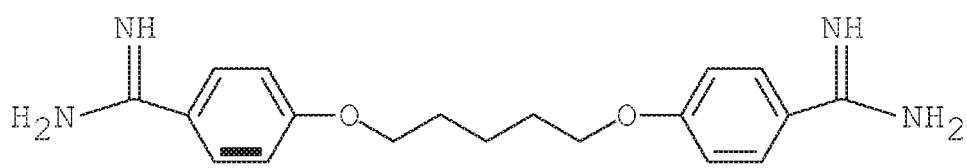
FIG. 15B
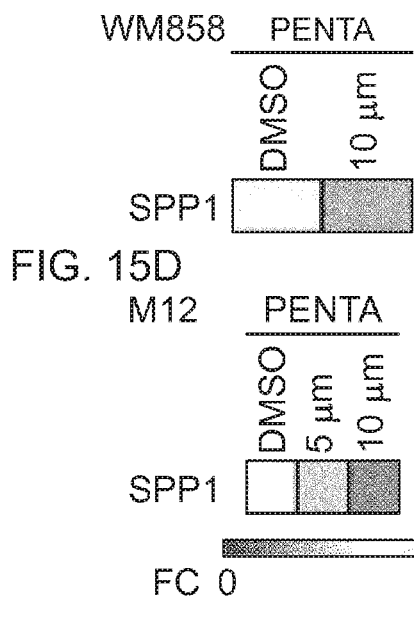
FIG. 15C
FIG. 15D
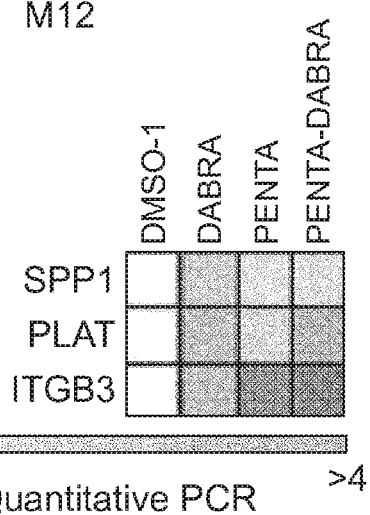
FIG. 15E

- Up-regulation, regionally metastatic melanoma vs. nevi
- Down-regulation, regionally metastatic melanoma vs. nevi
- Up-regulation, regionally metastatic vs. non-metastatic melanoma

SEQUENCE LISTING

<160> NUMBER OF SEQ ID NOS: 442

<210> SEQ ID NO 1
<211> LENGTH: 18
<212> TYPE: DNA
<213> ORGANISM: Homo sapiens

<400> SEQUENCE: 1
gccaaccgcg agaagatg                                                   18

<210> SEQ ID NO 2
<211> LENGTH: 18
<212> TYPE: DNA
<213> ORGANISM: Homo sapiens

<400> SEQUENCE: 2
ggctggggtg ttgaaggt                                                   18

<210> SEQ ID NO 3
<211> LENGTH: 20
<212> TYPE: DNA
<213> ORGANISM: Homo sapiens

<400> SEQUENCE: 3
cgcgagaaga tgacccagat                                                 20

<210> SEQ ID NO 4
<211> LENGTH: 20

<212> TYPE: DNA
<213> ORGANISM: Homo sapiens

<400> SEQUENCE: 4
ggggtgttga aggtctcaaa                                           20

<210> SEQ ID NO 5
<211> LENGTH: 21
<212> TYPE: DNA
<213> ORGANISM: Homo sapiens

<400> SEQUENCE: 5
tgacccagat catgtttgag a                                         21

<210> SEQ ID NO 6
<211> LENGTH: 19
<212> TYPE: DNA
<213> ORGANISM: Homo sapiens

<400> SEQUENCE: 6
gtacatggct ggggtgttg                                            19

<210> SEQ ID NO 7
<211> LENGTH: 18
<212> TYPE: DNA
<213> ORGANISM: Homo sapiens

<400> SEQUENCE: 7
ctgaacccca aggccaac                                             18

<210> SEQ ID NO 8
<211> LENGTH: 20
<212> TYPE: DNA
<213> ORGANISM: Homo sapiens

<400> SEQUENCE: 8
tgatctgggt catcttctcg                                           20

<210> SEQ ID NO 9
<211> LENGTH: 20
<212> TYPE: DNA
<213> ORGANISM: Homo sapiens

<400> SEQUENCE: 9
aactctgcat tctcgcttcc                                           20

<210> SEQ ID NO 10
<211> LENGTH: 20
<212> TYPE: DNA
<213> ORGANISM: Homo sapiens

<400> SEQUENCE: 10
gcagacagac actggcaaca                                           20

<210> SEQ ID NO 11
<211> LENGTH: 21
<212> TYPE: DNA
<213> ORGANISM: Homo sapiens

<400> SEQUENCE: 11
gcaccattga aatcctgagt g                                         21

<210> SEQ ID NO 12

```
<211> LENGTH: 20
<212> TYPE: DNA
<213> ORGANISM: Homo sapiens

<400> SEQUENCE: 12
gctcccactt tgtctccagt                                               20

<210> SEQ ID NO 13
<211> LENGTH: 22
<212> TYPE: DNA
<213> ORGANISM: Homo sapiens

<400> SEQUENCE: 13
tcacagagga aactctgcat tc                                            22

<210> SEQ ID NO 14
<211> LENGTH: 18
<212> TYPE: DNA
<213> ORGANISM: Homo sapiens

<400> SEQUENCE: 14
ggacaccctc caggaagc                                                 18

<210> SEQ ID NO 15
<211> LENGTH: 18
<212> TYPE: DNA
<213> ORGANISM: Homo sapiens

<400> SEQUENCE: 15
atctccaggg gcaccatt                                                 18

<210> SEQ ID NO 16
<211> LENGTH: 21
<212> TYPE: DNA
<213> ORGANISM: Homo sapiens

<400> SEQUENCE: 16
agctgcacat cactcaggat t                                             21

<210> SEQ ID NO 17
<211> LENGTH: 19
<212> TYPE: DNA
<213> ORGANISM: Homo sapiens

<400> SEQUENCE: 17
actgctggcc acgagtacg                                                19

<210> SEQ ID NO 18
<211> LENGTH: 20
<212> TYPE: DNA
<213> ORGANISM: Homo sapiens

<400> SEQUENCE: 18
atgctccaca ggattcatgg                                               20

<210> SEQ ID NO 19
<211> LENGTH: 20
<212> TYPE: DNA
<213> ORGANISM: Homo sapiens

<400> SEQUENCE: 19
acagagctgt ggttggtgtg                                               20
```

```
<210> SEQ ID NO 20
<211> LENGTH: 18
<212> TYPE: DNA
<213> ORGANISM: Homo sapiens

<400> SEQUENCE: 20
ttgtcaattc ggccacct                                                       18

<210> SEQ ID NO 21
<211> LENGTH: 21
<212> TYPE: DNA
<213> ORGANISM: Homo sapiens

<400> SEQUENCE: 21
tatctcctca gccaacagag c                                                   21

<210> SEQ ID NO 22
<211> LENGTH: 18
<212> TYPE: DNA
<213> ORGANISM: Homo sapiens

<400> SEQUENCE: 22
agccaccaca ccaaccac                                                       18

<210> SEQ ID NO 23
<211> LENGTH: 19
<212> TYPE: DNA
<213> ORGANISM: Homo sapiens

<400> SEQUENCE: 23
gtgtggccat gaatcctgt                                                      19

<210> SEQ ID NO 24
<211> LENGTH: 20
<212> TYPE: DNA
<213> ORGANISM: Homo sapiens

<400> SEQUENCE: 24
ccacctccaa aaggatgctc                                                     20

<210> SEQ ID NO 25
<211> LENGTH: 20
<212> TYPE: DNA
<213> ORGANISM: Homo sapiens

<400> SEQUENCE: 25
tctctctttc tggcctggag                                                     20

<210> SEQ ID NO 26
<211> LENGTH: 21
<212> TYPE: DNA
<213> ORGANISM: Homo sapiens

<400> SEQUENCE: 26
gaatctttgg agtacgctgg a                                                   21

<210> SEQ ID NO 27
<211> LENGTH: 20
<212> TYPE: DNA
<213> ORGANISM: Homo sapiens

<400> SEQUENCE: 27
tggaggctat ccagcgtact                                                     20
```

```
<210> SEQ ID NO 28
<211> LENGTH: 23
<212> TYPE: DNA
<213> ORGANISM: Homo sapiens

<400> SEQUENCE: 28
cgtgagtaaa cctgaatctt tgg                                          23

<210> SEQ ID NO 29
<211> LENGTH: 21
<212> TYPE: DNA
<213> ORGANISM: Homo sapiens

<400> SEQUENCE: 29
ccagcgtact ccaaagattc a                                            21

<210> SEQ ID NO 30
<211> LENGTH: 20
<212> TYPE: DNA
<213> ORGANISM: Homo sapiens

<400> SEQUENCE: 30
tctctgctgg atgacgtgag                                              20

<210> SEQ ID NO 31
<211> LENGTH: 20
<212> TYPE: DNA
<213> ORGANISM: Homo sapiens

<400> SEQUENCE: 31
ggctatccag cgtactccaa                                              20

<210> SEQ ID NO 32
<211> LENGTH: 21
<212> TYPE: DNA
<213> ORGANISM: Homo sapiens

<400> SEQUENCE: 32
gctggatgac gtgagtaaac c                                            21

<210> SEQ ID NO 33
<211> LENGTH: 20
<212> TYPE: DNA
<213> ORGANISM: Homo sapiens

<400> SEQUENCE: 33
accattgagg acctgaggaa                                              20

<210> SEQ ID NO 34
<211> LENGTH: 20
<212> TYPE: DNA
<213> ORGANISM: Homo sapiens

<400> SEQUENCE: 34
gtccactgtg gctgtgagaa                                              20

<210> SEQ ID NO 35
<211> LENGTH: 20
<212> TYPE: DNA
<213> ORGANISM: Homo sapiens

<400> SEQUENCE: 35
cattgaggac ctgaggaaca                                              20
```

```
<210> SEQ ID NO 36
<211> LENGTH: 20
<212> TYPE: DNA
<213> ORGANISM: Homo sapiens

<400> SEQUENCE: 36
aatctgcaga aggacattgg                                              20

<210> SEQ ID NO 37
<211> LENGTH: 20
<212> TYPE: DNA
<213> ORGANISM: Homo sapiens

<400> SEQUENCE: 37
gatgacttcc gcaccaagta                                              20

<210> SEQ ID NO 38
<211> LENGTH: 20
<212> TYPE: DNA
<213> ORGANISM: Homo sapiens

<400> SEQUENCE: 38
cgcaggttca actctgtctc                                              20

<210> SEQ ID NO 39
<211> LENGTH: 20
<212> TYPE: DNA
<213> ORGANISM: Homo sapiens

<400> SEQUENCE: 39
tccgcaccaa gtatgagaca                                              20

<210> SEQ ID NO 40
<211> LENGTH: 20
<212> TYPE: DNA
<213> ORGANISM: Homo sapiens

<400> SEQUENCE: 40
actcatgcgc aggttcaact                                              20

<210> SEQ ID NO 41
<211> LENGTH: 20
<212> TYPE: DNA
<213> ORGANISM: Homo sapiens

<400> SEQUENCE: 41
gagcctcgtg actacagcaa                                              20

<210> SEQ ID NO 42
<211> LENGTH: 22
<212> TYPE: DNA
<213> ORGANISM: Homo sapiens

<400> SEQUENCE: 42
gcaggatgtt ggcattatca gt                                           22

<210> SEQ ID NO 43
<211> LENGTH: 23
<212> TYPE: DNA
<213> ORGANISM: Homo sapiens

<400> SEQUENCE: 43
```

```
aaaaccatcg atgaccttaa aaa                                            23

<210> SEQ ID NO 44
<211> LENGTH: 20
<212> TYPE: DNA
<213> ORGANISM: Homo sapiens

<400> SEQUENCE: 44
gatctgaagc aggatgttgg                                                20

<210> SEQ ID NO 45
<211> LENGTH: 21
<212> TYPE: DNA
<213> ORGANISM: Homo sapiens

<400> SEQUENCE: 45
ttcccaagtc aaatgatcca g                                              21

<210> SEQ ID NO 46
<211> LENGTH: 20
<212> TYPE: DNA
<213> ORGANISM: Homo sapiens

<400> SEQUENCE: 46
aagatggttc ccttgttcca                                                20

<210> SEQ ID NO 47
<211> LENGTH: 20
<212> TYPE: DNA
<213> ORGANISM: Homo sapiens

<400> SEQUENCE: 47
cggcatttgt tgctcagaat                                                20

<210> SEQ ID NO 48
<211> LENGTH: 20
<212> TYPE: DNA
<213> ORGANISM: Homo sapiens

<400> SEQUENCE: 48
gagcctgcat ttcaagttcc                                                20

<210> SEQ ID NO 49
<211> LENGTH: 21
<212> TYPE: DNA
<213> ORGANISM: Homo sapiens

<400> SEQUENCE: 49
ttccttcttc accatgcatt t                                              21

<210> SEQ ID NO 50
<211> LENGTH: 20
<212> TYPE: DNA
<213> ORGANISM: Homo sapiens

<400> SEQUENCE: 50
ggagccactg ctcaaaaata                                                20

<210> SEQ ID NO 51
<211> LENGTH: 20
<212> TYPE: DNA
<213> ORGANISM: Homo sapiens

<400> SEQUENCE: 51
```

```
tccaaagatc tgggctatga                                              20
```

<210> SEQ ID NO 52
<211> LENGTH: 22
<212> TYPE: DNA
<213> ORGANISM: Homo sapiens

<400> SEQUENCE: 52

```
ttgaaaagag tctgggtctg aa                                           22
```

<210> SEQ ID NO 53
<211> LENGTH: 22
<212> TYPE: DNA
<213> ORGANISM: Homo sapiens

<400> SEQUENCE: 53

```
gagaaaaact gtgaacctgt gg                                           22
```

<210> SEQ ID NO 54
<211> LENGTH: 20
<212> TYPE: DNA
<213> ORGANISM: Homo sapiens

<400> SEQUENCE: 54

```
ataagcaggt ggagcattgg                                              20
```

<210> SEQ ID NO 55
<211> LENGTH: 22
<212> TYPE: DNA
<213> ORGANISM: Homo sapiens

<400> SEQUENCE: 55

```
gaagacgaaa tggatacaga gc                                           22
```

<210> SEQ ID NO 56
<211> LENGTH: 23
<212> TYPE: DNA
<213> ORGANISM: Homo sapiens

<400> SEQUENCE: 56

```
gtgccaacat gaagactttt atc                                          23
```

<210> SEQ ID NO 57
<211> LENGTH: 20
<212> TYPE: DNA
<213> ORGANISM: Homo sapiens

<400> SEQUENCE: 57

```
gtggtcagca cccagcttat                                              20
```

<210> SEQ ID NO 58
<211> LENGTH: 19
<212> TYPE: DNA
<213> ORGANISM: Homo sapiens

<400> SEQUENCE: 58

```
ccaaggcctg cttcttgac                                               19
```

<210> SEQ ID NO 59
<211> LENGTH: 20
<212> TYPE: DNA
<213> ORGANISM: Homo sapiens

<400> SEQUENCE: 59
gctgtggtcc ttgcatctct                                               20

<210> SEQ ID NO 60
<211> LENGTH: 20
<212> TYPE: DNA
<213> ORGANISM: Homo sapiens

<400> SEQUENCE: 60
gcttcataag tctgcgccta                                               20

<210> SEQ ID NO 61
<211> LENGTH: 19
<212> TYPE: DNA
<213> ORGANISM: Homo sapiens

<400> SEQUENCE: 61
ctcctgcaca tgctttgga                                                19

<210> SEQ ID NO 62
<211> LENGTH: 18
<212> TYPE: DNA
<213> ORGANISM: Homo sapiens

<400> SEQUENCE: 62
aggtctgcgg cagttgtc                                                 18

<210> SEQ ID NO 63
<211> LENGTH: 20
<212> TYPE: DNA
<213> ORGANISM: Homo sapiens

<400> SEQUENCE: 63
aggctttgga agtggtcatt                                               20

<210> SEQ ID NO 64
<211> LENGTH: 20
<212> TYPE: DNA
<213> ORGANISM: Homo sapiens

<400> SEQUENCE: 64
ccattgtcat ggcaccatct                                               20

<210> SEQ ID NO 65
<211> LENGTH: 24
<212> TYPE: DNA
<213> ORGANISM: Homo sapiens

<400> SEQUENCE: 65
gaagtggtca tttcagatgt gatt                                          24

<210> SEQ ID NO 66
<211> LENGTH: 20
<212> TYPE: DNA
<213> ORGANISM: Homo sapiens

<400> SEQUENCE: 66
ccattgtcat ggcaccatct                                               20

<210> SEQ ID NO 67
<211> LENGTH: 23
<212> TYPE: DNA
<213> ORGANISM: Homo sapiens

```
<400> SEQUENCE: 67
tggtcatttc agatgtgatt cat                                           23

<210> SEQ ID NO 68
<211> LENGTH: 20
<212> TYPE: DNA
<213> ORGANISM: Homo sapiens

<400> SEQUENCE: 68
cattgtcatg gcaccatcta                                               20

<210> SEQ ID NO 69
<211> LENGTH: 20
<212> TYPE: DNA
<213> ORGANISM: Homo sapiens

<400> SEQUENCE: 69
gtttcgcaga cctgacatcc                                               20

<210> SEQ ID NO 70
<211> LENGTH: 20
<212> TYPE: DNA
<213> ORGANISM: Homo sapiens

<400> SEQUENCE: 70
tcctcgtctg tagcatcagg                                               20

<210> SEQ ID NO 71
<211> LENGTH: 20
<212> TYPE: DNA
<213> ORGANISM: Homo sapiens

<400> SEQUENCE: 71
cctgacatcc agtaccctga                                               20

<210> SEQ ID NO 72
<211> LENGTH: 20
<212> TYPE: DNA
<213> ORGANISM: Homo sapiens

<400> SEQUENCE: 72
tgaggtgatg tcctcgtctg                                               20

<210> SEQ ID NO 73
<211> LENGTH: 20
<212> TYPE: DNA
<213> ORGANISM: Homo sapiens

<400> SEQUENCE: 73
gaatctccta gccccacaga                                               20

<210> SEQ ID NO 74
<211> LENGTH: 21
<212> TYPE: DNA
<213> ORGANISM: Homo sapiens

<400> SEQUENCE: 74
ggtttcttca gaggacacag c                                             21

<210> SEQ ID NO 75
<211> LENGTH: 22
<212> TYPE: DNA
```

```
<213> ORGANISM: Homo sapiens

<400> SEQUENCE: 75
cccatctcag aagcagaatc tc                                          22

<210> SEQ ID NO 76
<211> LENGTH: 19
<212> TYPE: DNA
<213> ORGANISM: Homo sapiens

<400> SEQUENCE: 76
acagcattct gtggggcta                                              19

<210> SEQ ID NO 77
<211> LENGTH: 19
<212> TYPE: DNA
<213> ORGANISM: Homo sapiens

<400> SEQUENCE: 77
ggaaaaccag gacccagag                                              19

<210> SEQ ID NO 78
<211> LENGTH: 20
<212> TYPE: DNA
<213> ORGANISM: Homo sapiens

<400> SEQUENCE: 78 cttttttcccc tttgtcacca                                            20

<210> SEQ ID NO 79
<211> LENGTH: 20
<212> TYPE: DNA
<213> ORGANISM: Homo sapiens

<400> SEQUENCE: 79
agaaaggtga acccggaaaa                                             20

<210> SEQ ID NO 80
<211> LENGTH: 18
<212> TYPE: DNA
<213> ORGANISM: Homo sapiens

<400> SEQUENCE: 80
ggtttgcctc tgggtcct                                               18

<210> SEQ ID NO 81
<211> LENGTH: 20
<212> TYPE: DNA
<213> ORGANISM: Homo sapiens

<400> SEQUENCE: 81
gagaaaaggg ccaaaaaggt                                             20

<210> SEQ ID NO 82
<211> LENGTH: 20
<212> TYPE: DNA
<213> ORGANISM: Homo sapiens

<400> SEQUENCE: 82 catccccctga aatccaggtt                                            20

<210> SEQ ID NO 83
<211> LENGTH: 20
```

```
<212> TYPE: DNA
<213> ORGANISM: Homo sapiens

<400> SEQUENCE: 83
aaagggccaa aaaggtgaac                                              20

<210> SEQ ID NO 84
<211> LENGTH: 18
<212> TYPE: DNA
<213> ORGANISM: Homo sapiens

<400> SEQUENCE: 84
cctggcatcc cctgaaat                                                18

<210> SEQ ID NO 85
<211> LENGTH: 20
<212> TYPE: DNA
<213> ORGANISM: Homo sapiens

<400> SEQUENCE: 85
gtgtcaacct gatggggaga                                              20

<210> SEQ ID NO 86
<211> LENGTH: 20
<212> TYPE: DNA
<213> ORGANISM: Homo sapiens

<400> SEQUENCE: 86
gttaacgccc tgactgtggt                                              20

<210> SEQ ID NO 87
<211> LENGTH: 20
<212> TYPE: DNA
<213> ORGANISM: Homo sapiens

<400> SEQUENCE: 87
ggtacagtgg gacagcaggt                                              20

<210> SEQ ID NO 88
<211> LENGTH: 20
<212> TYPE: DNA
<213> ORGANISM: Homo sapiens

<400> SEQUENCE: 88
gatctgccat tgtggtaggc                                              20

<210> SEQ ID NO 89
<211> LENGTH: 19
<212> TYPE: DNA
<213> ORGANISM: Homo sapiens

<400> SEQUENCE: 89
aaccacagtc agggcgtta                                               19

<210> SEQ ID NO 90
<211> LENGTH: 18
<212> TYPE: DNA
<213> ORGANISM: Homo sapiens

<400> SEQUENCE: 90
gttcgtggcc cttccagt                                                18

<210> SEQ ID NO 91
```

```
<211> LENGTH: 20
<212> TYPE: DNA
<213> ORGANISM: Homo sapiens

<400> SEQUENCE: 91
aagctgaagg tggagggta                                                    20

<210> SEQ ID NO 92
<211> LENGTH: 20
<212> TYPE: DNA
<213> ORGANISM: Homo sapiens

<400> SEQUENCE: 92
gagtcacctg ctgtcccact                                                    20

<210> SEQ ID NO 93
<211> LENGTH: 20
<212> TYPE: DNA
<213> ORGANISM: Homo sapiens

<400> SEQUENCE: 93
tattcctccg aaccagcatc                                                    20

<210> SEQ ID NO 94
<211> LENGTH: 20
<212> TYPE: DNA
<213> ORGANISM: Homo sapiens

<400> SEQUENCE: 94
caccagctcc gagtcaatgt                                                    20

<210> SEQ ID NO 95
<211> LENGTH: 20
<212> TYPE: DNA
<213> ORGANISM: Homo sapiens

<400> SEQUENCE: 95
ccaccatcaa catggagaac                                                    20

<210> SEQ ID NO 96
<211> LENGTH: 22
<212> TYPE: DNA
<213> ORGANISM: Homo sapiens

<400> SEQUENCE: 96
agtcaatgtc cacagagaac ca                                                 22

<210> SEQ ID NO 97
<211> LENGTH: 20
<212> TYPE: DNA
<213> ORGANISM: Homo sapiens

<400> SEQUENCE: 97
caactgccac attggtgatg                                                    20

<210> SEQ ID NO 98
<211> LENGTH: 20
<212> TYPE: DNA
<213> ORGANISM: Homo sapiens

<400> SEQUENCE: 98
aaacctcctg ttggcctctt                                                    20
```

```
<210> SEQ ID NO 99
<211> LENGTH: 20
<212> TYPE: DNA
<213> ORGANISM: Homo sapiens

<400> SEQUENCE: 99
tgacatcacg gatgtgaagc                                              20

<210> SEQ ID NO 100
<211> LENGTH: 20
<212> TYPE: DNA
<213> ORGANISM: Homo sapiens

<400> SEQUENCE: 100
gggttgatga caacctggag                                              20

<210> SEQ ID NO 101
<211> LENGTH: 19
<212> TYPE: DNA
<213> ORGANISM: Homo sapiens

<400> SEQUENCE: 101
tgtgaccgag agcgagaag                                               19

<210> SEQ ID NO 102
<211> LENGTH: 21
<212> TYPE: DNA
<213> ORGANISM: Homo sapiens

<400> SEQUENCE: 102
caggctcagt tcaaagtggt t                                            21

<210> SEQ ID NO 103
<211> LENGTH: 20
<212> TYPE: DNA
<213> ORGANISM: Homo sapiens

<400> SEQUENCE: 103
cggacctttg tcgagtacct                                              20

<210> SEQ ID NO 104
<211> LENGTH: 20
<212> TYPE: DNA
<213> ORGANISM: Homo sapiens

<400> SEQUENCE: 104
gttgctctgc agtgccttct                                              20

<210> SEQ ID NO 105
<211> LENGTH: 20
<212> TYPE: DNA
<213> ORGANISM: Homo sapiens

<400> SEQUENCE: 105
gacttccgtt ggactgatgg                                              20

<210> SEQ ID NO 106
<211> LENGTH: 20
<212> TYPE: DNA
<213> ORGANISM: Homo sapiens

<400> SEQUENCE: 106
tggttgggtc tccaattctc                                              20
```

```
<210> SEQ ID NO 107
<211> LENGTH: 20
<212> TYPE: DNA
<213> ORGANISM: Homo sapiens

<400> SEQUENCE: 107
acgtgcaaga aaggaacagt                                                    20

<210> SEQ ID NO 108
<211> LENGTH: 20
<212> TYPE: DNA
<213> ORGANISM: Homo sapiens

<400> SEQUENCE: 108
tccaaaggtc ttggcatttt                                                    20

<210> SEQ ID NO 109
<211> LENGTH: 20
<212> TYPE: DNA
<213> ORGANISM: Homo sapiens

<400> SEQUENCE: 109
gcagagatgg agcactacgg                                                    20

<210> SEQ ID NO 110
<211> LENGTH: 19
<212> TYPE: DNA
<213> ORGANISM: Homo sapiens

<400> SEQUENCE: 110
cagccttgaa tcctcatgc                                                     19

<210> SEQ ID NO 111
<211> LENGTH: 19
<212> TYPE: DNA
<213> ORGANISM: Homo sapiens

<400> SEQUENCE: 111
ggaaggaatc gtggagcag                                                     19

<210> SEQ ID NO 112
<211> LENGTH: 20
<212> TYPE: DNA
<213> ORGANISM: Homo sapiens

<400> SEQUENCE: 112
cagcagtggg aaccagtaca                                                    20

<210> SEQ ID NO 113
<211> LENGTH: 22
<212> TYPE: DNA
<213> ORGANISM: Homo sapiens

<400> SEQUENCE: 113
ctgatgaatg aaatgaggag ga                                                 22

<210> SEQ ID NO 114
<211> LENGTH: 20
<212> TYPE: DNA
<213> ORGANISM: Homo sapiens

<400> SEQUENCE: 114
cacaaatgag ccaaatccaa                                                    20
```

```
<210> SEQ ID NO 115
<211> LENGTH: 21
<212> TYPE: DNA
<213> ORGANISM: Homo sapiens

<400> SEQUENCE: 115
cagtttgctg tgtgtttgct c                                              21

<210> SEQ ID NO 116
<211> LENGTH: 21
<212> TYPE: DNA
<213> ORGANISM: Homo sapiens

<400> SEQUENCE: 116
catgatttgg catttgcttt t                                              21

<210> SEQ ID NO 117
<211> LENGTH: 20
<212> TYPE: DNA
<213> ORGANISM: Homo sapiens

<400> SEQUENCE: 117
gccccaccag aggagtatgt                                                20

<210> SEQ ID NO 118
<211> LENGTH: 19
<212> TYPE: DNA
<213> ORGANISM: Homo sapiens

<400> SEQUENCE: 118
aagccgactt ccttcacca                                                 19

<210> SEQ ID NO 119
<211> LENGTH: 20
<212> TYPE: DNA
<213> ORGANISM: Homo sapiens

<400> SEQUENCE: 119
gagaccattc ccctcctacc                                                20

<210> SEQ ID NO 120
<211> LENGTH: 21
<212> TYPE: DNA
<213> ORGANISM: Homo sapiens

<400> SEQUENCE: 120
gcttctgtgc catctcaatc t                                              21

<210> SEQ ID NO 121
<211> LENGTH: 20
<212> TYPE: DNA
<213> ORGANISM: Homo sapiens

<400> SEQUENCE: 121
cgaagctgac ctggaagaga                                                20

<210> SEQ ID NO 122
<211> LENGTH: 20
<212> TYPE: DNA
<213> ORGANISM: Homo sapiens

<400> SEQUENCE: 122
```
tgggagtacg gatgcacttt                      20

<210> SEQ ID NO 123
<211> LENGTH: 18
<212> TYPE: DNA
<213> ORGANISM: Homo sapiens

<400> SEQUENCE: 123
gtgtgcaccg ccaaagat                        18

<210> SEQ ID NO 124
<211> LENGTH: 19
<212> TYPE: DNA
<213> ORGANISM: Homo sapiens

<400> SEQUENCE: 124
cgtaccaccg aagatgcag                       19

<210> SEQ ID NO 125
<211> LENGTH: 20
<212> TYPE: DNA
<213> ORGANISM: Homo sapiens

<400> SEQUENCE: 125
ctaccccggc tactacacca                      20

<210> SEQ ID NO 126
<211> LENGTH: 20
<212> TYPE: DNA
<213> ORGANISM: Homo sapiens

<400> SEQUENCE: 126
gacaaaggcc aggtcaaact                      20

<210> SEQ ID NO 127
<211> LENGTH: 19
<212> TYPE: DNA
<213> ORGANISM: Homo sapiens

<400> SEQUENCE: 127
agtcggggtg gattacgag                       19

<210> SEQ ID NO 128
<211> LENGTH: 20
<212> TYPE: DNA
<213> ORGANISM: Homo sapiens

<400> SEQUENCE: 128
acagttgtag cgcaggaacc                      20

<210> SEQ ID NO 129
<211> LENGTH: 19
<212> TYPE: DNA
<213> ORGANISM: Homo sapiens

<400> SEQUENCE: 129
atgatgatgg cagggatgg                       19

<210> SEQ ID NO 130
<211> LENGTH: 20
<212> TYPE: DNA
<213> ORGANISM: Homo sapiens

<400> SEQUENCE: 130
gcattgatct cggcttcttg        20

<210> SEQ ID NO 131
<211> LENGTH: 20
<212> TYPE: DNA
<213> ORGANISM: Homo sapiens

<400> SEQUENCE: 131
ctgtggcaca caggaaacac        20

<210> SEQ ID NO 132
<211> LENGTH: 18
<212> TYPE: DNA
<213> ORGANISM: Homo sapiens

<400> SEQUENCE: 132
acgagggtca tgccacag          18

<210> SEQ ID NO 133
<211> LENGTH: 20
<212> TYPE: DNA
<213> ORGANISM: Homo sapiens

<400> SEQUENCE: 133
gccaaagacg ggtttcatta        20

<210> SEQ ID NO 134
<211> LENGTH: 20
<212> TYPE: DNA
<213> ORGANISM: Homo sapiens

<400> SEQUENCE: 134
gccatgattt tcttcccttc        20

<210> SEQ ID NO 135
<211> LENGTH: 19
<212> TYPE: DNA
<213> ORGANISM: Homo sapiens

<400> SEQUENCE: 135
ctcctcctac ggcaaggga         19

<210> SEQ ID NO 136
<211> LENGTH: 23
<212> TYPE: DNA
<213> ORGANISM: Homo sapiens

<400> SEQUENCE: 136
tggagattgt ctaaccagat ggg    23

<210> SEQ ID NO 137
<211> LENGTH: 20
<212> TYPE: DNA
<213> ORGANISM: Homo sapiens

<400> SEQUENCE: 137
ctcctacggc aagggagaag        20

<210> SEQ ID NO 138
<211> LENGTH: 21
<212> TYPE: DNA
<213> ORGANISM: Homo sapiens

```
<400> SEQUENCE: 138
ttgccagtac agtggagatt g                                      21

<210> SEQ ID NO 139
<211> LENGTH: 20
<212> TYPE: DNA
<213> ORGANISM: Homo sapiens

<400> SEQUENCE: 139
ccagagctgt gcagatgagt                                        20

<210> SEQ ID NO 140
<211> LENGTH: 23
<212> TYPE: DNA
<213> ORGANISM: Homo sapiens

<400> SEQUENCE: 140
tgcatctaga ttctttgcct ttt                                    23

<210> SEQ ID NO 141
<211> LENGTH: 19
<212> TYPE: DNA
<213> ORGANISM: Homo sapiens

<400> SEQUENCE: 141
agggcacagc agacttcct                                         19

<210> SEQ ID NO 142
<211> LENGTH: 20
<212> TYPE: DNA
<213> ORGANISM: Homo sapiens

<400> SEQUENCE: 142
tcgtccatgc tgtggtaatg                                        20

<210> SEQ ID NO 143
<211> LENGTH: 19
<212> TYPE: DNA
<213> ORGANISM: Homo sapiens

<400> SEQUENCE: 143
gcatgcacct ctcataccc                                         19

<210> SEQ ID NO 144
<211> LENGTH: 21
<212> TYPE: DNA
<213> ORGANISM: Homo sapiens

<400> SEQUENCE: 144
cgcattgtag gtgtcatagc a                                      21

<210> SEQ ID NO 145
<211> LENGTH: 19
<212> TYPE: DNA
<213> ORGANISM: Homo sapiens

<400> SEQUENCE: 145
cttggcagcc ttcctgatt                                         19

<210> SEQ ID NO 146
<211> LENGTH: 20
<212> TYPE: DNA
<213> ORGANISM: Homo sapiens
```

```
<400> SEQUENCE: 146
gcaaaactgc accttcacac                                          20

<210> SEQ ID NO 147
<211> LENGTH: 18
<212> TYPE: DNA
<213> ORGANISM: Homo sapiens

<400> SEQUENCE: 147
cgctctgaag gggatctg                                            18

<210> SEQ ID NO 148
<211> LENGTH: 20
<212> TYPE: DNA
<213> ORGANISM: Homo sapiens

<400> SEQUENCE: 148
acagggtctg ccctctgact                                          20

<210> SEQ ID NO 149
<211> LENGTH: 20
<212> TYPE: DNA
<213> ORGANISM: Homo sapiens

<400> SEQUENCE: 149
gagctcagtc agagggcaga                                          20

<210> SEQ ID NO 150
<211> LENGTH: 21
<212> TYPE: DNA
<213> ORGANISM: Homo sapiens

<400> SEQUENCE: 150
aactttcccc gttttggtag a                                        21

<210> SEQ ID NO 151
<211> LENGTH: 21
<212> TYPE: DNA
<213> ORGANISM: Homo sapiens

<400> SEQUENCE: 151
tgaacagtgt ggatgagatg g                                        21

<210> SEQ ID NO 152
<211> LENGTH: 20
<212> TYPE: DNA
<213> ORGANISM: Homo sapiens

<400> SEQUENCE: 152
gcagggtgct ttggttgata                                          20

<210> SEQ ID NO 153
<211> LENGTH: 21
<212> TYPE: DNA
<213> ORGANISM: Homo sapiens

<400> SEQUENCE: 153
aagggtctcc agcacctcta c                                        21

<210> SEQ ID NO 154
<211> LENGTH: 20
<212> TYPE: DNA
```

```
<213> ORGANISM: Homo sapiens

<400> SEQUENCE: 154
aaggccttct catggatctt                                              20

<210> SEQ ID NO 155
<211> LENGTH: 19
<212> TYPE: DNA
<213> ORGANISM: Homo sapiens

<400> SEQUENCE: 155
gagctccgca aggatgact                                               19

<210> SEQ ID NO 156
<211> LENGTH: 19
<212> TYPE: DNA
<213> ORGANISM: Homo sapiens

<400> SEQUENCE: 156
aggacgaggg cgtagaggt                                               19

<210> SEQ ID NO 157
<211> LENGTH: 20
<212> TYPE: DNA
<213> ORGANISM: Homo sapiens

<400> SEQUENCE: 157
cattcaagga acccagaacc                                              20

<210> SEQ ID NO 158
<211> LENGTH: 20
<212> TYPE: DNA
<213> ORGANISM: Homo sapiens

<400> SEQUENCE: 158
gcgttgaaca aggtttcctc                                              20

<210> SEQ ID NO 159
<211> LENGTH: 20
<212> TYPE: DNA
<213> ORGANISM: Homo sapiens

<400> SEQUENCE: 159
aagagccaga gtgtcccaag                                              20

<210> SEQ ID NO 160
<211> LENGTH: 19
<212> TYPE: DNA
<213> ORGANISM: Homo sapiens

<400> SEQUENCE: 160
actgagagca ggaccacca                                               19

<210> SEQ ID NO 161
<211> LENGTH: 21
<212> TYPE: DNA
<213> ORGANISM: Homo sapiens

<400> SEQUENCE: 161
cttctcctgt gtccgctaca a                                            21

<210> SEQ ID NO 162
<211> LENGTH: 19
```

```
<212> TYPE: DNA
<213> ORGANISM: Homo sapiens

<400> SEQUENCE: 162
catggcctga gcacatctc                                                 19

<210> SEQ ID NO 163
<211> LENGTH: 21
<212> TYPE: DNA
<213> ORGANISM: Homo sapiens

<400> SEQUENCE: 163
tgcctgcacc tttaagaaag a                                              21

<210> SEQ ID NO 164
<211> LENGTH: 22
<212> TYPE: DNA
<213> ORGANISM: Homo sapiens

<400> SEQUENCE: 164
ccggtcaaac ttcttacact cc                                             22

<210> SEQ ID NO 165
<211> LENGTH: 19
<212> TYPE: DNA
<213> ORGANISM: Homo sapiens

<400> SEQUENCE: 165 aaggggggaga tgtgctcag                                                19

<210> SEQ ID NO 166
<211> LENGTH: 18
<212> TYPE: DNA
<213> ORGANISM: Homo sapiens

<400> SEQUENCE: 166
cagtccccac agctgcac                                                  18

<210> SEQ ID NO 167
<211> LENGTH: 21
<212> TYPE: DNA
<213> ORGANISM: Homo sapiens

<400> SEQUENCE: 167
aaaccgaagt catagccaca c                                              21

<210> SEQ ID NO 168
<211> LENGTH: 19
<212> TYPE: DNA
<213> ORGANISM: Homo sapiens

<400> SEQUENCE: 168
aagctttccg cccattctt                                                 19

<210> SEQ ID NO 169
<211> LENGTH: 20
<212> TYPE: DNA
<213> ORGANISM: Homo sapiens

<400> SEQUENCE: 169
aggcccaaga ctggctacat                                                20

<210> SEQ ID NO 170
```

<211> LENGTH: 20
<212> TYPE: DNA
<213> ORGANISM: Homo sapiens

<400> SEQUENCE: 170
ctgccatgac ctgtttcct            20

<210> SEQ ID NO 171
<211> LENGTH: 19
<212> TYPE: DNA
<213> ORGANISM: Homo sapiens

<400> SEQUENCE: 171
ggcaggtgcg aaccttatg            19

<210> SEQ ID NO 172
<211> LENGTH: 19
<212> TYPE: DNA
<213> ORGANISM: Homo sapiens

<400> SEQUENCE: 172
ccttccagcc aatgttcct            19

<210> SEQ ID NO 173
<211> LENGTH: 19
<212> TYPE: DNA
<213> ORGANISM: Homo sapiens

<400> SEQUENCE: 173
gatcgctgag ctgaaggtg            19

<210> SEQ ID NO 174
<211> LENGTH: 18
<212> TYPE: DNA
<213> ORGANISM: Homo sapiens

<400> SEQUENCE: 174
cggatgcccc atctgagt             18

<210> SEQ ID NO 175
<211> LENGTH: 21
<212> TYPE: DNA
<213> ORGANISM: Homo sapiens

<400> SEQUENCE: 175
cccattggcg agtttgagaa g         21

<210> SEQ ID NO 176
<211> LENGTH: 22
<212> TYPE: DNA
<213> ORGANISM: Homo sapiens

<400> SEQUENCE: 176
aggaagagtc gaaggtcttg tt        22

<210> SEQ ID NO 177
<211> LENGTH: 20
<212> TYPE: DNA
<213> ORGANISM: Homo sapiens

<400> SEQUENCE: 177
ggaagaaact gtggcagagg           20

```
<210> SEQ ID NO 178
<211> LENGTH: 20
<212> TYPE: DNA
<213> ORGANISM: Homo sapiens

<400> SEQUENCE: 178
ggacaggatt agctcccaca                                              20

<210> SEQ ID NO 179
<211> LENGTH: 20
<212> TYPE: DNA
<213> ORGANISM: Homo sapiens

<400> SEQUENCE: 179
acaacgttct gtccccttg                                               20

<210> SEQ ID NO 180
<211> LENGTH: 20
<212> TYPE: DNA
<213> ORGANISM: Homo sapiens

<400> SEQUENCE: 180
ggggacagca tcaaatcatc                                              20

<210> SEQ ID NO 181
<211> LENGTH: 21
<212> TYPE: DNA
<213> ORGANISM: Homo sapiens

<400> SEQUENCE: 181
tggatgcaga tgttgttttg a                                            21

<210> SEQ ID NO 182
<211> LENGTH: 21
<212> TYPE: DNA
<213> ORGANISM: Homo sapiens

<400> SEQUENCE: 182
cacagctttc catgacgagt t                                            21

<210> SEQ ID NO 183
<211> LENGTH: 25
<212> TYPE: DNA
<213> ORGANISM: Homo sapiens

<400> SEQUENCE: 183
ttgattgaac aaaacagaaa gatca                                        25

<210> SEQ ID NO 184
<211> LENGTH: 22
<212> TYPE: DNA
<213> ORGANISM: Homo sapiens

<400> SEQUENCE: 184
tgacgagtta caagaggagc aa                                           22

<210> SEQ ID NO 185
<211> LENGTH: 20
<212> TYPE: DNA
<213> ORGANISM: Homo sapiens

<400> SEQUENCE: 185
ctgctcatag cagccacctt                                              20
```

```
<210> SEQ ID NO 186
<211> LENGTH: 20
<212> TYPE: DNA
<213> ORGANISM: Homo sapiens

<400> SEQUENCE: 186
aggtgactgg ggcattgatt                                              20

<210> SEQ ID NO 187
<211> LENGTH: 20
<212> TYPE: DNA
<213> ORGANISM: Homo sapiens

<400> SEQUENCE: 187
acgtggagga ggacacagac                                              20

<210> SEQ ID NO 188
<211> LENGTH: 20
<212> TYPE: DNA
<213> ORGANISM: Homo sapiens

<400> SEQUENCE: 188
ggagccttca gggctacttc                                              20

<210> SEQ ID NO 189
<211> LENGTH: 19
<212> TYPE: DNA
<213> ORGANISM: Homo sapiens

<400> SEQUENCE: 189
agcactgcca aagtggatg                                               19

<210> SEQ ID NO 190
<211> LENGTH: 21
<212> TYPE: DNA
<213> ORGANISM: Homo sapiens

<400> SEQUENCE: 190
ttgttgacat ggaacaagac c                                            21

<210> SEQ ID NO 191
<211> LENGTH: 20
<212> TYPE: DNA
<213> ORGANISM: Homo sapiens

<400> SEQUENCE: 191
gtgggctaca tcagggtacg                                              20

<210> SEQ ID NO 192
<211> LENGTH: 20
<212> TYPE: DNA
<213> ORGANISM: Homo sapiens

<400> SEQUENCE: 192
cagagtcagc caccaactca                                              20

<210> SEQ ID NO 193
<211> LENGTH: 20
<212> TYPE: DNA
<213> ORGANISM: Homo sapiens

<400> SEQUENCE: 193
catcatctgg tccaacctca                                              20
```

```
<210> SEQ ID NO 194
<211> LENGTH: 20
<212> TYPE: DNA
<213> ORGANISM: Homo sapiens

<400> SEQUENCE: 194
gtcctcaggg atggtgtcat                                               20

<210> SEQ ID NO 195
<211> LENGTH: 20
<212> TYPE: DNA
<213> ORGANISM: Homo sapiens

<400> SEQUENCE: 195
tgacctcaag atgtgccact                                               20

<210> SEQ ID NO 196
<211> LENGTH: 20
<212> TYPE: DNA
<213> ORGANISM: Homo sapiens

<400> SEQUENCE: 196
tggttggggt caatccagta                                               20

<210> SEQ ID NO 197
<211> LENGTH: 22
<212> TYPE: DNA
<213> ORGANISM: Homo sapiens

<400> SEQUENCE: 197
gatggattcc agttcgagta tg                                            22

<210> SEQ ID NO 198
<211> LENGTH: 18
<212> TYPE: DNA
<213> ORGANISM: Homo sapiens

<400> SEQUENCE: 198
atcaggcgca ggaaggtc                                                 18

<210> SEQ ID NO 199
<211> LENGTH: 19
<212> TYPE: DNA
<213> ORGANISM: Homo sapiens

<400> SEQUENCE: 199
cccaaaaaga gcgtcaggt                                                19

<210> SEQ ID NO 200
<211> LENGTH: 21
<212> TYPE: DNA
<213> ORGANISM: Homo sapiens

<400> SEQUENCE: 200
ttgttgacat ggaacaagac c                                             21

<210> SEQ ID NO 201
<211> LENGTH: 20
<212> TYPE: DNA
<213> ORGANISM: Homo sapiens

<400> SEQUENCE: 201
```
cttcctaaca gtccgcccta                                              20

<210> SEQ ID NO 202
<211> LENGTH: 20
<212> TYPE: DNA
<213> ORGANISM: Homo sapiens

<400> SEQUENCE: 202
cccgatcagc acagtgattt                                              20

<210> SEQ ID NO 203
<211> LENGTH: 20
<212> TYPE: DNA
<213> ORGANISM: Homo sapiens

<400> SEQUENCE: 203
ctgcttcagg gagacacacc                                              20

<210> SEQ ID NO 204
<211> LENGTH: 19
<212> TYPE: DNA
<213> ORGANISM: Homo sapiens

<400> SEQUENCE: 204
tggcttgcaa cttcctcac                                               19

<210> SEQ ID NO 205
<211> LENGTH: 20
<212> TYPE: DNA
<213> ORGANISM: Homo sapiens

<400> SEQUENCE: 205
aggaagttgc aagccaacaa                                              20

<210> SEQ ID NO 206
<211> LENGTH: 21
<212> TYPE: DNA
<213> ORGANISM: Homo sapiens

<400> SEQUENCE: 206
cgaccttccc ttaatcgtct t                                            21

<210> SEQ ID NO 207
<211> LENGTH: 19
<212> TYPE: DNA
<213> ORGANISM: Homo sapiens

<400> SEQUENCE: 207
gcggaggaaa actgtctgg                                               19

<210> SEQ ID NO 208
<211> LENGTH: 20
<212> TYPE: DNA
<213> ORGANISM: Homo sapiens

<400> SEQUENCE: 208
aaatctgagc agcaccctgt                                              20

<210> SEQ ID NO 209
<211> LENGTH: 20
<212> TYPE: DNA
<213> ORGANISM: Homo sapiens

<400> SEQUENCE: 209

-continued

```
atattcctgg gaatggcaca                                              20

<210> SEQ ID NO 210
<211> LENGTH: 23
<212> TYPE: DNA
<213> ORGANISM: Homo sapiens

<400> SEQUENCE: 210
ccatactgtg gtaatgttga tga                                          23

<210> SEQ ID NO 211
<211> LENGTH: 21
<212> TYPE: DNA
<213> ORGANISM: Homo sapiens

<400> SEQUENCE: 211
tgtcaacaac acagagggag a                                            21

<210> SEQ ID NO 212
<211> LENGTH: 20
<212> TYPE: DNA
<213> ORGANISM: Homo sapiens

<400> SEQUENCE: 212
cacgtagttg ctggggatgt                                              20

<210> SEQ ID NO 213
<211> LENGTH: 19
<212> TYPE: DNA
<213> ORGANISM: Homo sapiens

<400> SEQUENCE: 213
tggcaagatc accagacgg                                               19

<210> SEQ ID NO 214
<211> LENGTH: 20
<212> TYPE: DNA
<213> ORGANISM: Homo sapiens

<400> SEQUENCE: 214
ggcacctttc gtggtctcac                                              20

<210> SEQ ID NO 215
<211> LENGTH: 20
<212> TYPE: DNA
<213> ORGANISM: Homo sapiens

<400> SEQUENCE: 215
catgtcgtct tggctcactc                                              20

<210> SEQ ID NO 216
<211> LENGTH: 21
<212> TYPE: DNA
<213> ORGANISM: Homo sapiens

<400> SEQUENCE: 216
aaattctggc cccaacaata c                                            21

<210> SEQ ID NO 217
<211> LENGTH: 20
<212> TYPE: DNA
<213> ORGANISM: Homo sapiens
```

<400> SEQUENCE: 217
catgtcgtct tggctcactc					20

<210> SEQ ID NO 218
<211> LENGTH: 21
<212> TYPE: DNA
<213> ORGANISM: Homo sapiens

<400> SEQUENCE: 218
aaattctggc cccaacaata c					21

<210> SEQ ID NO 219
<211> LENGTH: 18
<212> TYPE: DNA
<213> ORGANISM: Homo sapiens

<400> SEQUENCE: 219
aggagccagc gtctaggg					18

<210> SEQ ID NO 220
<211> LENGTH: 19
<212> TYPE: DNA
<213> ORGANISM: Homo sapiens

<400> SEQUENCE: 220
ctgcccatca tcatgacct					19

<210> SEQ ID NO 221
<211> LENGTH: 20
<212> TYPE: DNA
<213> ORGANISM: Homo sapiens

<400> SEQUENCE: 221
aacgcaccga atagttacgg					20

<210> SEQ ID NO 222
<211> LENGTH: 20
<212> TYPE: DNA
<213> ORGANISM: Homo sapiens

<400> SEQUENCE: 222
catcatcatg acctggatcg					20

<210> SEQ ID NO 223
<211> LENGTH: 20
<212> TYPE: DNA
<213> ORGANISM: Homo sapiens

<400> SEQUENCE: 223
cactgttacg attcccctga					20

<210> SEQ ID NO 224
<211> LENGTH: 20
<212> TYPE: DNA
<213> ORGANISM: Homo sapiens

<400> SEQUENCE: 224
cggctttctc atcaggtttc					20

<210> SEQ ID NO 225
<211> LENGTH: 20
<212> TYPE: DNA
<213> ORGANISM: Homo sapiens -continued

```
<400> SEQUENCE: 225
attagacggc ctcctgcatc                                               20

<210> SEQ ID NO 226
<211> LENGTH: 20
<212> TYPE: DNA
<213> ORGANISM: Homo sapiens

<400> SEQUENCE: 226
agaccagccc ctcttcatct                                               20

<210> SEQ ID NO 227
<211> LENGTH: 19
<212> TYPE: DNA
<213> ORGANISM: Homo sapiens

<400> SEQUENCE: 227
ggccccggga attatatct                                                19

<210> SEQ ID NO 228
<211> LENGTH: 20
<212> TYPE: DNA
<213> ORGANISM: Homo sapiens

<400> SEQUENCE: 228
ccacttcata gtgggggttc                                               20

<210> SEQ ID NO 229
<211> LENGTH: 19
<212> TYPE: DNA
<213> ORGANISM: Homo sapiens

<400> SEQUENCE: 229
ctgcacaact gccacacag                                                19

<210> SEQ ID NO 230
<211> LENGTH: 20
<212> TYPE: DNA
<213> ORGANISM: Homo sapiens

<400> SEQUENCE: 230
gttctgcatt ggctgggtat                                               20

<210> SEQ ID NO 231
<211> LENGTH: 19
<212> TYPE: DNA
<213> ORGANISM: Homo sapiens

<400> SEQUENCE: 231
cgtggcaagt gagggttc                                                 19

<210> SEQ ID NO 232
<211> LENGTH: 21
<212> TYPE: DNA
<213> ORGANISM: Homo sapiens

<400> SEQUENCE: 232
cgaagactcg gaatgagagg g                                             21

<210> SEQ ID NO 233
<211> LENGTH: 18
<212> TYPE: DNA
```

```
<213> ORGANISM: Homo sapiens

<400> SEQUENCE: 233
gaggcttcct gctctggt                                                 18

<210> SEQ ID NO 234
<211> LENGTH: 19
<212> TYPE: DNA
<213> ORGANISM: Homo sapiens

<400> SEQUENCE: 234
cgcaaaattg gtgctcagt                                                19

<210> SEQ ID NO 235
<211> LENGTH: 20
<212> TYPE: DNA
<213> ORGANISM: Homo sapiens

<400> SEQUENCE: 235
gtccgggact tcctaacaga                                               20

<210> SEQ ID NO 236
<211> LENGTH: 20
<212> TYPE: DNA
<213> ORGANISM: Homo sapiens

<400> SEQUENCE: 236
gctgacctcc tggatagtgg                                               20

<210> SEQ ID NO 237
<211> LENGTH: 20
<212> TYPE: DNA
<213> ORGANISM: Homo sapiens

<400> SEQUENCE: 237
gtggtcagca cccagcttat                                               20

<210> SEQ ID NO 238
<211> LENGTH: 19
<212> TYPE: DNA
<213> ORGANISM: Homo sapiens

<400> SEQUENCE: 238
ccaaggcctg cttcttgac                                                19

<210> SEQ ID NO 239
<211> LENGTH: 20
<212> TYPE: DNA
<213> ORGANISM: Homo sapiens

<400> SEQUENCE: 239
gctgtggtcc ttgcatctct                                               20

<210> SEQ ID NO 240
<211> LENGTH: 20
<212> TYPE: DNA
<213> ORGANISM: Homo sapiens

<400> SEQUENCE: 240
gcttcataag tctgcgccta                                               20

<210> SEQ ID NO 241
<211> LENGTH: 20
```

```
<212> TYPE: DNA
<213> ORGANISM: Homo sapiens

<400> SEQUENCE: 241
cttccctcag ctttcaggac                                              20

<210> SEQ ID NO 242
<211> LENGTH: 20
<212> TYPE: DNA
<213> ORGANISM: Homo sapiens

<400> SEQUENCE: 242
tctggggtcc tagggaattg                                              20

<210> SEQ ID NO 243
<211> LENGTH: 20
<212> TYPE: DNA
<213> ORGANISM: Homo sapiens

<400> SEQUENCE: 243
acctcaagat gtccctcagc                                              20

<210> SEQ ID NO 244
<211> LENGTH: 19
<212> TYPE: DNA
<213> ORGANISM: Homo sapiens

<400> SEQUENCE: 244
caggagggtc ctgtacgtg                                               19

<210> SEQ ID NO 245
<211> LENGTH: 20
<212> TYPE: DNA
<213> ORGANISM: Homo sapiens

<400> SEQUENCE: 245
gagaccttcg gcgagtacag                                              20

<210> SEQ ID NO 246
<211> LENGTH: 20
<212> TYPE: DNA
<213> ORGANISM: Homo sapiens

<400> SEQUENCE: 246
aaaggccttc tcctcgttgt                                              20

<210> SEQ ID NO 247
<211> LENGTH: 20
<212> TYPE: DNA
<213> ORGANISM: Homo sapiens

<400> SEQUENCE: 247
ggcggcaaat actcagtgaa                                              20

<210> SEQ ID NO 248
<211> LENGTH: 20
<212> TYPE: DNA
<213> ORGANISM: Homo sapiens

<400> SEQUENCE: 248
cctgggtgtc ctccttatcc                                              20

<210> SEQ ID NO 249
```

```
<211> LENGTH: 20
<212> TYPE: DNA
<213> ORGANISM: Homo sapiens

<400> SEQUENCE: 249
cggatactca cgccagaagt                                              20

<210> SEQ ID NO 250
<211> LENGTH: 20
<212> TYPE: DNA
<213> ORGANISM: Homo sapiens

<400> SEQUENCE: 250
agagatacgc aggtgcaggt                                              20

<210> SEQ ID NO 251
<211> LENGTH: 20
<212> TYPE: DNA
<213> ORGANISM: Homo sapiens

<400> SEQUENCE: 251
aagattcgaa caccgacctc                                              20

<210> SEQ ID NO 252
<211> LENGTH: 20
<212> TYPE: DNA
<213> ORGANISM: Homo sapiens

<400> SEQUENCE: 252
gcacttctgg cgtgagtatc                                              20

<210> SEQ ID NO 253
<211> LENGTH: 18
<212> TYPE: DNA
<213> ORGANISM: Homo sapiens

<400> SEQUENCE: 253
cacgcctgga acaaggac                                                18

<210> SEQ ID NO 254
<211> LENGTH: 20
<212> TYPE: DNA
<213> ORGANISM: Homo sapiens

<400> SEQUENCE: 254
atgcacctca tggttgttgg                                              20

<210> SEQ ID NO 255
<211> LENGTH: 19
<212> TYPE: DNA
<213> ORGANISM: Homo sapiens

<400> SEQUENCE: 255
caggtgacag gcatcgact                                               19

<210> SEQ ID NO 256
<211> LENGTH: 20
<212> TYPE: DNA
<213> ORGANISM: Homo sapiens

<400> SEQUENCE: 256
cgcaggtcac aatacggtta                                              20
```

```
<210> SEQ ID NO 257
<211> LENGTH: 20
<212> TYPE: DNA
<213> ORGANISM: Homo sapiens

<400> SEQUENCE: 257
tgaggccctg agagagaaga                                                   20

<210> SEQ ID NO 258
<211> LENGTH: 20
<212> TYPE: DNA
<213> ORGANISM: Homo sapiens

<400> SEQUENCE: 258
attccgaaac tccacacgtc                                                   20

<210> SEQ ID NO 259
<211> LENGTH: 20
<212> TYPE: DNA
<213> ORGANISM: Homo sapiens

<400> SEQUENCE: 259
tcaaggaaat tgagcaacga                                                   20

<210> SEQ ID NO 260
<211> LENGTH: 20
<212> TYPE: DNA
<213> ORGANISM: Homo sapiens

<400> SEQUENCE: 260
tctgatttgg gcatttgagc                                                   20

<210> SEQ ID NO 261
<211> LENGTH: 19
<212> TYPE: DNA
<213> ORGANISM: Homo sapiens

<400> SEQUENCE: 261
tatggtcgac ggtccaaat                                                    19

<210> SEQ ID NO 262
<211> LENGTH: 20
<212> TYPE: DNA
<213> ORGANISM: Homo sapiens

<400> SEQUENCE: 262
tcctcaccac tgatgacagc                                                   20

<210> SEQ ID NO 263
<211> LENGTH: 20
<212> TYPE: DNA
<213> ORGANISM: Homo sapiens

<400> SEQUENCE: 263
cactgtgacc cacaaaccag                                                   20

<210> SEQ ID NO 264
<211> LENGTH: 20
<212> TYPE: DNA
<213> ORGANISM: Homo sapiens

<400> SEQUENCE: 264
gcaagtccaa ctgctatgga                                                   20
```

```
<210> SEQ ID NO 265
<211> LENGTH: 20
<212> TYPE: DNA
<213> ORGANISM: Homo sapiens

<400> SEQUENCE: 265
tgaggccctg agagagaaga                                                  20

<210> SEQ ID NO 266
<211> LENGTH: 20
<212> TYPE: DNA
<213> ORGANISM: Homo sapiens

<400> SEQUENCE: 266
attccgaaac tccacacgtc                                                  20

<210> SEQ ID NO 267
<211> LENGTH: 20
<212> TYPE: DNA
<213> ORGANISM: Homo sapiens

<400> SEQUENCE: 267
tctactcctt tgggcgagtg                                                  20

<210> SEQ ID NO 268
<211> LENGTH: 20
<212> TYPE: DNA
<213> ORGANISM: Homo sapiens

<400> SEQUENCE: 268
cgtccttcag gggaattctt                                                  20

<210> SEQ ID NO 269
<211> LENGTH: 20
<212> TYPE: DNA
<213> ORGANISM: Homo sapiens

<400> SEQUENCE: 269
taaggacacc ccaaattcca                                                  20

<210> SEQ ID NO 270
<211> LENGTH: 20
<212> TYPE: DNA
<213> ORGANISM: Homo sapiens

<400> SEQUENCE: 270
gccaagatga tcagccattc                                                  20

<210> SEQ ID NO 271
<211> LENGTH: 21
<212> TYPE: DNA
<213> ORGANISM: Homo sapiens

<400> SEQUENCE: 271
gcagtcaaca gtcgaagaag g                                                21

<210> SEQ ID NO 272
<211> LENGTH: 20
<212> TYPE: DNA
<213> ORGANISM: Homo sapiens

<400> SEQUENCE: 272 agcttttttct tctgcccaca                                                 20
```

```
<210> SEQ ID NO 273
<211> LENGTH: 20
<212> TYPE: DNA
<213> ORGANISM: Homo sapiens

<400> SEQUENCE: 273
agccagcaag cagtgaagtc                                              20

<210> SEQ ID NO 274
<211> LENGTH: 20
<212> TYPE: DNA
<213> ORGANISM: Homo sapiens

<400> SEQUENCE: 274
tcaggtgact caagcagtgg                                              20

<210> SEQ ID NO 275
<211> LENGTH: 20
<212> TYPE: DNA
<213> ORGANISM: Homo sapiens

<400> SEQUENCE: 275
ccgggagtct atggtcaaac                                              20

<210> SEQ ID NO 276
<211> LENGTH: 20
<212> TYPE: DNA
<213> ORGANISM: Homo sapiens

<400> SEQUENCE: 276
cacggcactc agcttacttg                                              20

<210> SEQ ID NO 277
<211> LENGTH: 19
<212> TYPE: DNA
<213> ORGANISM: Homo sapiens

<400> SEQUENCE: 277
tggagcagtc ttcgtttcg                                               19

<210> SEQ ID NO 278
<211> LENGTH: 20
<212> TYPE: DNA
<213> ORGANISM: Homo sapiens

<400> SEQUENCE: 278
ctggctcctc ttctgaatcg                                              20

<210> SEQ ID NO 279
<211> LENGTH: 19
<212> TYPE: DNA
<213> ORGANISM: Homo sapiens

<400> SEQUENCE: 279
gcccgattca gaagaggag                                               19

<210> SEQ ID NO 280
<211> LENGTH: 21
<212> TYPE: DNA
<213> ORGANISM: Homo sapiens

<400> SEQUENCE: 280
```
tcatctctgc agatcacttg g         21

<210> SEQ ID NO 281
<211> LENGTH: 20
<212> TYPE: DNA
<213> ORGANISM: Homo sapiens

<400> SEQUENCE: 281
ccagcagagg cataaggttc           20

<210> SEQ ID NO 282
<211> LENGTH: 20
<212> TYPE: DNA
<213> ORGANISM: Homo sapiens

<400> SEQUENCE: 282
agtagtgcct tcgggactgg           20

<210> SEQ ID NO 283
<211> LENGTH: 24
<212> TYPE: DNA
<213> ORGANISM: Homo sapiens

<400> SEQUENCE: 283
aggctgattc tggaagttct gagg      24

<210> SEQ ID NO 284
<211> LENGTH: 21
<212> TYPE: DNA
<213> ORGANISM: Homo sapiens

<400> SEQUENCE: 284
aatctggact gcttgtggct g         21

<210> SEQ ID NO 285
<211> LENGTH: 19
<212> TYPE: DNA
<213> ORGANISM: Homo sapiens

<400> SEQUENCE: 285
gttgggcctc caggattta            19

<210> SEQ ID NO 286
<211> LENGTH: 20
<212> TYPE: DNA
<213> ORGANISM: Homo sapiens

<400> SEQUENCE: 286
gcctggtagt cctgggaaac           20

<210> SEQ ID NO 287
<211> LENGTH: 20
<212> TYPE: DNA
<213> ORGANISM: Homo sapiens

<400> SEQUENCE: 287
tggatggatt gtgttcctga           20

<210> SEQ ID NO 288
<211> LENGTH: 20
<212> TYPE: DNA
<213> ORGANISM: Homo sapiens

<400> SEQUENCE: 288
gcctgccttc aagatttctg                                               20

<210> SEQ ID NO 289
<211> LENGTH: 21
<212> TYPE: DNA
<213> ORGANISM: Homo sapiens

<400> SEQUENCE: 289
ctgagactgt gctgacctgt g                                             21

<210> SEQ ID NO 290
<211> LENGTH: 20
<212> TYPE: DNA
<213> ORGANISM: Homo sapiens

<400> SEQUENCE: 290
ctcttcatct ccgccttctg                                               20

<210> SEQ ID NO 291
<211> LENGTH: 20
<212> TYPE: DNA
<213> ORGANISM: Homo sapiens

<400> SEQUENCE: 291
gagaccgcct acatcgaaga                                               20

<210> SEQ ID NO 292
<211> LENGTH: 20
<212> TYPE: DNA
<213> ORGANISM: Homo sapiens

<400> SEQUENCE: 292
ggtagcgttc aaacctcctg                                               20

<210> SEQ ID NO 293
<211> LENGTH: 20
<212> TYPE: DNA
<213> ORGANISM: Homo sapiens

<400> SEQUENCE: 293
acaccgtcct caacctgaag                                               20

<210> SEQ ID NO 294
<211> LENGTH: 20
<212> TYPE: DNA
<213> ORGANISM: Homo sapiens

<400> SEQUENCE: 294
aatggccagt gccacatagt                                               20

<210> SEQ ID NO 295
<211> LENGTH: 20
<212> TYPE: DNA
<213> ORGANISM: Homo sapiens

<400> SEQUENCE: 295
ggtgcacttt gtgagcaaga                                               20

<210> SEQ ID NO 296
<211> LENGTH: 20
<212> TYPE: DNA
<213> ORGANISM: Homo sapiens

<400> SEQUENCE: 296
ttggtatgca gatgggttca                                          20

<210> SEQ ID NO 297
<211> LENGTH: 20
<212> TYPE: DNA
<213> ORGANISM: Homo sapiens

<400> SEQUENCE: 297
agctgtggtc caacttctgg                                          20

<210> SEQ ID NO 298
<211> LENGTH: 20
<212> TYPE: DNA
<213> ORGANISM: Homo sapiens

<400> SEQUENCE: 298
gtgtggtaac cgggaaacag                                          20

<210> SEQ ID NO 299
<211> LENGTH: 21
<212> TYPE: DNA
<213> ORGANISM: Homo sapiens

<400> SEQUENCE: 299
ttcagtttgc tgtgtgtttg c                                        21

<210> SEQ ID NO 300
<211> LENGTH: 20
<212> TYPE: DNA
<213> ORGANISM: Homo sapiens

<400> SEQUENCE: 300
ccaccttctg gagaatccaa                                          20

<210> SEQ ID NO 301
<211> LENGTH: 20
<212> TYPE: DNA
<213> ORGANISM: Homo sapiens

<400> SEQUENCE: 301
ggcagtattg acagggagga                                          20

<210> SEQ ID NO 302
<211> LENGTH: 20
<212> TYPE: DNA
<213> ORGANISM: Homo sapiens

<400> SEQUENCE: 302
tactcttgct ggaggctggt                                          20

<210> SEQ ID NO 303
<211> LENGTH: 22
<212> TYPE: DNA
<213> ORGANISM: Homo sapiens

<400> SEQUENCE: 303
gcctattctg tcacttcggc tc                                       22

<210> SEQ ID NO 304
<211> LENGTH: 22
<212> TYPE: DNA
<213> ORGANISM: Homo sapiens

<400> SEQUENCE: 304
gcaggcacag gtcttgatga ac                                    22

<210> SEQ ID NO 305
<211> LENGTH: 20
<212> TYPE: DNA
<213> ORGANISM: Homo sapiens

<400> SEQUENCE: 305
gacctctggg aggtgttcag                                       20

<210> SEQ ID NO 306
<211> LENGTH: 20
<212> TYPE: DNA
<213> ORGANISM: Homo sapiens

<400> SEQUENCE: 306
ttagggatcg acgaaggaga                                       20

<210> SEQ ID NO 307
<211> LENGTH: 20
<212> TYPE: DNA
<213> ORGANISM: Homo sapiens

<400> SEQUENCE: 307
attcctgcca tcaaccagac                                       20

<210> SEQ ID NO 308
<211> LENGTH: 20
<212> TYPE: DNA
<213> ORGANISM: Homo sapiens

<400> SEQUENCE: 308
cctgcttctt ggcttcattc                                       20

<210> SEQ ID NO 309
<211> LENGTH: 20
<212> TYPE: DNA
<213> ORGANISM: Homo sapiens

<400> SEQUENCE: 309
caaagggaca tcccaaaatg                                       20

<210> SEQ ID NO 310
<211> LENGTH: 22
<212> TYPE: DNA
<213> ORGANISM: Homo sapiens

<400> SEQUENCE: 310
gagtcagcca tgattttctt cc                                    22

<210> SEQ ID NO 311
<211> LENGTH: 20
<212> TYPE: DNA
<213> ORGANISM: Homo sapiens

<400> SEQUENCE: 311
taccccgagt acttccagca                                       20

<210> SEQ ID NO 312
<211> LENGTH: 20
<212> TYPE: DNA

<213> ORGANISM: Homo sapiens

<400> SEQUENCE: 312
gatctgcttc caggtcttgc                                              20

<210> SEQ ID NO 313
<211> LENGTH: 20
<212> TYPE: DNA
<213> ORGANISM: Homo sapiens

<400> SEQUENCE: 313
cacacagaca gccactcacc                                              20

<210> SEQ ID NO 314
<211> LENGTH: 20
<212> TYPE: DNA
<213> ORGANISM: Homo sapiens

<400> SEQUENCE: 314 cagggtggt tattgcatct                                               20

<210> SEQ ID NO 315
<211> LENGTH: 20
<212> TYPE: DNA
<213> ORGANISM: Homo sapiens

<400> SEQUENCE: 315
cagaccccaa ctatgtgcaa                                              20

<210> SEQ ID NO 316
<211> LENGTH: 21
<212> TYPE: DNA
<213> ORGANISM: Homo sapiens

<400> SEQUENCE: 316
cgcattgtag gtgtcatagc a                                            21

<210> SEQ ID NO 317
<211> LENGTH: 19
<212> TYPE: DNA
<213> ORGANISM: Homo sapiens

<400> SEQUENCE: 317
ctctcttggc agccttcct                                               19

<210> SEQ ID NO 318
<211> LENGTH: 21
<212> TYPE: DNA
<213> ORGANISM: Homo sapiens

<400> SEQUENCE: 318
tgaattctca gccctcttca a                                            21

<210> SEQ ID NO 319
<211> LENGTH: 20
<212> TYPE: DNA
<213> ORGANISM: Homo sapiens

<400> SEQUENCE: 319
tcgccttagt cgtcaccctt                                              20

<210> SEQ ID NO 320
<211> LENGTH: 23

<212> TYPE: DNA
<213> ORGANISM: Homo sapiens

<400> SEQUENCE: 320
tgtttctcgt caactccacc tcg                                          23

<210> SEQ ID NO 321
<211> LENGTH: 20
<212> TYPE: DNA
<213> ORGANISM: Homo sapiens

<400> SEQUENCE: 321
ctgatttcat cggggttgtc                                              20

<210> SEQ ID NO 322
<211> LENGTH: 20
<212> TYPE: DNA
<213> ORGANISM: Homo sapiens

<400> SEQUENCE: 322
tgccttgctg aatgaacttg                                              20

<210> SEQ ID NO 323
<211> LENGTH: 19
<212> TYPE: DNA
<213> ORGANISM: Homo sapiens

<400> SEQUENCE: 323
ccagtgaaac agccaccac                                               19

<210> SEQ ID NO 324
<211> LENGTH: 20
<212> TYPE: DNA
<213> ORGANISM: Homo sapiens

<400> SEQUENCE: 324
ctccttccag tgttccaagg                                              20

<210> SEQ ID NO 325
<211> LENGTH: 20
<212> TYPE: DNA
<213> ORGANISM: Homo sapiens

<400> SEQUENCE: 325
ggactctgtc acacccacct                                              20

<210> SEQ ID NO 326
<211> LENGTH: 20
<212> TYPE: DNA
<213> ORGANISM: Homo sapiens

<400> SEQUENCE: 326
cagggtctca gggaggtctt                                              20

<210> SEQ ID NO 327
<211> LENGTH: 21
<212> TYPE: DNA
<213> ORGANISM: Homo sapiens

<400> SEQUENCE: 327
tgccagagct gagatgttgt t                                            21

<210> SEQ ID NO 328

```
<210> SEQ ID NO 328
<211> LENGTH: 20
<212> TYPE: DNA
<213> ORGANISM: Homo sapiens

<400> SEQUENCE: 328
tgtagcattt cggctttcct                                              20

<210> SEQ ID NO 329
<211> LENGTH: 20
<212> TYPE: DNA
<213> ORGANISM: Homo sapiens

<400> SEQUENCE: 329
ggcaagtact gcgagtgtga                                              20

<210> SEQ ID NO 330
<211> LENGTH: 20
<212> TYPE: DNA
<213> ORGANISM: Homo sapiens

<400> SEQUENCE: 330
attcttttcg gtcgtggatg                                              20

<210> SEQ ID NO 331
<211> LENGTH: 19
<212> TYPE: DNA
<213> ORGANISM: Homo sapiens

<400> SEQUENCE: 331
cactgctgct cctgctcct                                               19

<210> SEQ ID NO 332
<211> LENGTH: 21
<212> TYPE: DNA
<213> ORGANISM: Homo sapiens

<400> SEQUENCE: 332
tgttcagcat cttttcgatg a                                            21

<210> SEQ ID NO 333
<211> LENGTH: 21
<212> TYPE: DNA
<213> ORGANISM: Homo sapiens

<400> SEQUENCE: 333
tgacaatgac aacatcccag a                                            21

<210> SEQ ID NO 334
<211> LENGTH: 20
<212> TYPE: DNA
<213> ORGANISM: Homo sapiens

<400> SEQUENCE: 334
tgagtctgcc atgacctgtt                                              20

<210> SEQ ID NO 335
<211> LENGTH: 21
<212> TYPE: DNA
<213> ORGANISM: Homo sapiens

<400> SEQUENCE: 335
ccctgctcta cacagaacca g                                            21
```

```
<210> SEQ ID NO 336
<211> LENGTH: 19
<212> TYPE: DNA
<213> ORGANISM: Homo sapiens

<400> SEQUENCE: 336
acacctggct cccctttct                                                19

<210> SEQ ID NO 337
<211> LENGTH: 24
<212> TYPE: DNA
<213> ORGANISM: Homo sapiens

<400> SEQUENCE: 337
gcctggatct tctttctcct ttgc                                          24

<210> SEQ ID NO 338
<211> LENGTH: 22
<212> TYPE: DNA
<213> ORGANISM: Homo sapiens

<400> SEQUENCE: 338
catccagggc gatgtacttg tc                                            22

<210> SEQ ID NO 339
<211> LENGTH: 20
<212> TYPE: DNA
<213> ORGANISM: Homo sapiens

<400> SEQUENCE: 339
ccccctctga gtcaggaaac                                               20

<210> SEQ ID NO 340
<211> LENGTH: 20
<212> TYPE: DNA
<213> ORGANISM: Homo sapiens

<400> SEQUENCE: 340
tcatgtgctg tgactgcttg                                               20

<210> SEQ ID NO 341
<211> LENGTH: 22
<212> TYPE: DNA
<213> ORGANISM: Homo sapiens

<400> SEQUENCE: 341
tggacccacc aagattctcc tg                                            22

<210> SEQ ID NO 342
<211> LENGTH: 22
<212> TYPE: DNA
<213> ORGANISM: Homo sapiens

<400> SEQUENCE: 342
gaccacagct ttccatgacg ag                                            22

<210> SEQ ID NO 343
<211> LENGTH: 20
<212> TYPE: DNA
<213> ORGANISM: Homo sapiens

<400> SEQUENCE: 343
tctgtgcctg ctgctcatag                                               20
```

```
<210> SEQ ID NO 344
<211> LENGTH: 20
<212> TYPE: DNA
<213> ORGANISM: Homo sapiens

<400> SEQUENCE: 344
gagtttgggt ttgcttgtcc                                        20

<210> SEQ ID NO 345
<211> LENGTH: 18
<212> TYPE: DNA
<213> ORGANISM: Homo sapiens

<400> SEQUENCE: 345
cgagaagtgc ccaggaag                                          18

<210> SEQ ID NO 346
<211> LENGTH: 20
<212> TYPE: DNA
<213> ORGANISM: Homo sapiens

<400> SEQUENCE: 346
agtgagaagc caggaaagca                                        20

<210> SEQ ID NO 347
<211> LENGTH: 20
<212> TYPE: DNA
<213> ORGANISM: Homo sapiens

<400> SEQUENCE: 347
tggaaatatc acccacagca                                        20

<210> SEQ ID NO 348
<211> LENGTH: 20
<212> TYPE: DNA
<213> ORGANISM: Homo sapiens

<400> SEQUENCE: 348
aggcattttt gcttcacacc                                        20

<210> SEQ ID NO 349
<211> LENGTH: 20
<212> TYPE: DNA
<213> ORGANISM: Homo sapiens

<400> SEQUENCE: 349
gctccagctt ctacgtggtc                                        20

<210> SEQ ID NO 350
<211> LENGTH: 21
<212> TYPE: DNA
<213> ORGANISM: Homo sapiens

<400> SEQUENCE: 350
ttaattatcg aagcggtcga a                                      21

<210> SEQ ID NO 351
<211> LENGTH: 20
<212> TYPE: DNA
<213> ORGANISM: Homo sapiens

<400> SEQUENCE: 351
agccagcaga tcgagaacat                                        20
```

<210> SEQ ID NO 352
<211> LENGTH: 20
<212> TYPE: DNA
<213> ORGANISM: Homo sapiens

<400> SEQUENCE: 352
ccttcttgag gttgccagtc                                            20

<210> SEQ ID NO 353
<211> LENGTH: 20
<212> TYPE: DNA
<213> ORGANISM: Homo sapiens

<400> SEQUENCE: 353
caccaatcac cccattaacc                                            20

<210> SEQ ID NO 354
<211> LENGTH: 20
<212> TYPE: DNA
<213> ORGANISM: Homo sapiens

<400> SEQUENCE: 354
gcttgagctg agcttttttcc                                           20

<210> SEQ ID NO 355
<211> LENGTH: 20
<212> TYPE: DNA
<213> ORGANISM: Homo sapiens

<400> SEQUENCE: 355
ccaggtgctg gaaaaagaag                                            20

<210> SEQ ID NO 356
<211> LENGTH: 20
<212> TYPE: DNA
<213> ORGANISM: Homo sapiens

<400> SEQUENCE: 356
gagctgctct gcctgagtct                                            20

<210> SEQ ID NO 357
<211> LENGTH: 20
<212> TYPE: DNA
<213> ORGANISM: Homo sapiens

<400> SEQUENCE: 357
gcagacacac ctgttggaaa                                            20

<210> SEQ ID NO 358
<211> LENGTH: 20
<212> TYPE: DNA
<213> ORGANISM: Homo sapiens

<400> SEQUENCE: 358
gaacgacctt cccttaatcg                                            20

<210> SEQ ID NO 359
<211> LENGTH: 22
<212> TYPE: DNA
<213> ORGANISM: Homo sapiens

<400> SEQUENCE: 359
cctactacat ccaggcgtcc ac                                          22

<210> SEQ ID NO 360
<211> LENGTH: 21
<212> TYPE: DNA
<213> ORGANISM: Homo sapiens

<400> SEQUENCE: 360
atgcaaatcg cctgtggtag c                                           21

<210> SEQ ID NO 361
<211> LENGTH: 20
<212> TYPE: DNA
<213> ORGANISM: Homo sapiens

<400> SEQUENCE: 361
ctgttcggag gcttcaactc                                             20

<210> SEQ ID NO 362
<211> LENGTH: 18
<212> TYPE: DNA
<213> ORGANISM: Homo sapiens

<400> SEQUENCE: 362
agggatctcc caggcatc                                               18

<210> SEQ ID NO 363
<211> LENGTH: 20
<212> TYPE: DNA
<213> ORGANISM: Homo sapiens

<400> SEQUENCE: 363
tacctgggat cacctccatc                                             20

<210> SEQ ID NO 364
<211> LENGTH: 20
<212> TYPE: DNA
<213> ORGANISM: Homo sapiens

<400> SEQUENCE: 364
acagggatcc tcagtgtcgt                                             20

<210> SEQ ID NO 365
<211> LENGTH: 19
<212> TYPE: DNA
<213> ORGANISM: Homo sapiens

<400> SEQUENCE: 365
cgggatgagt tgggaggag                                              19

<210> SEQ ID NO 366
<211> LENGTH: 20
<212> TYPE: DNA
<213> ORGANISM: Homo sapiens

<400> SEQUENCE: 366
ttagggcttc ctcttggaga                                             20

<210> SEQ ID NO 367
<211> LENGTH: 18
<212> TYPE: DNA
<213> ORGANISM: Homo sapiens

<400> SEQUENCE: 367
atggtgcgca ggttcttg                                              18

<210> SEQ ID NO 368
<211> LENGTH: 18
<212> TYPE: DNA
<213> ORGANISM: Homo sapiens

<400> SEQUENCE: 368
accagcgtgt ccaggaag                                              18

<210> SEQ ID NO 369
<211> LENGTH: 18
<212> TYPE: DNA
<213> ORGANISM: Homo sapiens

<400> SEQUENCE: 369
gagcagcatg gagccttc                                              18

<210> SEQ ID NO 370
<211> LENGTH: 20
<212> TYPE: DNA
<213> ORGANISM: Homo sapiens

<400> SEQUENCE: 370
gcatggttac tgcctctggt                                            20

<210> SEQ ID NO 371
<211> LENGTH: 20
<212> TYPE: DNA
<213> ORGANISM: Homo sapiens

<400> SEQUENCE: 371
caaacagaca aggctggtga                                            20

<210> SEQ ID NO 372
<211> LENGTH: 22
<212> TYPE: DNA
<213> ORGANISM: Homo sapiens

<400> SEQUENCE: 372
tcaatctcat ctggattttt gg                                         22

<210> SEQ ID NO 373
<211> LENGTH: 20
<212> TYPE: DNA
<213> ORGANISM: Homo sapiens

<400> SEQUENCE: 373
ctgcaggtgg acaacagaaa                                            20

<210> SEQ ID NO 374
<211> LENGTH: 20
<212> TYPE: DNA
<213> ORGANISM: Homo sapiens

<400> SEQUENCE: 374
catcagccag aatcccatct                                            20

<210> SEQ ID NO 375
<211> LENGTH: 20
<212> TYPE: DNA
<213> ORGANISM: Homo sapiens

<400> SEQUENCE: 375
gtccccagag agacctgttt         20

<210> SEQ ID NO 376
<211> LENGTH: 19
<212> TYPE: DNA
<213> ORGANISM: Homo sapiens

<400> SEQUENCE: 376
agacacaatt ggcgcaggt          19

<210> SEQ ID NO 377
<211> LENGTH: 20
<212> TYPE: DNA
<213> ORGANISM: Homo sapiens

<400> SEQUENCE: 377
aagactggac gcgatagctg         20

<210> SEQ ID NO 378
<211> LENGTH: 20
<212> TYPE: DNA
<213> ORGANISM: Homo sapiens

<400> SEQUENCE: 378
ggttgttcct gagacgctgt         20

<210> SEQ ID NO 379
<211> LENGTH: 20
<212> TYPE: DNA
<213> ORGANISM: Homo sapiens

<400> SEQUENCE: 379
tacaccagac ccgtgttcct         20

<210> SEQ ID NO 380
<211> LENGTH: 22
<212> TYPE: DNA
<213> ORGANISM: Homo sapiens

<400> SEQUENCE: 380
tccaggtcaa acttctcgaa gg      22

<210> SEQ ID NO 381
<211> LENGTH: 18
<212> TYPE: DNA
<213> ORGANISM: Homo sapiens

<400> SEQUENCE: 381
cttcaatgcc cagctcca           18

<210> SEQ ID NO 382
<211> LENGTH: 20
<212> TYPE: DNA
<213> ORGANISM: Homo sapiens

<400> SEQUENCE: 382
ttcccaacca catcttccac         20

<210> SEQ ID NO 383
<211> LENGTH: 18
<212> TYPE: DNA
<213> ORGANISM: Homo sapiens -continued

```
<400> SEQUENCE: 383
ctgctgctct tgggcact                                                   18

<210> SEQ ID NO 384
<211> LENGTH: 20
<212> TYPE: DNA
<213> ORGANISM: Homo sapiens

<400> SEQUENCE: 384
cagcagtcaa aggggatgac                                                 20

<210> SEQ ID NO 385
<211> LENGTH: 21
<212> TYPE: DNA
<213> ORGANISM: Homo sapiens

<400> SEQUENCE: 385
aggattccta tgtgggcgac g                                               21

<210> SEQ ID NO 386
<211> LENGTH: 21
<212> TYPE: DNA
<213> ORGANISM: Homo sapiens

<400> SEQUENCE: 386
tcaggcagct cgtagctctt c                                               21

<210> SEQ ID NO 387
<211> LENGTH: 23
<212> TYPE: DNA
<213> ORGANISM: Homo sapiens

<400> SEQUENCE: 387
ggaatgtggg ctttgtgttc acc                                             23

<210> SEQ ID NO 388
<211> LENGTH: 21
<212> TYPE: DNA
<213> ORGANISM: Homo sapiens

<400> SEQUENCE: 388
aggccaggac tcgtttgtac c                                               21

<210> SEQ ID NO 389
<211> LENGTH: 21
<212> TYPE: DNA
<213> ORGANISM: Homo sapiens

<400> SEQUENCE: 389
acatcaaggg catcgtcaag g                                               21

<210> SEQ ID NO 390
<211> LENGTH: 24
<212> TYPE: DNA
<213> ORGANISM: Homo sapiens

<400> SEQUENCE: 390
tctctttctc ctgcacagtc ttgg                                            24

<210> SEQ ID NO 391
<211> LENGTH: 22
<212> TYPE: DNA
```

```
<213> ORGANISM: Homo sapiens

<400> SEQUENCE: 391
tgctcgcgct actctctctt tc                                           22

<210> SEQ ID NO 392
<211> LENGTH: 20
<212> TYPE: DNA
<213> ORGANISM: Homo sapiens

<400> SEQUENCE: 392
tcacatggtt cacacggcag                                              20

<210> SEQ ID NO 393
<211> LENGTH: 20
<212> TYPE: DNA
<213> ORGANISM: Homo sapiens

<400> SEQUENCE: 393
tggccttctc tctggaaatg                                              20

<210> SEQ ID NO 394
<211> LENGTH: 20
<212> TYPE: DNA
<213> ORGANISM: Homo sapiens

<400> SEQUENCE: 394
tcatttcctc ctcgtggttc                                              20

<210> SEQ ID NO 395
<211> LENGTH: 20
<212> TYPE: DNA
<213> ORGANISM: Homo sapiens

<400> SEQUENCE: 395
aggtgaccat gcagaacctc                                              20

<210> SEQ ID NO 396
<211> LENGTH: 20
<212> TYPE: DNA
<213> ORGANISM: Homo sapiens

<400> SEQUENCE: 396
cctcgtggtt cttcttcagg                                              20

<210> SEQ ID NO 397
<211> LENGTH: 20
<212> TYPE: DNA
<213> ORGANISM: Homo sapiens

<400> SEQUENCE: 397
gaaatcttgg gcttgatgga                                              20

<210> SEQ ID NO 398
<211> LENGTH: 20
<212> TYPE: DNA
<213> ORGANISM: Homo sapiens

<400> SEQUENCE: 398
ccgaggttgt tgttgaaggt                                              20

<210> SEQ ID NO 399
<211> LENGTH: 20
```

```
<212> TYPE: DNA
<213> ORGANISM: Homo sapiens

<400> SEQUENCE: 399
ccatggataa agctgccaat                                               20

<210> SEQ ID NO 400
<211> LENGTH: 20
<212> TYPE: DNA
<213> ORGANISM: Homo sapiens

<400> SEQUENCE: 400
gacacagcaa gctcacaagc                                               20

<210> SEQ ID NO 401
<211> LENGTH: 20
<212> TYPE: DNA
<213> ORGANISM: Homo sapiens

<400> SEQUENCE: 401
cactcttaca ccacggctga                                               20

<210> SEQ ID NO 402
<211> LENGTH: 20
<212> TYPE: DNA
<213> ORGANISM: Homo sapiens

<400> SEQUENCE: 402
cataagcagg tggagcattg                                               20

<210> SEQ ID NO 403
<211> LENGTH: 22
<212> TYPE: DNA
<213> ORGANISM: Homo sapiens

<400> SEQUENCE: 403
ttgtccaggg tattgaaagt gc                                            22

<210> SEQ ID NO 404
<211> LENGTH: 21
<212> TYPE: DNA
<213> ORGANISM: Homo sapiens

<400> SEQUENCE: 404
gacaagagca gaagatgcgg g                                             21

<210> SEQ ID NO 405
<211> LENGTH: 21
<212> TYPE: DNA
<213> ORGANISM: Homo sapiens

<400> SEQUENCE: 405
gcgttggaac agaggttgga g                                             21

<210> SEQ ID NO 406
<211> LENGTH: 22
<212> TYPE: DNA
<213> ORGANISM: Homo sapiens

<400> SEQUENCE: 406
caggtgtctc aagggtagca gg                                            22

<210> SEQ ID NO 407
```

```
<211> LENGTH: 21
<212> TYPE: DNA
<213> ORGANISM: Homo sapiens

<400> SEQUENCE: 407 cttcccttc gccacagtat g                                              21

<210> SEQ ID NO 408
<211> LENGTH: 22
<212> TYPE: DNA
<213> ORGANISM: Homo sapiens

<400> SEQUENCE: 408
cctccttctc cttcttgcca ct                                            22

<210> SEQ ID NO 409
<211> LENGTH: 22
<212> TYPE: DNA
<213> ORGANISM: Homo sapiens

<400> SEQUENCE: 409
aatggctctc agatgctcct gg                                            22

<210> SEQ ID NO 410
<211> LENGTH: 21
<212> TYPE: DNA
<213> ORGANISM: Homo sapiens

<400> SEQUENCE: 410
gattctgcca gcagttggtc c                                             21

<210> SEQ ID NO 411
<211> LENGTH: 20
<212> TYPE: DNA
<213> ORGANISM: Homo sapiens

<400> SEQUENCE: 411
accacagctt cctggtggag                                               20

<210> SEQ ID NO 412
<211> LENGTH: 21
<212> TYPE: DNA
<213> ORGANISM: Homo sapiens

<400> SEQUENCE: 412
gagcggatgg gcttcttgat g                                             21

<210> SEQ ID NO 413
<211> LENGTH: 21
<212> TYPE: DNA
<213> ORGANISM: Homo sapiens

<400> SEQUENCE: 413
aacgtgacct tgtctcccaa c                                             21

<210> SEQ ID NO 414
<211> LENGTH: 20
<212> TYPE: DNA
<213> ORGANISM: Homo sapiens

<400> SEQUENCE: 414
gcatgacatc gccgattctt                                               20
```

```
<210> SEQ ID NO 415
<211> LENGTH: 21
<212> TYPE: DNA
<213> ORGANISM: Homo sapiens

<400> SEQUENCE: 415
ttcaacaagc ccacccacta c                                            21

<210> SEQ ID NO 416
<211> LENGTH: 21
<212> TYPE: DNA
<213> ORGANISM: Homo sapiens

<400> SEQUENCE: 416
gttctcaatg acagggatgc g                                            21

<210> SEQ ID NO 417
<211> LENGTH: 22
<212> TYPE: DNA
<213> ORGANISM: Homo sapiens

<400> SEQUENCE: 417
catggaatac ctggagggca ac                                           22

<210> SEQ ID NO 418
<211> LENGTH: 21
<212> TYPE: DNA
<213> ORGANISM: Homo sapiens

<400> SEQUENCE: 418
caggtgccag cagttcttca t                                            21

<210> SEQ ID NO 419
<211> LENGTH: 22
<212> TYPE: DNA
<213> ORGANISM: Homo sapiens

<400> SEQUENCE: 419
tctcagagct tctctacatc ac                                           22

<210> SEQ ID NO 420
<211> LENGTH: 21
<212> TYPE: DNA
<213> ORGANISM: Homo sapiens

<400> SEQUENCE: 420
ctgacgactc cttgttcacc a                                            21

<210> SEQ ID NO 421
<211> LENGTH: 21
<212> TYPE: DNA
<213> ORGANISM: Homo sapiens

<400> SEQUENCE: 421
tcacctcctc tgtaccattg c                                            21

<210> SEQ ID NO 422
<211> LENGTH: 20
<212> TYPE: DNA
<213> ORGANISM: Homo sapiens

<400> SEQUENCE: 422
ctcatctcca atgccctcga                                              20
```

```
<210> SEQ ID NO 423
<211> LENGTH: 21
<212> TYPE: DNA
<213> ORGANISM: Homo sapiens

<400> SEQUENCE: 423
tgcaatgaag agagggctct g                                           21

<210> SEQ ID NO 424
<211> LENGTH: 22
<212> TYPE: DNA
<213> ORGANISM: Homo sapiens

<400> SEQUENCE: 424
cgtggccctg gtatctattt ca                                          22

<210> SEQ ID NO 425
<211> LENGTH: 20
<212> TYPE: DNA
<213> ORGANISM: Homo sapiens

<400> SEQUENCE: 425
ggctacagct tcaccaccac                                             20

<210> SEQ ID NO 426
<211> LENGTH: 20
<212> TYPE: DNA
<213> ORGANISM: Homo sapiens

<400> SEQUENCE: 426
taatgtcacg cacgatttcc                                             20

<210> SEQ ID NO 427
<211> LENGTH: 18
<212> TYPE: DNA
<213> ORGANISM: Homo sapiens

<400> SEQUENCE: 427
cccagccagg aaatccat                                               18

<210> SEQ ID NO 428
<211> LENGTH: 20
<212> TYPE: DNA
<213> ORGANISM: Homo sapiens

<400> SEQUENCE: 428
ctggctcctc ttctgaatcg                                             20

<210> SEQ ID NO 429
<211> LENGTH: 20
<212> TYPE: DNA
<213> ORGANISM: Homo sapiens

<400> SEQUENCE: 429
cagtgcctgt caaaagttgc                                             20

<210> SEQ ID NO 430
<211> LENGTH: 18
<212> TYPE: DNA
<213> ORGANISM: Homo sapiens

<400> SEQUENCE: 430
ccccgttgaa acaccttg                                               18
```

```
<210> SEQ ID NO 431
<211> LENGTH: 20
<212> TYPE: DNA
<213> ORGANISM: Homo sapiens

<400> SEQUENCE: 431
gaccttggaa acccaatgaa                                              20

<210> SEQ ID NO 432
<211> LENGTH: 20
<212> TYPE: DNA
<213> ORGANISM: Homo sapiens

<400> SEQUENCE: 432
tccatctctg actgctggtg                                              20

<210> SEQ ID NO 433
<211> LENGTH: 20
<212> TYPE: DNA
<213> ORGANISM: Homo sapiens

<400> SEQUENCE: 433
tgctatccct gtacgcctct                                              20

<210> SEQ ID NO 434
<211> LENGTH: 20
<212> TYPE: DNA
<213> ORGANISM: Homo sapiens

<400> SEQUENCE: 434
gagtccatca cgatgccagt                                              20

<210> SEQ ID NO 435
<211> LENGTH: 20
<212> TYPE: DNA
<213> ORGANISM: Homo sapiens

<400> SEQUENCE: 435
ggacttcgag caagagatgg                                              20

<210> SEQ ID NO 436
<211> LENGTH: 19
<212> TYPE: DNA
<213> ORGANISM: Homo sapiens

<400> SEQUENCE: 436
cttctccagg gaggagctg                                               19

<210> SEQ ID NO 437
<211> LENGTH: 20
<212> TYPE: DNA
<213> ORGANISM: Homo sapiens

<400> SEQUENCE: 437
gatgcagatt gagagcctga                                              20

<210> SEQ ID NO 438
<211> LENGTH: 20
<212> TYPE: DNA
<213> ORGANISM: Homo sapiens

<400> SEQUENCE: 438
```

```
ttcttcaggt aggccagctc                                              20

<210> SEQ ID NO 439
<211> LENGTH: 21
<212> TYPE: DNA
<213> ORGANISM: Homo sapiens

<400> SEQUENCE: 439
ggtggtatgt gaccttggaa a                                            21

<210> SEQ ID NO 440
<211> LENGTH: 20
<212> TYPE: DNA
<213> ORGANISM: Homo sapiens

<400> SEQUENCE: 440
gcacactgaa acgaagacca                                              20

<210> SEQ ID NO 441
<211> LENGTH: 20
<212> TYPE: DNA
<213> ORGANISM: Homo sapiens

<400> SEQUENCE: 441
gaaggatttg ctgggaagtg                                              20

<210> SEQ ID NO 442
<211> LENGTH: 20
<212> TYPE: DNA
<213> ORGANISM: Homo sapiens

<400> SEQUENCE: 442
cgtggccctg gtatctattt                                              20
```

METHODS AND MATERIALS FOR IDENTIFYING METASTATIC MALIGNANT SKIN LESIONS AND TREATING SKIN CANCER

CROSS REFERENCE TO RELATED APPLICATIONS

This application is a continuation of U.S. patent application Ser. No. 15/503,973, filed Feb. 24, 2017, pending, which is a national stage entry under 35 U.S.C. § 371 of International Application No. PCT/US2015/045065, having an International Filing Date of Aug. 13, 2015, which claims the benefit of U.S. Provisional Ser. No. 62/037,325, filed Aug. 14, 2014, and U.S. Provisional Ser. No. 62/142,831, filed Apr. 3, 2015, the disclosure of each of which is incorporated herein in its entirety by this reference.

TECHNICAL FIELD

This application relates to methods and materials for identifying metastatic malignant skin lesions (e.g., metastatic malignant pigmented skin lesions). For example, this document relates to methods and materials for using quantitative PCR results and correction protocols to reduce the impact of basal keratinocyte contamination on the analysis of test sample results to identify metastatic malignant skin lesions. This document also relates to methods and materials for treating skin cancer. For example, this document relates to methods and materials for identifying a mammal (e.g., a human) having a pre-metastatic skin lesion (e.g., pre-metastatic melanoma) and treating that mammal with pentamidine (4,4'-[pentane-1,5-diylbis(oxy)]dibenzenecarboximidamide).

STATEMENT ACCORDING TO 37 C.F.R. § 1.821(c) or (e)—REQUEST TO TRANSFER COMPUTER-READABLE FORM OF SEQUENCE LISTING FROM PARENT APPLICATION

Pursuant to 37 C.F.R. § 1.821(c) or (e), the transmittal documents of this application include a Request to Transfer Computer-Readable Form of the Sequence Listing from the parent application Ser. No. 15/503,973, filed Feb. 24, 2017, the contents of which are incorporated herein by this reference.

BACKGROUND

Malignant skin lesions are typically identified by obtaining a skin biopsy and morphologically assessing the biopsy's melanocytes under a microscope. Such a procedure can be difficult to standardize and can lead to overcalling of melanomas.

Once a diagnosis of melanoma is made by morphological assessment, the risk of metastasis is typically determined by the invasion depth of malignant cells into the skin (i.e., the Breslow depth). The Breslow depth can dictate further work-up such as a need for an invasive sentinel lymph node (SLN) procedure. Such procedures, however, can lead to inaccurate determinations of the true malignant potential of a pigmented lesion.

BRIEF SUMMARY

Provided are methods and materials for identifying metastatic malignant skin lesions (e.g., metastatic malignant pigmented skin lesions). For example, this document provides methods and materials for using quantitative PCR results and correction protocols to reduce the impact of basal keratinocyte contamination on the analysis of test sample results to identify metastatic malignant skin lesions.

As described herein, quantitative PCR can be performed using a routine skin biopsy sample (e.g., a paraffin-embedded tissue biopsy) to obtain expression data (e.g., gene copy numbers) for one or more marker genes. Correction protocols can be used to reduce the impact of basal keratinocyte contamination on the analysis of the expression data from the test sample. For example, the contribution of gene expression from basal keratinocytes present within the test skin sample can be determined and removed from the overall gene expression values to determine the final gene expression value for a particular gene as expressed from cells other than basal keratinocytes (e.g., melanocytes). An assessment of the final gene expression values, which include minimal, if any, contribution from basal keratinocytes, for a collection of marker genes can be used to determine the benign or malignant or metastatic biological behavior of the tested skin lesion.

Also provided are methods and materials for treating skin cancer. For example, this document provides methods and materials for identifying a mammal (e.g., a human) having a pre-metastatic skin lesion (e.g., pre-metastatic melanoma) and treating that mammal with pentamidine.

As described herein, aggressive cancer cells (e.g., melanoma cells) can remodel their cell adhesion structures (e.g., osteopontin (SPP1) polypeptides) to invade tissues and metastasize. Screening over 1,200 compounds for the ability to reduce expression of SPP1 polypeptides resulted in the identification of pentamidine as an effective agent for disrupting integrin adhesion remodeling, thereby demonstrating that pentamidine can be used to reduce or inhibit cancer progression at an early stage (e.g., prior to metastatic cancer). In some cases, a mammal (e.g., a human) identified as having skin cancer cells that express an elevated level of PLAT, ITGB3, LAMB1, and/or TP53 can be administered pentamidine to reduce or inhibit cancer progression. For example, pentamidine can be administered to a mammal (e.g., a human) having pre-metastatic melanoma cells that were determined to have an elevated level of PLAT, ITGB3, LAMB1, and/or TP53 expression. In such cases, the mammal being treated with pentamidine may not experience cancer progression from the pre-metastatic melanoma state to a metastatic melanoma state.

In general, one aspect hereof features a method for identifying a metastatic malignant skin lesion. The method comprises, or consists essentially of, (a) determining, within a test sample, the expression level of a marker gene selected from the group consisting of PLAT, ITGB3, LAMB1, and TP53 to obtain a measured expression level of the marker gene for the test sample, (b) determining, within the test sample, the expression level of a keratinocyte marker gene to obtain a measured expression level of the keratinocyte marker gene for the test sample, (c) removing, from the measured expression level of the marker gene for the test sample, a level of expression attributable to keratinocytes present in the test sample using the measured expression level of the keratinocyte marker gene for the test sample and a keratinocyte correction factor to obtain a corrected value of marker gene expression for the test sample, and (d) identifying the test sample as containing a metastatic malignant skin lesion based, at least in part, on the corrected value of marker gene expression for the test sample. The keratinocyte marker gene can be K14. The marker gene can be PLAT or ITGB3. The step (c) can comprise (i) multiplying the measured expression level of the keratinocyte marker gene for the test sample by the keratinocyte correction factor to obtain a correction value and (ii) subtracting the correction value from the measured expression level of the marker gene for the test sample to obtain the corrected value of marker gene expression for the test sample. The method can comprise determining, within the test sample, the expression level of at least two marker genes selected from the group consisting of PLAT, ITGB3, LAMB1, and TP53 to obtain measured expression levels of the at least two marker genes for the test sample. The method can comprise determining, within the test sample, the expression level of at least three marker genes selected from the group consisting of PLAT, ITGB3, LAMB1, and TP53 to obtain measured expression levels of the at least three marker genes for the test sample. The method can comprise determining, within the test sample, the expression level of PLAT, ITGB3, LAMB1, and TP53 to obtain measured expression levels of the PLAT, ITGB3, LAMB1, and TP53 for the test sample.

In another aspect, this document features a kit for identifying a metastatic malignant skin lesion. The kit comprises, or consists essentially of, (a) a primer pair for determining, within a test sample, the expression level of a marker gene selected from the group consisting of LAMB1 and TP53 to obtain a measured expression level of the marker gene for the test sample, and (b) a primer pair for determining, within the test sample, the expression level of a keratinocyte marker gene to obtain a measured expression level of the keratinocyte marker gene for the test sample. The keratinocyte marker gene can be K14. The marker gene can be LAMB1. The marker gene can be TP53. The kit can comprise primer pairs for determining, within the test sample, the expression level of LAMB1 and TP53 to obtain measured expression levels of the LAMB1 and TP53 for the test sample. The kit can comprise primer pairs for determining, within the test sample, the expression level of PLAT to obtain measured expression levels of the PLAT for the test sample. The kit can comprise primer pairs for determining, within the test sample, the expression level of ITGB3 to obtain measured expression levels of the ITGB3 for the test sample. The kit can comprise primer pairs for determining, within the test sample, the expression level of PLAT and ITGB3 to obtain measured expression levels of the ITGB3 and PLAT for the test sample.

In another aspect, this document features a method for identifying a metastatic malignant skin lesion. The method comprises, or consists essentially of, (a) determining, within a test sample, the expression level of a marker gene selected from the group consisting of PLAT, ITGB3, LAMB1, and TP53 to obtain a measured expression level of the marker gene for the test sample, (b) determining, within the test sample, the expression level of a keratinocyte marker gene to obtain a measured expression level of the keratinocyte marker gene for the test sample, (c) removing, from the measured expression level of the marker gene for the test sample, a level of expression attributable to keratinocytes present in the test sample using the measured expression level of the keratinocyte marker gene for the test sample and a keratinocyte correction factor to obtain a corrected value of marker gene expression for the test sample, and (d) identifying the test sample as containing a metastatic malignant skin lesion based, at least in part, on the corrected value of marker gene expression for the test sample. The keratinocyte marker gene can be K14. The marker gene can be LAMB1 or TP53. The step (c) can comprise (i) multiplying the measured expression level of the keratinocyte marker gene for the test sample by the keratinocyte correction factor to obtain a correction value and (ii) subtracting the correction value from the measured expression level of the marker gene for the test sample to obtain the corrected value of marker gene expression for the test sample.

In another aspect, this document features a method for identifying a pre-metastatic skin lesion having an increased likelihood of metastasizing. The method comprises, or consists essentially of, (a) detecting the presence of an elevated level of PLAT, ITGB3, LAMB1, and TP53 expression in cells of the pre-metastatic skin lesion, and (d) classifying the pre-metastatic skin lesion as having an increased likelihood of metastasizing based, at least in part, on the presence. The method can comprise measuring the levels of PLAT, ITGB3, LAMB1, and TP53 expression in cells of the pre-metastatic skin lesion and performing an analysis using a two trees, two leaves model. The pre-metastatic skin lesion can be a human pre-metastatic skin lesion.

In another aspect, this document features a method for treating skin cancer, wherein the method comprises, or consists essentially of, (a) detecting the presence of an elevated level of PLAT, ITGB3, LAMB1, and TP53 expression in skin cancer cells of a mammal, and (d) administering pentamidine to the mammal. The mammal can be a human. The skin cancer can be pre-metastatic skin cancer. The skin cancer can be pre-metastatic melanoma. Administration of the pentamidine can reduce the progression of the pre-metastatic melanoma to metastatic melanoma. The pre-metastatic melanoma can fail to progress to metastatic melanoma following administration of the pentamidine. The method can comprise measuring the levels of PLAT, ITGB3, LAMB1, and TP53 expression in cells of the skin cancer cells and performing an analysis using a two trees, two leaves model.

Unless otherwise defined, all technical and scientific terms used herein have the same meaning as commonly understood by one of ordinary skill in the art to which this disclosure pertains. Although methods and materials similar or equivalent to those described herein can be used in the practice or testing of the disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the disclosure will be apparent from the following detailed description, and from the claims.

BRIEF DESCRIPTION OF THE DRAWINGS

FIG. 8A, is a graph depicting a null model randomization test suggesting a relationship exists between SLN positivity and the gene expression variables. The "best model" and "null model" reference lines mark the deviance scores for the best model fit to outcomes and the null model. The histogram shows the distribution of deviance scores for models fit against randomize outcomes. Since the best model outperforms the randomized outcome models there was a relationship between SLN positivity and gene expression. FIG. 8B illustrates the results from ten-fold cross validation results for models using 1, 2, and 3 trees with at most six binary variables or leaves. The label in each square denotes the number of trees used in the model. The scores on the y-axis are the deviance scores using the test data and the x-axis denotes the number of binary variables (leaves) used in each model. Notice that model the using two trees and four leaves had the best test score. FIG. 8C is a summary of the permutation test results for two trees using two to five leaves. The two solid reference lines indicate the best deviance score and the null model deviance score. The dashed reference line represents the deviance score using a one tree model. The histogram summarizes the deviance scores using permuted outcomes. There were 1,000 model fits for each model size. Scores above the best model reference line indicate there were models that fit the permuted data better than the actual data. For the model with two tree and five leaves about 10% deviance scores for models fit using permuted data have a lower score than using the best model for the observed original data indicated by the left most vertical reference line. FIG. 8D are the formulas for the best fitting models involved two trees with a model size of 4 or 5.

FIG. 11A is a graph depicting receiver operating characteristic curves for the three models in Table 16 using the model development cohort. FIG. 11B is a graph summarizing the sensitivity and specificity according to the predicted probability of a positive SLNB estimated from model C. FIG. 11C is a nomogram for the predicting positive SLNB based on model C.

FIG. 12A is a chart illustrating that IPTG reduces FAK mRNA through shRNA 841 and 102 but not control shRNA (NC) in WM858 cells (mean.+−.s.d.; n=4; *, p<0.05; , p<0.005; *, p<0.001). p values, Student's t-test; ns, not significant. FIG. 12B illustrates that FAK shRNA 102 but not control shRNA (NC) reduces FAK protein levels in WM858 cells. IPTG treatment of shRNA-free normal WM858 cells (no shRNA) was without effect on FAK protein levels. FIGS. 12C and 12D depict that FAK could be visualized in focal adhesions in WM858 NC but not shRNA 102 cells after 0.05 mM IPTG for 5 days. FIG. 12C depicts triple staining DAPI; FAK; Paxillin (PAX) as a focal adhesion marker. FIG. 12D depicts DAPI/FAK staining only. Bar, FIG. 13A: shRNAs 841, 102 and NC were induced in WM858 cells by IPTG for 5 days (n=4) followed by RNA quantitation. Genes regulated at 0 vs. 0.05 mM IPTG in 841 and 102 but not NC cells are shown. These were: ITGB3 (orange), FAK (blue). Light orange, light blue: up- or down-regulation, respectively, by either 841 or 102 shRNA. FIG. 13C: Flow cytometry of NC, 841 and 102 cells (un-induced vs. 0.05 mM IPTG for 5 days). FIG. 13D: Integrin cell surface mean intensities; mean.+−.s.d.; n=3; *, p<0.05; p values, Student's t-test; ns, not significant. FIG. 13E: Visualization of focal adhesions by paxillin staining on micropatterned fibronectin disks. FIG. 13P: ERK activity in NC, 841 and 102 cells (0.05 mM IPTG for 5 days) after overnight drug incubation.

FIGS. 15A-15J illustrate that pentamidine inhibits SPP1 expression, proliferation, and invasion of melanoma cells. FIG. 15A shows WM858 cells with a luciferase-tagged SPP1 promoter were screened against a LOPAC. FIGS. 15B-15D illustrate that pentamidine inhibits SPP1 promoter activity in the DUAL-GLO® assay (FIG. 15B), but also by quantitative PCR in normal WM858 (FIG. 15C) and M12 cells (FIG. 15D). FIG. 15E illustrates that pentamidine inhibits the expression of other adhesion molecules, i.e., (β3 integrin (ITGB3) and t-PA (PLAT). FIGS. 15F and 15G illustrate that pentamidine effectively inhibits M12 invasion into 2 mg/mL of MATRIGEL®. FIG. 15F depicts that a visible reduction in Matrigel invasion is observed that exceeds the effects of B-raf inhibition (FIG. 15G); blue, area of scratch wound at time zero; yellow line, invasion front; red, RFP-labeled M12 nuclei on phase contrast background. FIG. 15H is an image of a female nude mouse harboring an intradermal M12 PDX. FIG. 15I is an H&E stained cryosection of an untreated M12 PDX. FIG. 15I is a chart illustrating that pentamidine injections reduce SPP1, (β3 integrin, and t-PA (PLAT) mRNA expression in M12 PDX. Average of three mice is shown. PENTA, Pentamidine; DABRA, Dabrafenib. WM858 and M12 are B-rafV600E metastatic melanoma cells.

DETAILED DESCRIPTION

Provided are methods and materials for identifying metastatic malignant skin lesions (e.g., metastatic malignant pigmented skin lesions). For example, this document provides methods and materials for using quantitative PCR results and correction protocols to reduce the impact of basal keratinocyte contamination on the analysis of test sample results to identify metastatic malignant skin lesions.

Figure 1:
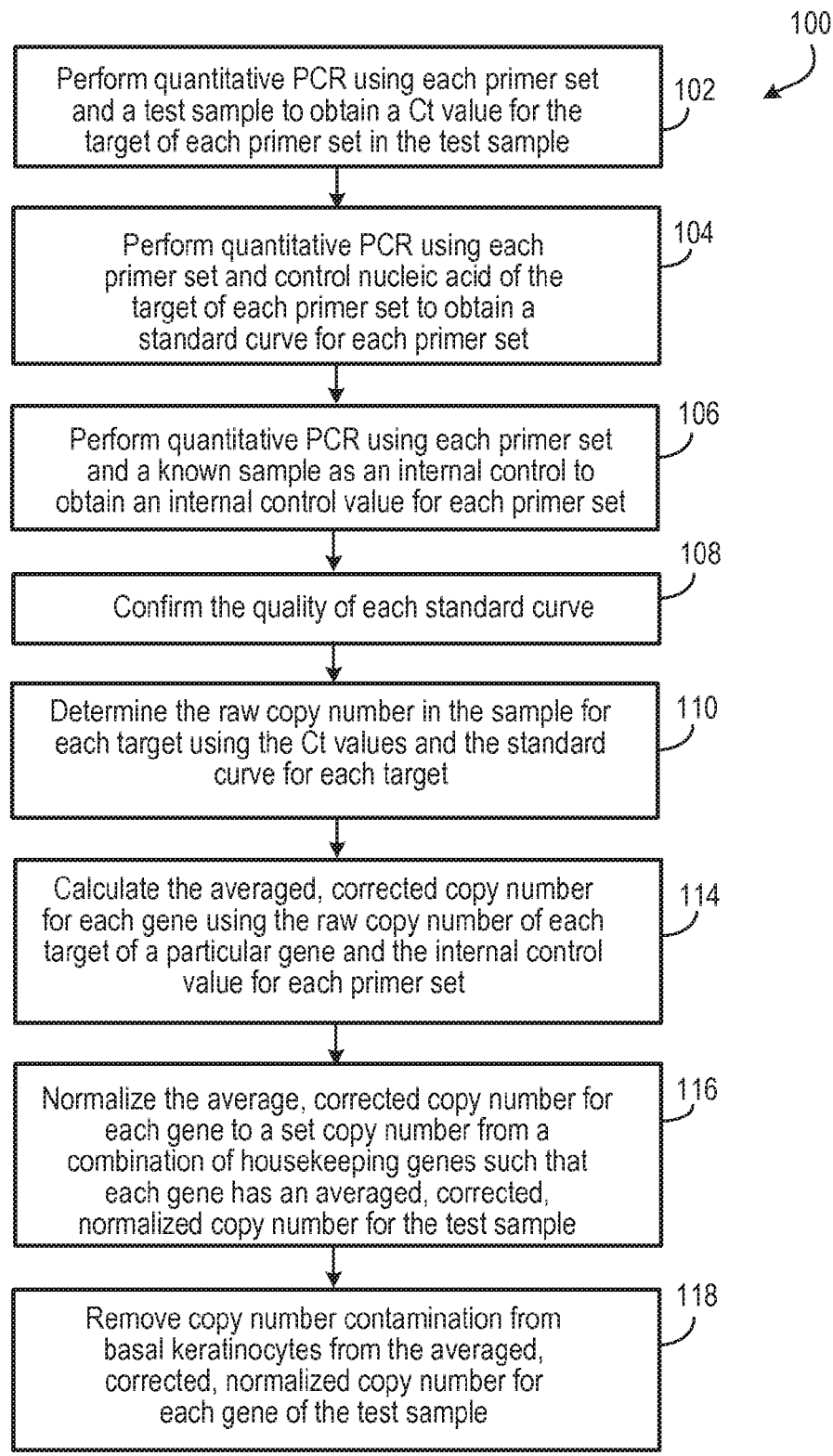
FIG. 1 is a flow chart of an exemplary process for determining the gene expression value, which includes minimal, if any, contribution from basal keratinocytes, for a marker gene by cells within a tested sample (e.g., a tested skin biopsy sample).

FIG. 1 shows an exemplary process 100 for determining a gene expression value, which includes minimal, if any, contribution from basal keratinocytes, for a marker gene by cells within a tested sample (e.g., a tested skin biopsy sample). The process begins at box 102, where quantitative PCR using a collection of primer sets and a test sample is used to obtain a Ct value for the target of each primer set. Each gene of interest can be assessed using a single primer set or multiple different primer sets (e.g., two, three, four, five, six, seven, or more different primer sets). In some cases, quantitative PCR is performed using each primer set and control nucleic acid of the target of each primer set (e.g., linearized cDNA fragments) to obtain a standard curve for each primer set as set forth in box 104. In some cases, quantitative PCR is performed using each primer set and a known sample as an internal control (e.g., a stock biological sample) to obtain an internal control value for each primer set as set forth in box 106. This internal control can be used to set values for each primer set across different assays. In some cases, the quantitative PCR performed according to boxes 102, 104, and 106 can be performed in parallel. For example, the quantitative PCR performed according to boxes 102, 104, and 106 can be performed in a single 96-well format.

At box 108, the quality of the obtained standard curves can be confirmed. In some cases, a gene of interest included in the assay format can be a melanocyte marker (e.g., levels of MLANA and/or MITF expression) to confirm the presence of melanocytes in the test sample. Other examples of melanocyte markers that can be used as described herein include, without limitation, TYR, TYRP1, DCT, PMEL, OCA2, MLPH, and MC1R.

At box 110, the raw copy number of each target present in the test sample is determined using the Ct values and the standard curve for each target. In some cases, the averaged, corrected copy number for each gene is calculated using the raw copy number of each target of a particular gene and the internal control value for each primer set (box 114). This averaged, corrected copy number value for each gene can be normalized to a set number of one or more housekeeping genes as set forth in box 114. For example, each averaged, corrected copy number value for each gene can be normalized to 100,000 copies of the combination of ACTB, RPL8, RPLP0, and B2M. Other examples of housekeeping genes that can be used as described herein include, without limitation, RRN18S, GAPDH, PGK1, PPIA, RPL13A, YWHAZ, SDHA, TFRC, ALAS1, GUSB, HMBS, HPRT1, TBP, CLTC, MRFAP1, PPP2CA, PSMA1, RPL13A, RPS29, SLC25A3, TXNL1, and TUPP. Once normalized, the copy number values for each gene can be referred to as the averaged, corrected, normalized copy number for that gene as present in the test sample.

At box 116, the averaged, corrected, normalized copy number for each gene can be adjusted to remove the copy number contamination from basal keratinocytes present in the test sample, box 118. In general, copy number contamination from basal keratinocytes can be removed by (a) determining a keratinocyte correction factor for the gene of interest using one or more keratinocyte markers (e.g., keratin 14 (K14)) and one or more normal skin samples (e.g., FFPE-embedded normal skin samples), (b) determining the averaged, corrected, normalized copy number value for the one or more keratinocyte markers of the test sample and multiplying that value by the keratinocyte correction factor to obtain a correction value for the gene of interest, and (c) subtracting that correction value from the averaged, corrected, normalized copy number value of the gene of interest to obtain the final copy number for the gene of interest. Examples of keratinocyte markers that can be used as described herein include, without limitation, KRT5, KRT1, KRT10, KRT17, ITGB4, ITGA6, PLEC, DST, and COL17A1.

Figure 2:
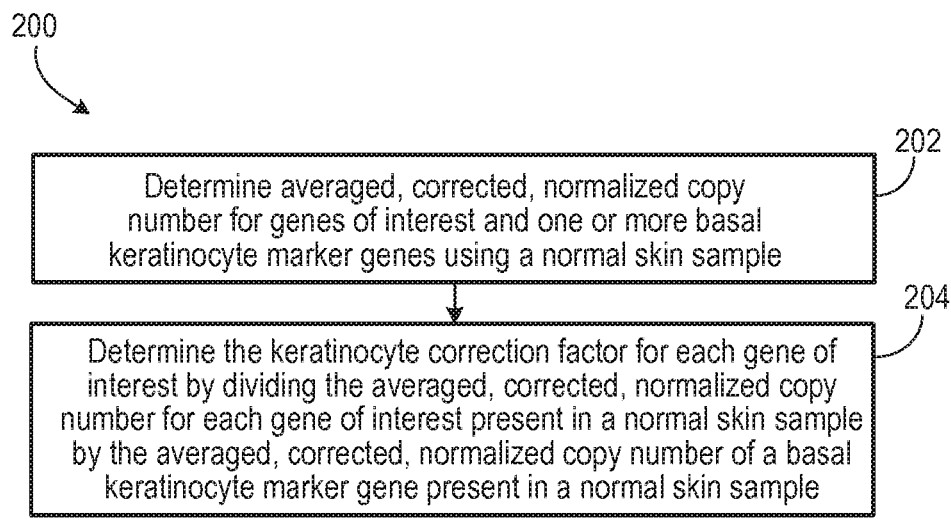
FIG. 2 is a flow chart of an exemplary process for determining a keratinocyte correction factor for a marker gene of interest.

With reference to FIG. 2, process 200 can be used to obtain a keratinocyte correction factor for a gene of interest. At box 202, the averaged, corrected, normalized copy number for one or more genes of interest (e.g., Gene X) and one or more basal keratinocyte marker genes (e.g., K14) are determined using one or more normal skin samples and procedures similar to those described in FIG. 1. As box 204, the keratinocyte correction factor for each gene of interest (e.g., Gene X) is determined by dividing the averaged, corrected, normalized copy number for each gene of interest present in a normal skin sample by the averaged, corrected, normalized copy number of a basal keratinocyte marker gene present in a normal skin sample. Examples of keratinocyte correction factors for particular genes of interest are set forth in Table E under column "AVG per copy K14."

Figure 3:
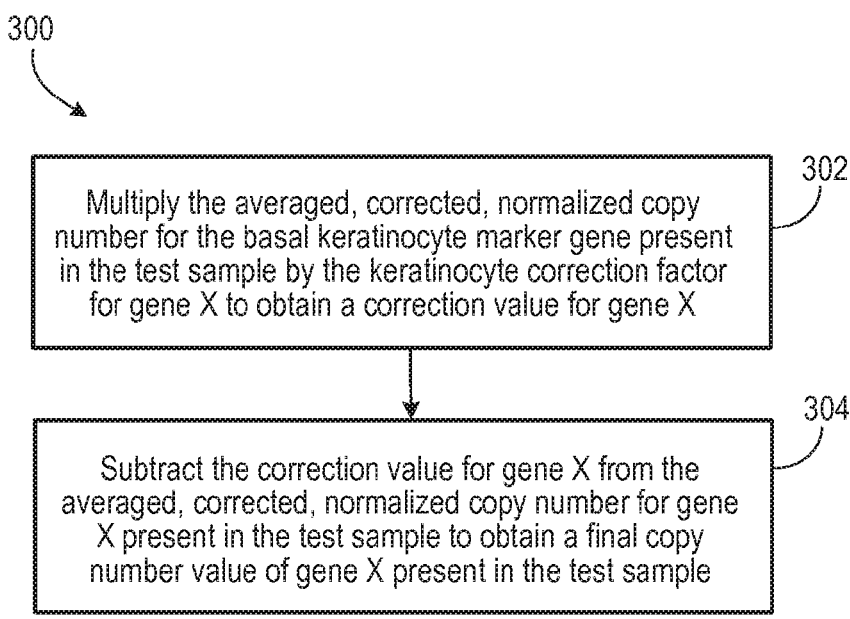
FIG. 3 is a flow chart of an exemplary process for removing copy number contamination from basal keratinocytes from a copy number value for a marker gene to determine the gene expression value, which includes minimal, if any, contribution from basal keratinocytes, for that marker gene by cells within a tested sample (e.g., a tested skin biopsy sample).

With reference to FIG. 3, which is a flow chart of an exemplary process 300, once a keratinocyte correction factor is determined for a particular gene of interest (e.g., Gene X), then the averaged, corrected, normalized copy number for the basal keratinocyte marker gene present in the test sample can be multiplied by the keratinocyte correction factor for the gene of interest (e.g., Gene X) to obtain a correction value for the gene of interest (e.g., Gene X). See, e.g., box 302. At box 304, the correction value for the gene of interest (e.g., Gene X) is subtracted from the averaged, corrected, normalized copy number for the gene of interest (e.g., Gene X) present in the test sample to obtain a final copy number value of the gene of interest (e.g., Gene X) present in the test sample.

Figure 4:
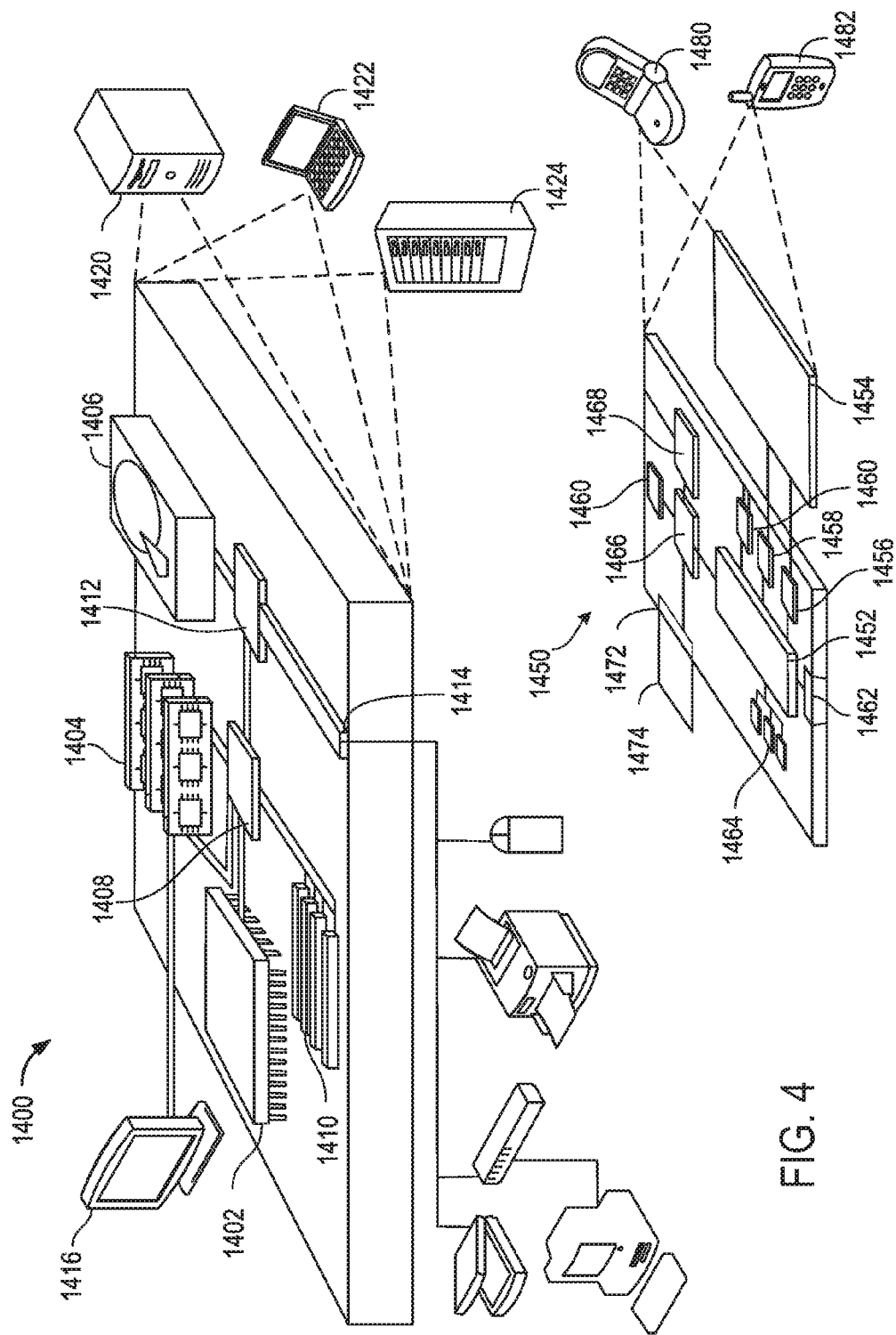
FIG. 4 is a diagram of an example of a generic computer device and a generic mobile computer device that can be used as described herein.

FIG. 4 is a diagram of an example of a generic computer device 1400 and a generic mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the disclosures described and/or claimed in this document.

Computing device 1400 includes a processor 1402, memory 1404, a storage device 1406, a high-speed interface 1408 connecting to memory 1404 and high-speed expansion ports 1410, and a low-speed controller 1412 connecting to low-speed expansion port 1414 and storage device 1406. Each of the components 1402, 1404, 1406, 1408, 1410, and 1412, are interconnected using various buses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high-speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high-speed interface 1408 manages bandwidth-intensive operations for the computing device 1400, while the low-speed controller 1412 manages lower bandwidth-intensive operations. Such allocation of functions is exemplary only. In one implementation, the high-speed interface 1408 is coupled to memory 1404, display 1416 (e.g., through a graphics processor or accelerator), and to high-speed expansion ports 1410, which may accept various expansion cards (not shown). In the implementation, low-speed controller 1412 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. In some cases, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

This document also provides methods and materials involved in treating mammals having skin cancer (e.g., melanoma such as pre-metastatic melanoma) by administering pentamidine to the mammal. Any appropriate mammal having skin cancer can be treated as described herein. For example, humans and other primates such as monkeys having skin cancer can be treated with pentamidine. In some cases, dogs, cats, horses, bovine species, porcine species, mice, or rats can be treated with pentamidine as described herein. In addition, a mammal having any particular type of skin cancer can be treated as described herein. For example, a mammal having melanoma, pre-metastatic melanoma, locally metastatic melanoma (i.e., skin in close proximity to primary melanoma), regionally metastatic melanoma (e.g., metastases to regional sentinel lymph nodes), or distant metastases (e.g., metastases to internal organs) can be treated with pentamidine as described herein. In some cases, a mammal determined to have skin cancer cells that express an elevated level of one or more marker genes described herein (e.g., PLAT, ITGB3, LAMB1, and/or TP53) can be treated with pentamidine. In some cases, a mammal (e.g., a human) determined to have skin cancer cells that express an elevated level of one or more marker genes (e.g., PLAT, ITGB3, LAMB1, and/or TP53) using the methods or materials provided herein can be treated with pentamidine.

Any appropriate method can be used to identify a mammal having skin cancer (e.g., pre-metastatic melanoma) that can be treated using pentamidine. For example, imaging, biopsy, pathology, PCR, and sequencing techniques can be used to identify a human having skin cancer cells that express an elevated level of PLAT, ITGB3, LAMB1, and/or TP53.

Once identified as having skin cancer or skin cancer that expresses an elevated level of PLAT, ITGB3, LAMB1, and/or TP53, the mammal can be administered pentamidine. In some cases, pentamidine can be administered in combination with a chemotherapeutic agent to treat skin cancer (e.g., pre-metastatic melanoma). Examples of chemotherapeutic agents that can be used in combination with pentamidine include, without limitation, taxane therapies, anthracycline therapies, and gemcitabine therapies. Examples of taxane therapies include, without limitation, cancer treatments that involve administering taxane agents such as paclitaxel, docetacel, or other microtubule disrupting agents such as vinblastine, vincristine, or vinorelbine. In some cases, drugs used to treat gout or chochicine can be used as described herein to treat a mammal having skin cancer. Examples of anthracycline therapies include, without limitation, cancer treatments that involve administering anthracycline agents such as doxorubicine, daunorubicin, epirubicin, idarubicin, valrubicin, or mitoxantrone.

In some cases, pentamidine can be formulated into a pharmaceutically acceptable composition for administration to a mammal having skin cancer (e.g., pre-metastatic melanoma). For example, a therapeutically effective amount of pentamidine can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing pentamidine can be designed for oral or parenteral (including subcutaneous, intramuscular, intravenous, and intradermal) administration. When being administered orally, a pharmaceutical composition containing pentamidine can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient; and aqueous and non-aqueous sterile suspensions that may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

Such injection solutions can be in the form, for example, of a sterile injectable aqueous or oleaginous suspension. This suspension may be formulated using, for example, suitable dispersing or wetting agents (such as, for example, TWEEN® 80) and suspending agents. The sterile injectable preparation can be a sterile injectable solution or suspension in a non-toxic parenterally-acceptable diluent or solvent, for example, as a solution in 1,3-butanediol. Examples of acceptable vehicles and solvents that can be used include, without limitation, mannitol, Ringer's solution, and isotonic sodium chloride solution. In addition, sterile, fixed oils can be used as a solvent or suspending medium. In some cases, a bland fixed oil can be used such as synthetic mono- or di-glycerides. Fatty acids, such as oleic acid and its glyceride derivatives can be used in the preparation of injectables, as can natural pharmaceutically-acceptable oils, such as olive oil or castor oil, including those in their polyoxyethylated versions. In some cases, these oil solutions or suspensions can contain a long-chain alcohol diluent or dispersant.

In some cases, a pharmaceutically acceptable composition including pentamidine can be administered locally or systemically. For example, a composition containing pentamidine can be administered locally by injection into lesions at surgery or by subcutaneous administration of a sustained release formulation. In some cases, a composition containing pentamidine can be administered systemically orally or by injection to a mammal (e.g., a human).

Effective doses can vary depending on the severity of the cancer, the route of administration, the age and general health condition of the subject, excipient usage, the possibility of co-usage with other therapeutic treatments such as use of chemotherapeutic agents, and the judgment of the treating physician.

An effective amount of a composition containing pentamidine can be any amount that reduces skin cancer progression without producing significant toxicity to the mammal. For example, an effective amount of pentamidine can be from about 0.01 mg/kg to about 4 mg/kg. In some cases, between about 10 mg and about 1500 mg of pentamidine can be administered to an average sized human (e.g., about 70-75 kg human) daily for about one week to about one year (e.g., about two weeks to about four months). If a particular mammal fails to respond to a particular amount, then the amount of pentamidine can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that reduces skin cancer progression without producing significant toxicity to the mammal. For example, the frequency of administration can be from about once a week to about once every two to three weeks. The frequency of administration can remain constant or can be variable during the duration of treatment. A course of treatment with a composition containing pentamidine can include rest periods. For example, a composition containing pentamidine can be administered daily over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition containing pentamidine can be any duration that reduces skin cancer progression without producing significant toxicity to the mammal. Thus, the effective duration can vary from several days to several weeks, months, or years. In general, the effective duration for the treatment with pentamidine to reduce skin cancer progression can range in duration from six months to one year. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and the severity of one or more symptoms related to the skin cancer being treated (e.g., pre-metastatic melanoma) can be monitored. Any appropriate method can be used to determine whether or not cancer progression is reduced. For example, the severity of a symptom of skin cancer can be assessed using imagine and pathology assessment of biopsy samples or surgical samples.

This disclosure will be further described in the following examples, which do not limit the scope of the disclosure described in the claims.

EXAMPLES

Example 1—Marker Genes that Discriminate Between Benign and Malignant Tissue

Marker genes were ordered by their ability to differentiate benign from malignant tissue (Table A). This was based on the analysis of 73 benign and 53 malignant tissues, and the hypothesis that changes in expression of fibronectin-associated gene networks are indicative of malignant cell behavior. Values of the test statistic were for the Wilcoxon rank sum test. The values of the test statistic for a Winsorized two-sample test (trimmed outliers were replaced with actual values) and for the chi-square test for the zero vs. >zero versions of each variable were included. The top five discriminatory genes based on each statistical test were highlighted in bold.

TABLE A

| | Test statistic value | | |
|---|---|---|---|
| gene | Wilcoxon rank sum test | Winsorized two-sample t-test | Chi-square test |
| FN1 | −10.2312 | −8.04081 | 106.714 |
| SPP1 | −9.0279 | −4.9374 | 86.774 |
| COL4A1 | −8.8807 | −7.27171 | 83.711 |
| TNC | −8.7511 | −8.31049 | 75.549 |
| ITGA3 | −8.6008 | −5.86334 | 79.788 |
| LOXL3 | −8.1978 | −6.75327 | 75.144 |
| AGRN | −8.1243 | −7.91238 | 62.611 |
| VCAN | −8.0812 | −6.24088 | 67.388 |
| PLOD3 | −8.0384 | −6.89248 | 62.691 |
| ITGB1 | −8.0021 | −7.38143 | 59.973 |
| PTK2 | −7.5279 | −7.19889 | 54.446 |
| CTGF | −7.4997 | −5.581 | 57.79 |
| PLOD1 | −7.332 | −7.36126 | 44.87 |
| LAMC1 | −7.2425 | −6.1057 | 54.233 |
| THBS1 | −7.2425 | −5.60331 | 54.233 |
| LOXL2 | −7.2241 | −6.33208 | 55.909 |
| IL6 | −7.1777 | −6.41883 | 56.966 |
| LOXL1 | −7.1279 | −6.34431 | 52.878 |
| IL8 | −7.1194 | −5.76042 | 57.296 |
| CYR61 | −6.741 | −6.97388 | 43.866 |
| ITGAV | −6.5947 | −6.27571 | 47.021 |
| YAP | −6.4848 | −6.36431 | 42.417 |
| BGN | −6.3419 | −6.01066 | 25.387 |
| LAMB1 | −6.3293 | −5.68826 | 37.061 |
| ITGB3 | −6.3142 | −5.13158 | 40.835 |
| CXCL1 | −6.1077 | −5.66564 | 40.137 |
| THBS2 | −6.0427 | −5.02003 | 37.413 |
| COL18A1 | −6.0379 | −4.9125 | 41.339 |
| SPARC | −6.0272 | −6.39324 | 38.098 |
| TP53 | −6.0182 | −6.18554 | 34.945 |
| PLOD2 | −5.9082 | −3.50272 | 47.576 |
| CCL2 | −5.8844 | −5.38758 | 30.69 |
| FBLN2 | −5.5848 | −4.59826 | 31.913 |
| LAMA1 | −5.4876 | −4.2817 | 31.071 |
| THBS4 | −5.3971 | −3.88786 | 35.27 |
| COL1A1 | −5.325 | −4.37617 | 34.693 |
| ITGA5 | −4.9847 | −3.56695 | 25.243 |
| TAZ | −4.036 | −3.26011 | 18.313 |
| POSTN | −3.8054 | −2.78378 | 19.813 |
| LOX | −3.728 | −2.8677 | 17.157 |
| CSRC | −3.7078 | −3.71759 | 13.983 |
| LAMA3 | −3.5805 | −2.99652 | 13.391 |
| CDKN1A | −3.5766 | −3.20447 | 17.228 |
| CDKN2A | −3.5491 | −2.90903 | 15.938 |
| ITGA2 | −3.4083 | −2.72495 | 11.766 |
| LAMC2 | −3.4083 | −2.53784 | 11.766 |
| PCOLCE2 | −3.3469 | −3.53676 | 14.449 |
| LOXL4 | −3.2079 | −2.76128 | 10.943 |

TABLE A-continued

| gene | Wilcoxon rank sum test | Winsorized two-sample t-test | Chi-square test |
|---|---|---|---|
| PCOLCE | −2.2172 | −1.13805 | 7.993 |
| LAMB3 | −1.2822 | 0.89459 | 7.028 |
| CSF2 | 2.175 | 1.93095 | 4.522 |

Example 2—Marker Panel Revision after Statistical Analysis

The candidate gene list from Example 1 was modified to include other FN1 network genes as well as four housekeeping genes (ACTB, RPLP0, RPL8, and B2M), two keratinocyte markers (K10 and K14) to assess keratinocyte contamination, and four melanocyte markers (MITF, TYR, MLANA and PMEL) to assess melanocyte content in the skin sections. Genes from Example 1 with low discriminatory value and a more distant neighborhood to FN1 were excluded from the test setup (LAMC1, LOXL2, CYR61, YAP, BGN, LAMB1, THBS2, COL18A1, SPARC, TP53, PLOD2, CCL2, FBLN2, LAMA1, THBS4, COL1A1, TAZ, POSTN, LOX, CSRC, LAMA5, CDKN1A, CDKN2A, LAMC2, PCOLCE2, LOXL4, PCOLCE, LAMB5, and CSF2). Instead, the discriminatory ability of other FN1 network genes was determined (PLAT, CSK, GDF15, FARP1, ARPC1B, NES, NTRK3, SNX17, L1CAM, and CD44). The following results were based on the analysis of 26 benign nevi and 52 primary cutaneous melanomas with documented subsequent metastasis or skin lesions of melanoma metastasis (Table B). The top five genes were highlighted.

TABLE B

| gene | Wilcoxon rank sum test | Winsorized two-sample t-test | Chi-square test |
|---|---|---|---|
| COL4A1 | −5.85975 | −5.42545 | 46.3273 |
| FN1 | −5.50862 | −3.63639 | 35.1951 |
| PLAT | −4.82670 | −3.13568 | 25.7234 |
| IL8 | −4.61443 | −4.41668 | 28.6000 |
| SPP1 | −4.60153 | −3.08137 | 23.0816 |
| PLOD3 | −4.37001 | −3.91553 | 18.8036 |
| TNC | −4.26431 | −3.14128 | 19.5000 |
| CXCL1 | −4.24452 | −3.76681 | 20.6471 |
| CSK | −4.15178 | −2.96444 | 18.3962 |
| GDF15 | −4.01364 | −2.99752 | 13.7083 |
| ITGB3 | −3.92608 | −2.80068 | 16.3091 |
| CCL2 | −3.61870 | −3.45423 | 17.5176 |
| VCAN | −3.46906 | −2.26781 | 12.5593 |
| ITGB1 | −3.40897 | −3.63399 | 5.0221 |
| PLOD1 | −3.40380 | −3.20309 | 9.2625 |
| CTGF | −3.11725 | −2.20507 | 10.0645 |
| THBS1 | −3.11721 | −2.01257 | 10.0645 |
| ITGA3 | −3.04915 | −2.65398 | 7.5341 |
| FARP1 | −2.99724 | −2.28024 | 9.2857 |
| AGRN | −2.92104 | −3.30679 | 1.8838 |
| IL6 | −2.85960 | −3.05600 | 10.6257 |
| LOXL3 | −2.84999 | −2.70498 | 5.1096 |
| LOXL1 | −2.69957 | −2.11477 | 8.1250 |
| ARPC1B | −2.57571 | −2.82320 | All but 1 value > 0 |
| NES | −2.45264 | −2.70056 | 2.4375 |
| PTK2 | −2.22328 | −2.26180 | 4.4057 |
| ITGA2 | −2.08353 | −1.50078 | 4.4571 |
| ITGA5 | −1.93478 | −1.39663 | 3.8451 |
| ITGAV | −1.29341 | −0.81964 | 3.5615 |
| NTRK3 | −1.22485 | 75 of the 78 values are =0 | |

TABLE B-continued

| gene | Wilcoxon rank sum test | Winsorized two-sample t-test | Chi-square test |
|---|---|---|---|
| MITF | 0.58305 | 0.73916 | 0.4274 |
| SNX17 | 0.74754 | 0.90733 | 0.0785 |
| L1CAM | 1.61125 | 0.27151 | 2.1081 |
| MLANA | 2.96258 | 2.92548 | All values > 0 |
| CD44 | 5.23089 | 7.17590 | All but 1 value > 0 |

Figure 7:
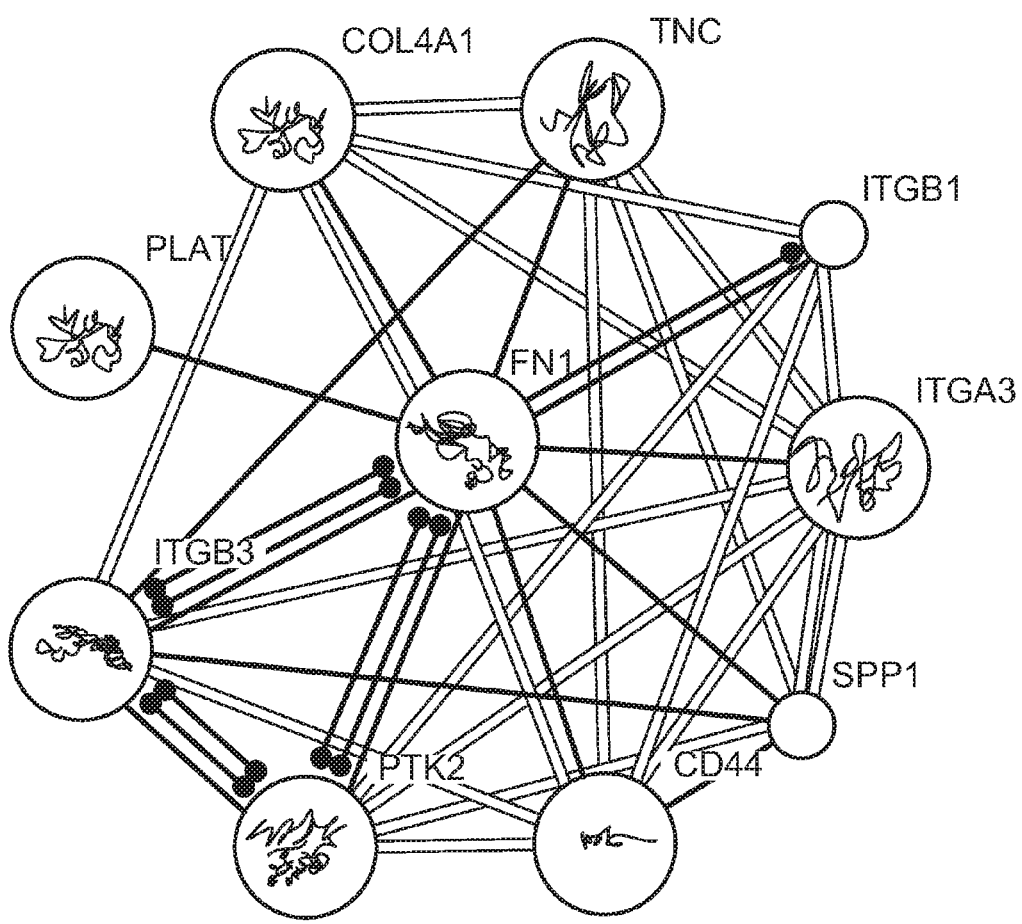
FIG. 7 is a network diagram.

Based on the results of Example 1 and above, FN1 was identified as a component of the melanoma phenotype that is at the core of a gene network that discriminates between benign and malignant melanocytic skin lesions (FIG. 7). The modeling was based on the STRING 9.0 database (string-db.org).

The list of all 71 genes tested is provided in Table 1.

TABLE 1

List of genes used to discriminate benign skin tissue lesions from malignant skin tissue lesions.

| Gene Name | GENBANK® Accession No. | GENBANK® GI No. |
|---|---|---|
| FN1 | NM_212482 | 47132556 |
| | NM_002026 | 47132558 |
| | NM_212474 | 47132548 |
| | NM_212476 | 47132552 |
| | NM_212478 | 47132554 |
| | NM_054034 | 47132546 |
| SPP1 | NM_001040058 | 91206461 |
| | NM_001040060 | 91598938 |
| | NM_000582 | 38146097 |
| COL4A1 | NM_001845 | 148536824 |
| TNC | NM_002160 | 340745336 |
| ITGA3 | NM_005501 | 171846264 |
| | NM_002204 | 171846266 |
| LOXL3 | NM_032603 | 22095373 |
| AGRN | NM_198576 | 344179122 |
| VCAN | NM_004385 | 255918074 |
| | NM_001164098 | 255918078 |
| | NM_001164097 | 255918076 |
| PLOD3 | NM_001084 | 62739167 |
| ITGB1 | NM_002211 | 182519230 |
| | NM_133376 | 182507162 |
| | NM_033668 | 182507160 |
| PTK2 | NM_001199649 | 313851043 |
| | NM_005607 | 313851042 |
| | NM_153831 | 313851041 |
| CTGF | NM_001901 | 98986335 |
| PLOD1 | NM_000302 | 324710986 |
| LAMC1 | NM_002293 | 145309325 |
| THBS1 | NM_003246 | 40317625 |
| LOXL2 | NM_002318 | 67782347 |
| IL6 | NM_000600 | 224831235 |
| LOXL1 | NM_005576 | 67782345 |
| IL8 | NM_000584 | 324073503 |
| CYR61 | NM_001554 | 197313774 |
| ITGAV | NM_001144999 | 223468594 |
| | NM_001145000 | 223468596 |
| | NM_002210 | 223468593 |
| YAP | NM_001130145 | 303523503 |
| | NM_001195045 | 303523626 |
| | NM_006106 | 303523510 |
| | NM_001195044 | 303523609 |
| BGN | NM_001711 | 268607602 |
| LAMB1 | NM_002291 | 167614503 |
| ITGB3 | NM_000212 | 47078291 |
| CXCL1 | NM_001511 | 373432598 |
| THBS2 | NM_003247 | 40317627 |
| COL18A1 | NM_030582 | 110611234 |
| | NM_130445 | 110611232 |
| SPARC | NM_003118 | 365777426 |

TABLE 1-continued

List of genes used to discriminate benign skin tissue lesions from malignant skin tissue lesions.

| Gene Name | GENBANK® Accession No. | GENBANK® GI No. |
|---|---|---|
| TP53 | NM_000546 | 371502114 |
|  | NM_001126112 | 371502115 |
|  | NM_001126114 | 371502117 |
|  | NM_001126113 | 371502116 |
| PLOD2 | NM_182943 | 62739164 |
|  | NM_000935 | 62739165 |
| CCL2 | NM_002982 | 56119169 |
| FBLN2 | NM_001998 | 51873054 |
|  | NM_001004019 | 51873052 |
|  | NM_001165035 | 259013546 |
| LAMA1 | NM_005559 | 329112585 |
| THBS4 | NM_003248 | 291167798 |
| COL1A1 | NM_000088 | 110349771 |
| ITGA5 | NM_002205 | 56237028 |
| TAZ | NM_000116 | 195232764 |
|  | NM_181311 | 195232766 |
|  | NM_181312 | 195232765 |
|  | NM_181313 | 195232767 |
| POSTN | NM_001135934 | 209862910 |
|  | NM_006475 | 209862906 |
|  | NM_001135935 | 209863010 |
| LOX | NM_001178102 | 296010939 |
|  | NM_002317 | 296010938 |
| CSRC | NM_005417 | 38202215 |
|  | NM_198291 | 38202216 |
| LAMA3 | NM_198129 | 38045909 |
|  | NM_001127717 | 189217424 |
| CDKN1A | NM_000389 | 310832422 |
|  | NM_001220777 | 334085239 |
|  | NM_078467 | 310832423 |
|  | NM_001220778 | 334085241 |
| CDKN2A | NM_000077 | 300863097 |
|  | NM_058195 | 300863095 |
|  | NM_001195132 | 304376271 |
| ITGA2 | NM_002203 | 116295257 |
| LAMC2 | NM_005562 | 157419137 |
|  | NM_018891 | 157419139 |
| PCOLCE2 | NM_013363 | 296317252 |
| LOXL4 | NM_032211 | 067782348 |
| PCOLCE | NM_002593 | 157653328 |
| LAMB3 | NM_000228 | 62868214 |
|  | NM_001017402 | 62868216 |
|  | NM_001127641 | 189083718 |
| CSF2 | NM_000758 | 371502128 |
| ACTB | NM_001101 | 168480144 |
| RPLP0 | NM_053275 | 49087137 |
|  | NM_001002 | 49087144 |
| RPL8 | NM_000973 | 72377361 |
|  | NM_033301 | 15431305 |
| B2M | NM_004048 | 37704380 |
| K10 | NM_000421 | 195972865 |
| K14 | NM_000526 | 197313720 |
| MITF | NM_198158 | 296841082 |
|  | NM_198177 | 296841080 |
|  | NM_006722 | 296841079 |
|  | NM_198159 | 296841078 |
|  | NM_000248 | 296841081 |
|  | NM_001184967 | 296841084 |
|  | NM_198178 | 296923803 |
| TYR | NM_000372 | 113722118 |
| MLANA | NM_005511 | 5031912 |
| PMEL | NM_001200054 | 318037594 |
|  | NM_001200053 | 318037592 |
|  | NM_006928 | 318068057 |
| NES | NM_006617 | 38176299 |
| L1CAM | NM_024003 | 221316758 |
|  | NM_001143963 | 221316759 |
|  | NM_000425 | 221316755 |
| GDF15 | NM_004864 | 153792494 |
| ARPC1B | NM_005720 | 325197176 |
| FARP1 | NM_005766 | 48928036 |
|  | NM_001001715 | 159032536 |
| NTRK3 | NM_001007156 | 340745351 |
|  | NM_001012338 | 340745349 |
|  | NM_001243101 | 340745352 |
|  | NM_002530 | 340745350 |
| CSK | NM_001127190 | 187475372 |
|  | NM_004383 | 187475371 |
| CD44 | NM_001001391 | 48255940 |
|  | NM_001001392 | 48255942 |
|  | NM_001202556 | 321400139 |
|  | NM_001001389 | 48255936 |
|  | NM_000610 | 48255934 |
|  | NM_001001390 | 48255938 |
|  | NM_001202555 | 321400137 |
|  | NM_001202557 | 321400141 |
| SNX17 | NM_014748 | 388596703 |
| PLAT | NM_000930 | 132626665 |
|  | NM_033011 | 132626641 |

Gene expression of target genes was assessed by SYBR/EVA-Green based RT-PCR. All tested genes were accompanied by a standard curve for quantification of absolute copy number per a defined number of housekeeping genes. mRNA extraction from paraffin-embedded biospecimen was performed using an extraction protocol (QIAGEN® RNA FFPE extraction kit) and an extraction robot (QIACuBE® from QIAGEN®). mRNA was transcribed into cDNA using a commercially available kit (iScript kit from BioRad), and Fluidigm technology was used for PCR cycling.

The primer design was performed using web-based open access software. The primers were HPLC purified to minimize background and were optimized for formalin-fixed, paraffin-embedded (FFPE) tissue (i.e., highly degraded tissue). The primers were designed to detect a maximum number of gene transcripts and were designed to be cDNA specific (i.e., not affected by genomic DNA contamination of the total, tissue-derived cDNA). The housekeeping genes, keratin genes, melanocyte-specific genes, and selected high-interest genes were detected using four separate and individually designed primer pairs. The primer pairs are set forth in Table 2.

TABLE 2

Primer sets for indicated genes.

| Gene Name | Forward primer | Reverse primer |
|---|---|---|
| ACTB | 5'-GCCAACCGCGAGAAGATG-3'; SEQ ID NO: 1 | 5'-GGCTGGGGTGTTGAAGGT-3'; SEQ ID NO: 2 |
|  | 5'-CGCGAGAAGATGACCCAGAT-3'; SEQ ID NO: 3 | 5'-GGGGTGTTGAAGGTCTCAAA-3'; SEQ ID NO: 4 |
|  | 5'-TGACCCAGATCATGTTTGAGA-3'; SEQ ID NO: 5 | 5'-GTACATGGCTGGGGTGTTG-3'; SEQ ID NO: 6 |

TABLE 2-continued

Primer sets for indicated genes.

| Gene Name | Forward primer | Reverse primer |
|---|---|---|
| | 5'-CTGAACCCCAAGGCCAAC-3';<br>SEQ ID NO: 7 | 5'-TGATCTGGGTCATCTTCTCG-3';<br>SEQ ID NO: 8 |
| RPLP0 | 5'-AACTCTGCATTCTCGCTTCC-3';<br>SEQ ID NO: 9<br>5'-GCACCATTGAAATCCTGAGTG-3';<br>SEQ ID NO: 11<br>5'-TCACAGAGGAAACTCTGCATTC-3';<br>SEQ ID NO: 13<br>5'-ATCTCCAGGGGCACCATT-3';<br>SEQ ID NO: 15 | 5'-GCAGACAGACACTGGCAACA-3';<br>SEQ ID NO: 10<br>5'-GCTCCCACTTTGTCTCCAGT-3';<br>SEQ ID NO: 12<br>5'-GGACACCCTCCAGGAAGC-3';<br>SEQ ID NO: 14<br>5'-AGCTGCACATCACTCAGGATT-3';<br>SEQ ID NO: 16 |
| RPL8 | 5'-ACTGCTGGCCACGAGTACG-3';<br>SEQ ID NO: 17<br>5'-ACAGAGCTGTGGTTGGTGTG-3';<br>SEQ ID NO: 19<br>5'-TATCTCCTCAGCCAACAGAGC-3';<br>SEQ ID NO: 21<br>5'-GTGTGGCCATGAATCCTGT-3';<br>SEQ ID NO: 23 | 5'-ATGCTCCACAGGATTCATGG-3';<br>SEQ ID NO: 18<br>5'-TTGTCAATTCGGCCACCT-3';<br>SEQ ID NO: 20<br>5'-AGCCACCACACCAACCAC-3';<br>SEQ ID NO: 22<br>5'-CCACCTCCAAAAGGATGCTC-3';<br>SEQ ID NO: 24 |
| B2M | 5'-TCTCTCTTTCTGGCCTGGAG-3';<br>SEQ ID NO: 25<br>5'-TGGAGGCTATCCAGCGTACT-3';<br>SEQ ID NO: 27<br>5'-CCAGCGTACTCCAAAGATTCA-3';<br>SEQ ID NO: 29<br>5'-GGCTATCCAGCGTACTCCAA-3';<br>SEQ ID NO: 31 | 5'-GAATCTTTGGAGTACGCTGGA-3';<br>SEQ ID NO: 26<br>5'-CGTGAGTAAACCTGAATCTTTGG-3';<br>SEQ ID NO: 28<br>5'-TCTCTGCTGGATGACGTGAG-3';<br>SEQ ID NO: 30<br>5'-GCTGGATGACGTGAGTAAACC-3';<br>SEQ ID NO: 32 |
| KRT14 | 5'-ACCATTGAGGACCTGAGGAA-3';<br>SEQ ID NO: 33<br>5'-CATTGAGGACCTGAGGAACA-3';<br>SEQ ID NO: 35<br>5'-GATGACTTCCGCACCAAGTA-3';<br>SEQ ID NO: 37<br>5'-TCCGCACCAAGTATGAGACA-3';<br>SEQ ID NO: 39 | 5'-GTCCACTGTGGCTGTGAGAA-3';<br>SEQ ID NO: 34<br>5'-AATCTGCAGAAGGACATTGG-3';<br>SEQ ID NO: 36<br>5'-CGCAGGTTCAACTCTGTCTC-3';<br>SEQ ID NO: 38<br>5'-ACTCATGCGCAGGTTCAACT-3';<br>SEQ ID NO: 40 |
| KRT10 | 5'-GAGCCTCGTGACTACAGCAA-3';<br>SEQ ID NO: 41<br>5'-AAAACCATCGATGACCTTAAAAA-3';<br>SEQ ID NO: 43 | 5'-GCAGGATGTTGGCATTATCAGT-3';<br>SEQ ID NO: 42<br>5'-GATCTGAAGCAGGATGTTGG-3';<br>SEQ ID NO: 44 |
| MITF | 5'-TTCCCAAGTCAAATGATCCAG-3';<br>SEQ ID NO: 45<br>5'-CGGCATTTGTTGCTCAGAAT-3';<br>SEQ ID NO: 47 | 5'-AAGATGGTTCCCTTGTTCCA-3';<br>SEQ ID NO: 46<br>5'-GAGCCTGCATTTCAAGTTCC-3';<br>SEQ ID NO: 48 |
| TYR | 5'-TTCCTTCTTCACCATGCATTT-3';<br>SEQ ID NO: 49<br>5'-TCCAAAGATCTGGGCTATGA-3';<br>SEQ ID NO: 51 | 5'-GGAGCCACTGCTCAAAAATA-3';<br>SEQ ID NO: 50<br>5'-TTGAAAAGAGTCTGGGTCTGAA-3';<br>SEQ ID NO: 52 |
| MLANA | 5'-GAGAAAAACTGTGAACCTGTGG-3';<br>SEQ ID NO: 53<br>5'-GAAGACGAAATGGATACAGAGC-3';<br>SEQ ID NO: 55 | 5'-ATAAGCAGGTGGAGCATTGG-3';<br>SEQ ID NO: 54<br>5'-GTGCCAACATGAAGACTTTTATC-3';<br>SEQ ID NO: 56 |
| PMEL | 5'-GTGGTCAGCACCCAGCTTAT-3';<br>SEQ ID NO: 57<br>5'-GCTGTGGTCCTTGCATCTCT-3';<br>SEQ ID NO: 59 | 5'-CCAAGGCCTGCTTCTTGAC-3';<br>SEQ ID NO: 58<br>5'-GCTTCATAAGTCTGCGCCTA-3';<br>SEQ ID NO: 60 |
| FN1 | 5'-CTCCTGCACATGCTTTGGA-3';<br>SEQ ID NO: 61<br>5'-AGGCTTTGGAAGTGGTCATT-3';<br>SEQ ID NO: 63<br>5'-GAAGTGGTCATTTCAGATGTGATT-3';<br>SEQ ID NO: 65<br>5'-TGGTCATTTCAGATGTGATTCAT-3';<br>SEQ ID NO: 67 | 5'-AGGTCTGCGGCAGTTGTC-3';<br>SEQ ID NO: 62<br>5'-CCATTGTCATGGCACCATCT-3';<br>SEQ ID NO: 64<br>5'-CCATTGTCATGGCACCATCT-3';<br>SEQ ID NO: 66<br>5'-CATTGTCATGGCACCATCTA-3';<br>SEQ ID NO: 68 |

TABLE 2-continued

Primer sets for indicated genes.

| Gene Name | Forward primer | Reverse primer |
|---|---|---|
| SPP1 | 5'-GTTTCGCAGACCTGACATCC-3'; SEQ ID NO: 69 | 5'-TCCTCGTCTGTAGCATCAGG-3'; SEQ ID NO: 70 |
| | 5'-CCTGACATCCAGTACCCTGA-3'; SEQ ID NO: 71 | 5'-TGAGGTGATGTCCTCGTCTG-3'; SEQ ID NO: 72 |
| | 5'-GAATCTCCTAGCCCCACAGA-3'; SEQ ID NO: 73 | 5'-GGTTTCTTCAGAGGACACAGC-3'; SEQ ID NO: 74 |
| | 5'-CCCATCTCAGAAGCAGAATCTC-3'; SEQ ID NO: 75 | 5'-ACAGCATTCTGTGGGGCTA-3'; SEQ ID NO: 76 |
| COL4A1 | 5'-GGAAAACCAGGACCCAGAG-3'; SEQ ID NO: 77 | 5'-CTTTTTCCCCTTTGTCACCA-3'; SEQ ID NO: 78 |
| | 5'-AGAAAGGTGAACCCGGAAAA-3'; SEQ ID NO: 79 | 5'-GGTTTGCCTCTGGGTCCT-3'; SEQ ID NO: 80 |
| | 5'-GAGAAAAGGGCCAAAAAGGT-3'; SEQ ID NO: 81 | 5'-CATCCCCTGAAATCCAGGTT-3'; SEQ ID NO: 82 |
| | 5'-AAAGGGCCAAAAAGGTGAAC-3'; SEQ ID NO: 83 | 5'-CCTGGCATCCCCTGAAAT-3'; SEQ ID NO: 84 |
| TNC | 5'-GTGTCAACCTGATGGGAGA-3'; SEQ ID NO: 85 | 5'-GTTAACGCCCTGACTGTGGT-3'; SEQ ID NO: 86 |
| | 5'-GGTACAGTGGGACAGCAGGT-3'; SEQ ID NO: 87 | 5'-GATCTGCCATTGTGGTAGGC-3'; SEQ ID NO: 88 |
| | 5'-AACCACAGTCAGGGCGTTA-3'; SEQ ID NO: 89 | 5'-GTTCGTGGCCCTTCCAGT-3'; SEQ ID NO: 90 |
| | 5'-AAGCTGAAGGTGGAGGGTA-3'; SEQ ID NO: 91 | 5'-GAGTCACCTGCTGTCCCACT-3'; SEQ ID NO: 92 |
| ITGA3 | 5'-TATTCCTCCGAACCAGCATC-3'; SEQ ID NO: 93 | 5'-CACCAGCTCCGAGTCAATGT-3'; SEQ ID NO: 94 |
| | 5'-CCACCATCAACATGGAGAAC-3'; SEQ ID NO: 95 | 5'-AGTCAATGTCCACAGAGAACCA-3'; SEQ ID NO: 96 |
| LOXL3 | 5'-CAACTGCCACATTGGTGATG-3'; SEQ ID NO: 97 | 5'-AAACCTCCTGTTGGCCTCTT-3'; SEQ ID NO: 98 |
| | 5'-TGACATCACGGATGTGAAGC-3'; SEQ ID NO: 99 | 5'-GGGTTGATGACAACCTGGAG-3'; SEQ ID NO: 100 |
| AGRN | 5'-TGTGACCGAGAGCGAGAAG-3'; SEQ ID NO: 101 | 5'-CAGGCTCAGTTCAAAGTGGTT-3'; SEQ ID NO: 102 |
| | 5'-CGGACCTTTGTCGAGTACCT-3'; SEQ ID NO: 103 | 5'-GTTGCTCTGCAGTGCCTTCT-3'; SEQ ID NO: 104 |
| VCAN | 5'-GACTTCCGTTGGACTGATGG-3'; SEQ ID NO: 105 | 5'-TGGTTGGGTCTCCAATTCTC-3'; SEQ ID NO: 106 |
| | 5'-ACGTGCAAGAAAGGAACAGT-3'; SEQ ID NO: 107 | 5'-TCCAAAGGTCTTGGCATTTT-3'; SEQ ID NO: 108 |
| PLOD3 | 5'-GCAGAGATGGAGCACTACGG-3'; SEQ ID NO: 109 | 5'-CAGCCTTGAATCCTCATGC-3'; SEQ ID NO: 110 |
| | 5'-GGAAGGAATCGTGGAGCAG-3'; SEQ ID NO: 111 | 5'-CAGCAGTGGGAACCAGTACA-3'; SEQ ID NO: 112 |
| ITGB1 | 5'-CTGATGAATGAAATGAGGAGGA-3'; SEQ ID NO: 113 | 5'-CACAAATGAGCCAAATCCAA-3'; SEQ ID NO: 114 |
| | 5'-CAGTTTGCTGTGTGTTTGCTC-3'; SEQ ID NO: 115 | 5'-CATGATTTGGCATTTGCTTTT-3'; SEQ ID NO: 116 |
| PTK2 | 5'-GCCCCACCAGAGGAGTATGT-3'; SEQ ID NO: 117 | 5'-AAGCCGACTTCCTTCACCA-3'; SEQ ID NO: 118 |
| | 5'-GAGACCATTCCCCTCCTACC-3'; SEQ ID NO: 119 | 5'-GCTTCTGTGCCATCTCAATCT-3'; SEQ ID NO: 120 |
| CTGF | 5'-CGAAGCTGACCTGGAAGAGA-3'; SEQ ID NO: 121 | 5'-TGGGAGTACGGATGCACTTT-3'; SEQ ID NO: 122 |
| | 5'-GTGTGCACCGCCAAAGAT-3'; SEQ ID NO: 123 | 5'-CGTACCACCGAAGATGCAG-3'; SEQ ID NO: 124 |
| PLOD1 | 5'-CTACCCCGGCTACTACACCA-3'; SEQ ID NO: 125 | 5'-GACAAAGGCCAGGTCAAACT-3'; SEQ ID NO: 126 |
| | 5'-AGTCGGGGTGGATTACGAG-3'; SEQ ID NO: 127 | 5'-ACAGTTGTAGCGCAGGAACC-3'; SEQ ID NO: 128 |
| LAMC1 | 5'-ATGATGATGGCAGGGATGG-3'; SEQ ID NO: 129 | 5'-GCATTGATCTCGGCTTCTTG-3'; SEQ ID NO: 130 |

TABLE 2-continued

Primer sets for indicated genes.

| Gene Name | Forward primer | Reverse primer |
|---|---|---|
| THBS1 | 5'-CTGTGGCACACAGGAAACAC-3';<br>SEQ ID NO: 131<br>5'-GCCAAAGACGGGTTTCATTA-3';<br>SEQ ID NO: 133 | 5'-ACGAGGGTCATGCCACAG-3';<br>SEQ ID NO: 132<br>5'-GCCATGATTTTCTTCCCTTC-3';<br>SEQ ID NO: 134 |
| LOXL2 | 5'-CTCCTCCTACGGCAAGGGA-3';<br>SEQ ID NO: 135<br>5'-CTCCTACGGCAAGGGAGAAG-3';<br>SEQ ID NO: 137 | 5'-TGGAGATTGTCTAACCAGATGGG-3';<br>SEQ ID NO: 136<br>5'-TTGCCAGTACAGTGGAGATTG-3';<br>SEQ ID NO: 138 |
| IL6 | 5'-CCAGAGCTGTGCAGATGAGT-3';<br>SEQ ID NO: 139 | 5'-TGCATCTAGATTCTTTGCCTTT-3';<br>SEQ ID NO: 140 |
| LOXL1 | 5'-AGGGCACAGCAGACTTCCT-3';<br>SEQ ID NO: 141<br>5'-GCATGCACCTCTCATACCC-3';<br>SEQ ID NO: 143 | 5'-TCGTCCATGCTGTGGTAATG-3';<br>SEQ ID NO: 142<br>5'-CGCATTGTAGGTGTCATAGCA-3';<br>SEQ ID NO: 144 |
| IL8 | 5'-CTTGGCAGCCTTCCTGATT-3';<br>SEQ ID NO: 145 | 5'-GCAAAACTGCACCTTCACAC-3';<br>SEQ ID NO: 146 |
| CYR61 | 5'-CGCTCTGAAGGGGATCTG-3';<br>SEQ ID NO: 147<br>5'-GAGCTCAGTCAGAGGGCAGA-3';<br>SEQ ID NO: 149 | 5'-ACAGGGTCTGCCCTCTGACT-3';<br>SEQ ID NO: 148<br>5'-AACTTTCCCCGTTTTGGTAGA-3';<br>SEQ ID NO: 150 |
| ITGAV | 5'-GACCTTGGAAACCCAATGAA-3';<br>SEQ ID NO: 431<br>5'-GGTGGTATGTGACCTTGGAAA-3';<br>SEQ ID NO: 439 | 5'-TCCATCTCTGACTGCTGGTG-3';<br>SEQ ID NO: 432<br>5'-GCACACTGAAACGAAGACCA-3';<br>SEQ ID NO: 440 |
| YAP | 5'-TGAACAGTGTGGATGAGATGG-3';<br>SEQ ID NO: 151 | 5'-GCAGGGTGCTTTGGTTGATA-3';<br>SEQ ID NO:152 |
| BGN | 5'-AAGGGTCTCCAGCACCTCTAC-3';<br>SEQ ID NO: 153<br>5'-GAGCTCCGCAAGGATGACT-3';<br>SEQ ID NO: 155 | 5'-AAGGCCTTCTCATGGATCTT-3';<br>SEQ ID NO: 154<br>5'-AGGACGAGGGCGTAGAGGT-3';<br>SEQ ID NO: 156 |
| LAMB1 | 5'-CATTCAAGGAACCCAGAACC-3';<br>SEQ ID NO: 157 | 5'-GCGTTGAACAAGGTTTCCTC-3';<br>SEQ ID NO: 158 |
| ITGB3 | 5'-AAGAGCCAGAGTGTCCCAAG-3';<br>SEQ ID NO: 159<br>5'-CTTCTCCTGTGTCCGCTACAA-3';<br>SEQ ID NO: 161<br>5'-TGCCTGCACCTTTAAGAAAGA-3';<br>SEQ ID NO: 163<br>5'-AAGGGGGAGATGTGCTCAG-3';<br>SEQ ID NO: 165 | 5'-ACTGAGAGCAGGACCACCA-3';<br>SEQ ID NO: 160<br>5'-CATGGCCTGAGCACATCTC-3';<br>SEQ ID NO: 162<br>5'-CCGGTCAAACTTCTTACACTCC-3';<br>SEQ ID NO: 164<br>5'-CAGTCCCCACAGCTGCAC-3';<br>SEQ ID NO: 166 |
| CXCL1 | 5'-AAACCGAAGTCATAGCCACAC-3';<br>SEQ ID NO: 167 | 5'-AAGCTTTCCGCCCATTCTT-3';<br>SEQ ID NO: 168 |
| THBS2 | 5'-AGGCCCAAGACTGGCTACAT-3';<br>SEQ ID NO: 169<br>5'-GGCAGGTGCGAACCTTATG-3';<br>SEQ ID NO: 171 | 5'-CTGCCATGACCTGTTTCCT-3';<br>SEQ ID NO: 170<br>5'-CCTTCCAGCCAATGTTCCT-3';<br>SEQ ID NO: 172 |
| COL18A1 | 5'-GATCGCTGAGCTGAAGGTG-3';<br>SEQ ID NO: 173 | 5'-CGGATGCCCCATCTGAGT-3';<br>SEQ ID NO: 174 |
| SPARC | 5'-CCCATTGGCGAGTTTGAGAAG-3';<br>SEQ ID NO: 175<br>5'-GGAAGAAACTGTGGCAGAGG-3';<br>SEQ ID NO: 177 | 5'-AGGAAGAGTCGAAGGTCTTGTT-3';<br>SEQ ID NO: 176<br>5'-GGACAGGATTAGCTCCCACA-3';<br>SEQ ID NO: 178 |
| TP53 | 5'-ACAACGTTCTGTCCCCCTTG-3';<br>SEQ ID NO: 179 | 5'-GGGGACAGCATCAAATCATC-3';<br>SEQ ID NO: 180 |
| PLOD2 | 5'-TGGATGCAGATGTTGTTTTGA-3';<br>SEQ ID NO: 181<br>5'-TTGATTGAACAAAACAGAAAGATCA-3';<br>SEQ ID NO: 183 | 5'-CACAGCTTTCCATGACGAGTT-3';<br>SEQ ID NO: 182<br>5'-TGACGAGTTACAAGAGGAGCAA-3';<br>SEQ ID NO: 184 |

TABLE 2-continued

Primer sets for indicated genes.

| Gene Name | Forward primer | Reverse primer |
| --- | --- | --- |
| CCL2 | 5'-CTGCTCATAGCAGCCACCTT-3';<br>SEQ ID NO: 185 | 5'-AGGTGACTGGGGCATTGATT-3';<br>SEQ ID NO: 186 |
| FBLN2 | 5'-ACGTGGAGGAGGACACAGAC-3';<br>SEQ ID NO: 187 | 5'-GGAGCCTTCAGGGCTACTTC-3';<br>SEQ ID NO: 188 |
| LAMA1 | 5'-AGCACTGCCAAAGTGGATG-3';<br>SEQ ID NO: 189 | 5'-TTGTTGACATGGAACAAGACC-3';<br>SEQ ID NO: 190 |
| THBS4 | 5'-GTGGGCTACATCAGGGTACG-3';<br>SEQ ID NO: 191<br>5'-CATCATCTGGTCCAACCTCA-3';<br>SEQ ID NO: 193 | 5'-CAGAGTCAGCCACCAACTCA-3';<br>SEQ ID NO: 192<br>5'-GTCCTCAGGGATGGTGTCAT-3';<br>SEQ ID NO: 194 |
| COL1A1 | 5'-TGACCTCAAGATGTGCCACT-3';<br>SEQ ID NO: 195<br>5'-GATGGATTCCAGTTCGAGTATG-3';<br>SEQ ID NO: 197 | 5'-TGGTTGGGGTCAATCCAGTA-3';<br>SEQ ID NO: 196<br>5'-ATCAGGCGCAGGAAGGTC-3';<br>SEQ ID NO: 198 |
| ITGA5 | 5'-CCCAAAAAGAGCGTCAGGT-3';<br>SEQ ID NO: 199 | 5'-TTGTTGACATGGAACAAGACC-3';<br>SEQ ID NO: 200 |
| TAZ | 5'-CTTCCTAACAGTCCGCCCTA-3';<br>SEQ ID NO: 201 | 5'-CCCGATCAGCACAGTGATTT-3';<br>SEQ ID NO: 202 |
| POSTN | 5'-CTGCTTCAGGGAGACACACC-3';<br>SEQ ID NO: 203<br>5'-AGGAAGTTGCAAGCCAACAA-3';<br>SEQ ID NO: 205 | 5'-TGGCTTGCAACTTCCTCAC-3';<br>SEQ ID NO: 204<br>5'-CGACCTTCCCTTAATCGTCTT-3';<br>SEQ ID NO: 206 |
| LOX | 5'-GCGGAGGAAAACTGTCTGG-3';<br>SEQ ID NO: 207<br>5'-ATATTCCTGGGAATGGCACA-3';<br>SEQ ID NO: 209 | 5'-AAATCTGAGCAGCACCCTGT-3';<br>SEQ ID NO: 208<br>5'-CCATACTGTGGTAATGTTGATGA-3';<br>SEQ ID NO: 210 |
| CSRC | 5'-TGTCAACAACACAGAGGGAGA-3';<br>SEQ ID NO: 211<br>5'-TGGCAAGATCACCAGACGG-3';<br>SEQ ID NO: 213 | 5'-CACGTAGTTGCTGGGGATGT-3';<br>SEQ ID NO: 212<br>5'-GGCACCTTTCGTGGTCTCAC-3';<br>SEQ ID NO: 214 |
| LAMA3 | 5'-CATGTCGTCTTGGCTCACTC-3';<br>SEQ ID NO: 215 | 5'-AAATTCTGGCCCCAACAATAC-3';<br>SEQ ID NO: 216 |
| CDKN1A | 5'-CATGTCGTCTTGGCTCACTC-3';<br>SEQ ID NO: 217 | 5'-AAATTCTGGCCCCAACAATAC-3';<br>SEQ ID NO: 218 |
| CDKN2A | 5'-AGGAGCCAGCGTCTAGGG-3';<br>SEQ ID NO: 219<br>5'-AACGCACCGAATAGTTACGG-3';<br>SEQ ID NO: 221 | 5'-CTGCCCATCATCATGACCT-3';<br>SEQ ID NO: 220<br>5'-CATCATCATGACCTGGATCG-3';<br>SEQ ID NO: 222 |
| ITGA2 | 5'-CACTGTTACGATTCCCCTGA-3';<br>SEQ ID NO: 223 | 5'-CGGCTTTCTCATCAGGI1TTC-3';<br>SEQ ID NO: 224 |
| LAMC2 | 5'-ATTAGACGGCCTCCTGCATC-3';<br>SEQ ID NO: 225 | 5'-AGACCAGCCCCTCTTCATCT-3';<br>SEQ ID NO: 226 |
| PCOLCE2 | 5'-TACTTGGAAAATCACAGTTCCCG-3';<br>SEQ ID NO: 443 | 5'-TGAATCGGAAATTGAGAACGACT-3';<br>SEQ ID NO: 444 |
| LOXL4 | 5'-GGCCCCGGGAATTATATCT-3';<br>SEQ ID NO: 227<br>5'-CTGCACAACTGCCACACAG-3';<br>SEQ ID NO: 229 | 5'-CCACTTCATAGTGGGGGTTC-3';<br>SEQ ID NO: 228<br>5'-GTTCTGCATTGGCTGGGTAT-3';<br>SEQ ID NO:230 |

TABLE 2-continued

Primer sets for indicated genes.

| Gene Name | Forward primer | Reverse primer |
|---|---|---|
| PCOLCE | 5'-CGTGGCAAGTGAGGGGTTC-3';<br>SEQ ID NO: 231<br>5'-GAGGCTTCCTGCTCTGGT-3';<br>SEQ ID NO: 233 | 5'-CGAAGACTCGGAATGAGAGGG-3';<br>SEQ ID NO: 232<br>5'-CGCAAAATTGGTGCTCAGT-3';<br>SEQ ID NO: 234 |
| LAMB3 | 5'-GTCCGGGACTTCCTAACAGA-3';<br>SEQ ID NO: 235 | 5'-GCTGACCTCCTGGATAGTGG-3';<br>SEQ ID NO: 236 |
| PMEL | 5'-GTGGTCAGCACCCAGCTTAT-3';<br>SEQ ID NO: 237<br>5'-GCTGTGGTCCTTGCATCTCT-3';<br>SEQ ID NO: 239 | 5'-CCAAGGCCTGCTTCTTGAC-3';<br>SEQ ID NO: 238<br>5'-GCTTCATAAGTCTGCGCCTA-3';<br>SEQ ID NO: 240 |
| NES | 5'-CTTCCCTCAGCTTTCAGGAC-3';<br>SEQ ID NO: 241<br>5'-ACCTCAAGATGTCCCTCAGC-3';<br>SEQ ID NO: 243 | 5'-TCTGGGGTCCTAGGGAATTG-3';<br>SEQ ID NO: 242<br>5'-CAGGAGGGTCCTGTACGTG-3';<br>SEQ ID NO: 244 |
| L1CAM | 5'-GAGACCTTCGGCGAGTACAG-3';<br>SEQ ID NO: 245<br>5'-GGCGGCAAATACTCAGTGAA-3';<br>SEQ ID NO: 247 | 5'-AAAGGCCTTCTCCTCGTTGT-3';<br>SEQ ID NO: 246<br>5'-CCTGGGTGTCCTCCTTATCC-3';<br>SEQ ID NO: 248 |
| GDF15 | 5'-CGGATACTCACGCCAGAAGT-3';<br>SEQ ID NO: 249<br>5'-AAGATTCGAACACCGACCTC-3';<br>SEQ ID NO: 251 | 5'-AGAGATACGCAGGTGCAGGT-3';<br>SEQ ID NO: 250<br>5'-GCACTTCTGGCGTGAGTATC-3';<br>SEQ ID NO:252 |
| ARPC1B | 5'-CACGCCTGGAACAAGGAC-3';<br>SEQ ID NO: 253<br>5'-CAGGTGACAGGCATCGACT-3';<br>SEQ ID NO: 255 | 5'-ATGCACCTCATGGTTGTTGG-3';<br>SEQ ID NO:254<br>5'-CGCAGGTCACAATACGGTTA-3';<br>SEQ ID NO: 256 |
| FARP1 | 5'-TGAGGCCCTGAGAGAGAAGA-3';<br>SEQ ID NO: 257<br>5'-TCAAGGAAATTGAGCAACGA-3';<br>SEQ ID NO: 259 | 5'-ATTCCGAAACTCCACACGTC-3';<br>SEQ ID NO: 258<br>5'-TCTGATTTGGGCATTTGAGC-3';<br>SEQ ID NO: 260 |
| NTRK3 | 5'-TATGGTCGACGGTCCAAAT-3';<br>SEQ ID NO: 261<br>5'-CACTGTGACCCACAAACCAG-3';<br>SEQ ID NO: 263 | 5'-TCCTCACCACTGATGACAGC-3';<br>SEQ ID NO: 262<br>5'-GCAAGTCCAACTGCTATGGA-3';<br>SEQ ID NO: 264 |
| CSK | 5'-TGAGGCCCTGAGAGAGAAGA-3';<br>SEQ ID NO: 265<br>5'-TCTACTCCTTTGGGCGAGTG-3';<br>SEQ ID NO: 267 | 5'-ATTCCGAAACTCCACACGTC-3';<br>SEQ ID NO: 266<br>5'-CGTCCTTCAGGGGAATTCTT-3';<br>SEQ ID NO: 268 |
| CD44 | 5'-TAAGGACACCCCAAATTCCA-3';<br>SEQ ID NO: 269<br>5'-GCAGTCAACAGTCGAAGAAGG-3';<br>SEQ ID NO: 271 | 5'-GCCAAGATGATCAGCCATTC-3';<br>SEQ ID NO: 270<br>5'-AGCTTTTTCTTCTGCCCACA-3';<br>SEQ ID NO: 272 |
| SNX17 | 5'-AGCCAGCAAGCAGTGAAGTC-3';<br>SEQ ID NO: 273<br>5'-CCGGGAGTCTATGGTCAAAC-3';<br>SEQ ID NO: 275 | 5'-TCAGGTGACTCAAGCAGTGG-3';<br>SEQ ID NO: 274<br>5'-CACGGCACTCAGCTTACTTG-3';<br>SEQ ID NO: 276 |
| PLAT | 5'-TGGAGCAGTCTTCGTTTCG-3';<br>SEQ ID NO: 277<br>5'-GCCCGATTCAGAAGAGGAG-3';<br>SEQ ID NO: 279 | 5'-CTGGCTCCTCTTCTGAATCG-3';<br>SEQ ID NO: 278<br>5'-TCATCTCTGCAGATCACTTGG-3';<br>SEQ ID NO: 280 |

The following was performed to generate a standard curve for the target of each primer pair. The standard was generated with a defined number of amplicons per volume for each primer pair. In particular, a standard (S7) was designed to contain about 5 million copies of amplicon-containing cDNA in a bacterial expression vector backbone (pJET1.2 obtained from Fermentas) per one microliter volume for each primer pair. From this, six 1:10 dilutions were generated such that seven standards S1 to S7 were obtained ranging from 5 to 5 million copies of amplicon. To obtain fragments of cDNA, total RNA was extracted from the human HaCaT, A431, and A375 cell lines, and the RNA was reverse transcribed into cDNA. Cell line-derived cDNA was used as a template to amplify fragments of cDNA that contained the desired amplicons for the real time-PCR primer pairs. A list of primers used to generate the desired cDNA fragments is listed in Table 3.

TABLE 3

Primer sets for generating cDNA fragments of the indicated genes.

| Gene Name | Forward primer | Reverse primer |
| --- | --- | --- |
| FN1 | 5'-CCAGCAGAGGCATAAGGTTC-3';<br>SEQ ID NO: 281 | 5'-AGTAGTGCCTTCGGGACTGG-3';<br>SEQ ID NO: 282 |
| SPP1 | 5'-AGGCTGATTCTGGAAGTTCTGAGG-3';<br>SEQ ID NO: 283 | 5'-AATCTGGACTGCTTGTGGCTG-3';<br>SEQ ID NO: 284 |
| COL4A1 | 5'-GTTGGGCCTCCAGGATTTA-3';<br>SEQ ID NO: 285 | 5'-GCCTGGTAGTCCTGGGAAAC-3';<br>SEQ ID NO: 286 |
| TNC | 5'-TGGATGGATTGTGTTCCTGA-3';<br>SEQ ID NO: 287 | 5'-GCCTGCCTTCAAGATTTCTG-3';<br>SEQ ID NO: 288 |
| ITGA3 | 5'-CTGAGACTGTGCTGACCTGTG-3';<br>SEQ ID NO: 289 | 5'-CTCTTCATCTCCGCCTTCTG-3';<br>SEQ ID NO: 290 |
| LOXL3 | 5'-GAGACCGCCTACATCGAAGA-3';<br>SEQ ID NO: 291 | 5'-GGTAGCGTTCAAACCTCCTG-3';<br>SEQ ID NO: 292 |
| AGRN | 5'-ACACCGTCCTCAACCTGAAG-3';<br>SEQ ID NO: 293 | 5'-AATGGCCAGTGCCACATAGT-3';<br>SEQ ID NO: 294 |
| VCAN | 5'-GGTGCACTTTGTGAGCAAGA-3';<br>SEQ ID NO: 295 | 5'-TTGGTATGCAGATGGGTTCA-3';<br>SEQ ID NO: 296 |
| PLOD3 | 5'-AGCTGTGGTCCAACTTCTGG-3';<br>SEQ ID NO: 297 | 5'-GTGTGGTAACCGGGAAACAG-3';<br>SEQ ID NO: 298 |
| ITGB1 | 5'-TTCAGTTTGCTGTGTGTTTGC-3';<br>SEQ ID NO: 299 | 5'-CCACCTTCTGGAGAATCCAA-3';<br>SEQ ID NO: 300 |
| PTK2 | 5'-GGCAGTATTGACAGGGAGGA-3';<br>SEQ ID NO: 301 | 5'-TACTCTTGCTGGAGGCTGGT-3';<br>SEQ ID NO: 302 |
| CTGF | 5'-GCCTATTCTGTCACTTCGGCTC-3';<br>SEQ ID NO: 303 | 5'-GCAGGCACAGGTCTTGATGAAC-3';<br>SEQ ID NO: 304 |
| PLOD1 | 5'-GACCTCTGGGAGGTGTTCAG-3';<br>SEQ ID NO: 305 | 5'-TTAGGGATCGACGAAGGAGA-3';<br>SEQ ID NO: 306 |
| LAMC1 | 5'-ATTCCTGCCATCAACCAGAC-3';<br>SEQ ID NO: 307 | 5'-CCTGCTTCTTGGCTTCATTC-3';<br>SEQ ID NO: 308 |
| THBS1 | 5'-CAAAGGGACATCCCAAAATG-3';<br>SEQ ID NO: 309 | 5'-GAGTCAGCCATGATTTTCTTCC-3';<br>SEQ ID NO: 310 |
| LOXL2 | 5'-TACCCCGAGTACTTCCAGCA-3';<br>SEQ ID NO: 311 | 5'-GATCTGCTTCCAGGTCTTGC-3';<br>SEQ ID NO: 312 |
| IL6 | 5'-CACACAGACAGCCACTCACC-3';<br>SEQ ID NO: 313 | 5'-CAGGGGTGGTTATTGCATCT-3';<br>SEQ ID NO: 314 |
| LOXL1 | 5'-CAGACCCCAACTATGTGCAA-3';<br>SEQ ID NO: 315 | 5'-CGCATTGTAGGTGTCATAGCA-3';<br>SEQ ID NO: 316 |
| IL8 | 5'-CTCTCTTGGCAGCCTTCCT-3';<br>SEQ ID NO: 317 | 5'-TGAATTCTCAGCCCTCTTCAA-3';<br>SEQ ID NO: 318 |
| CYR61 | 5'-TCGCCTTAGTCGTCACCCTT-3';<br>SEQ ID NO: 319 | 5'-TGTTTCTCGTCAACTCCACCTCG-3';<br>SEQ ID NO: 320 |
| ITGAV | 5'-CTGATTTCATCGGGGTTGTC-3';<br>SEQ ID NO: 321 | 5'-TGCCTTGCTGAATGAACTTG-3';<br>SEQ ID NO: 322 |
| YAP | 5'-CCAGTGAAACAGCCACCAC-3';<br>SEQ ID NO: 323 | 5'-CTCCTTCCAGTGTTCCAAGG-3';<br>SEQ ID NO: 324 |
| BGN | 5'-GGACTCTGTCACACCCACCT-3';<br>SEQ ID NO: 325 | 5'-CAGGGTCTCAGGGAGGTCTT-3';<br>SEQ ID NO: 326 |
| LAMB1 | 5'-TGCCAGAGCTGAGATGTTGTT-3';<br>SEQ ID NO: 327 | 5'-TGTAGCATTTCGGCTTTCCT-3';<br>SEQ ID NO: 328 |
| ITGB3 | 5'-GGCAAGTACTGCGAGTGTGA-3';<br>SEQ ID NO: 329 | 5'-ATTCTTTCGGTCGTGGATG-3';<br>SEQ ID NO: 330 |

TABLE 3-continued

Primer sets for generating cDNA fragments of the indicated genes.

| Gene Name | Forward primer | Reverse primer |
|---|---|---|
| CXCL1 | 5'-CACTGCTGCTCCTGCTCCT-3';<br>SEQ ID NO: 331 | 5'-TGTTCAGCATCTTTTCGATGA-3';<br>SEQ ID NO: 332 |
| THBS2 | 5'-TGACAATGACAACATCCCAGA-3';<br>SEQ ID NO: 333 | 5'-TGAGTCTGCCATGACCTGTT-3';<br>SEQ ID NO: 334 |
| COL18A1 | 5'-CCCTGCTCTACACAGAACCAG-3';<br>SEQ ID NO: 335 | 5'-ACACCTGGCTCCCCTTTCT-3';<br>SEQ ID NO: 336 |
| SPARC | 5'-GCCTGGATCTTCTTTCTCCTTTGC-3';<br>SEQ ID NO: 337 | 5'-CATCCAGGGCGATGTACTTGTC-3';<br>SEQ ID NO: 338 |
| TP53 | 5'-CCCCCTCTGAGTCAGGAAAC-3';<br>SEQ ID NO: 339 | 5'-TCATGTGCTGTGACTGCTTG-3';<br>SEQ ID NO: 340 |
| PLOD2 | 5'-TGGACCCACCAAGATTCTCCTG-3';<br>SEQ ID NO: 341 | 5'-GACCACAGCTTTCCATGACGAG-3';<br>SEQ ID NO: 342 |
| CCL2 | 5'-TCTGTGCCTGCTGCTCATAG-3';<br>SEQ ID NO: 343 | 5'-GAGTTTGGGTTTGCTTGTCC-3';<br>SEQ ID NO: 344 |
| FBLN2 | 5'-CGAGAAGTGCCCAGGAAG-3';<br>SEQ ID NO: 345 | 5'-AGTGAGAAGCCAGGAAAGCA-3';<br>SEQ ID NO: 346 |
| LAMA1 | 5'-TGGAAATATCACCCACAGCA-3';<br>SEQ ID NO: 347 | 5'-AGGCATTTTTGCTTCACACC-3';<br>SEQ ID NO: 348 |
| THBS4 | 5'-GCTCCAGCTTCTACGTGGTC-3';<br>SEQ ID NO: 349 | 5'-TTAATTATCGAAGCGGTCGAA-3';<br>SEQ ID NO: 350 |
| COL1A1 | 5'-AGCCAGCAGATCGAGAACAT-3';<br>SEQ ID NO: 351 | 5'-CCTTCTTGAGGTTGCCAGTC-3';<br>SEQ ID NO: 352 |
| ITGA5 | 5'-CACCAATCACCCCATTAACC-3';<br>SEQ ID NO: 353 | 5'-GCTTGAGCTGAGCTTTTCC-3';<br>SEQ ID NO: 354 |
| TAZ | 5'-CCAGGTGCTGGAAAAAGAAG-3';<br>SEQ ID NO: 355 | 5'-GAGCTGCTCTGCCTGAGTCT-3';<br>SEQ ID NO: 356 |
| POSTN | 5'-GCAGACACACCTGTTGGAAA-3';<br>SEQ ID NO: 357 | 5'-GAACGACCTTCCCTTAATCG-3';<br>SEQ ID NO: 358 |
| LOX | 5'-CCTACTACATCCAGGCGTCCAC-3';<br>SEQ ID NO: 359 | 5'-ATGCAAATCGCCTGTGGTAGC-3';<br>SEQ ID NO: 360 |
| CSRC | 5'-CTGTTCGGAGGCTTCAACTC-3';<br>SEQ ID NO: 361 | 5'-AGGGATCTCCCAGGCATC-3';<br>SEQ ID NO: 362 |
| LAMA3 | 5'-TACCTGGGATCACCTCCATC-3';<br>SEQ ID NO: 363 | 5'-ACAGGGATCCTCAGTGTCGT-3';<br>SEQ ID NO: 364 |
| CDKN1A | 5'-CGGGATGAGTTGGGAGGAG-3';<br>SEQ ID NO: 365 | 5'-TTAGGGCTTCCTCTTGGAGA-3';<br>SEQ ID NO: 366 |
| CDKN2A-<br>004 2A-201 | 5'-ATGGTGCGCAGGTTCTTG-3';<br>SEQ ID NO: 367 | 5'-ACCAGCGTGTCCAGGAAG-3';<br>SEQ ID NO: 368 |
| CDKN2A-<br>001 2A-202 | 5'-GAGCAGCATGGAGCCTTC-3';<br>SEQ ID NO: 369 | 5'-GCATGGTTACTGCCTCTGGT-3';<br>SEQ ID NO: 370 |
| ITGA2 | 5'-CAAACAGACAAGGCTGGTGA-3';<br>SEQ ID NO: 371 | 5'-TCAATCTCATCTGGATTTTGG-3';<br>SEQ ID NO: 372 |
| LAMC2 | 5'-CTGCAGGTGGACAACAGAAA-3';<br>SEQ ID NO: 373 | 5'-CATCAGCCAGAATCCCATCT-3';<br>SEQ ID NO: 374 |
| PCOLCE2 | 5'-GTCCCCAGAGAGACCTGTTT-3';<br>SEQ ID NO: 375 | 5'-AGACACAATTGGCGCAGGT-3';<br>SEQ ID NO: 376 |
| LOXL4 | 5'-AAGACTGGACGCGATAGCTG-3';<br>SEQ ID NO: 377 | 5'-GGTTGTTCCTGAGACGCTGT-3';<br>SEQ ID NO: 378 |
| PCOLCE | 5'-TACACCAGACCCGTGTTCCT-3';<br>SEQ ID NO: 379 | 5'-TCCAGGTCAAACTTCTCGAAGG-3';<br>SEQ ID NO: 380 |

TABLE 3-continued

Primer sets for generating cDNA fragments of the indicated genes.

| Gene Name | Forward primer | Reverse primer |
| --- | --- | --- |
| LAMB3 | 5'-CTTCAATGCCCAGCTCCA-3';<br>SEQ ID NO: 381 | 5'-TTCCCAACCACATCTTCCAC-3';<br>SEQ ID NO: 382 |
| CSF2 | 5'-CTGCTGCTCTTGGGCACT-3';<br>SEQ ID NO: 383 | 5'-CAGCAGTCAAAGGGGATGAC-3';<br>SEQ ID NO: 384 |
| ACTB | 5'-AGGATTCCTATGTGGGCGACG-3';<br>SEQ ID NO: 385 | 5'-TCAGGCAGCTCGTAGCTCTTC-3';<br>SEQ ID NO: 386 |
| RPLP0 | 5'-GGAATGTGGGCTTTGTGTTCACC-3';<br>SEQ ID NO: 387 | 5'-AGGCCAGGACTCGTTTGTACC-3';<br>SEQ ID NO: 388 |
| RPL8 | 5'-ACATCAAGGGCATCGTCAAGG-3';<br>SEQ ID NO: 389 | 5'-TCTCTTTCTCCTGCACAGTCTTGG-3';<br>SEQ ID NO: 390 |
| B2M | 5'-TGCTCGCGCTACTCTCTCTTTC-3';<br>SEQ ID NO: 391 | 5'-TCACATGGTTCACACGGCAG-3';<br>SEQ ID NO: 392 |
| K10 | 5'-TGGCCTTCTCTCTGGAAATG-3';<br>SEQ ID NO: 393 | 5'-TCATTTCCTCCTCGTGGTTC-3';<br>SEQ ID NO: 394 |
| K14 | 5'-AGGTGACCATGCAGAACCTC-3';<br>SEQ ID NO: 395 | 5'-CCTCGTGGTTCTTCTTCAGG-3';<br>SEQ ID NO: 396 |
| MITF | 5'-GAAATCTTGGGCTTGATGGA-3';<br>SEQ ID NO: 397 | 5'-CCGAGGTTGTTGTTGAAGGT-3';<br>SEQ ID NO: 398 |
| TYR | 5'-CCATGGATAAAGCTGCCAAT-3';<br>SEQ ID NO: 399 | 5'-GACACAGCAAGCTCACAAGC-3';<br>SEQ ID NO: 400 |
| MLANA | 5'-CACTCTTACACCACGGCTGA-3';<br>SEQ ID NO: 401 | 5'-CATAAGCAGGTGGAGCATTG-3';<br>SEQ ID NO: 402 |
| PMEL | 5'-TTGTCCAGGGTATTGAAAGTGC-3';<br>SEQ ID NO: 403 | 5'-GACAAGAGCAGAAGATGCGGG-3';<br>SEQ ID NO: 404 |
| NES | 5'-GCGTTGGAACAGAGGTTGGAG-3';<br>SEQ ID NO: 405 | 5'-CAGGTGTCTCAAGGGTAGCAGG-3';<br>SEQ ID NO: 406 |
| L1CAM | 5'-CTTCCCTTTCGCCACAGTATG-3';<br>SEQ ID NO: 407 | 5'-CCTCCTTCTCCTTCTTGCCACT-3';<br>SEQ ID NO: 408 |
| GDF15 | 5'-AATGGCTCTCAGATGCTCCTGG-3';<br>SEQ ID NO: 409 | 5'-GATTCTGCCAGCAGTTGGTCC-3';<br>SEQ ID NO: 410 |
| ARPC1B | 5'-ACCACAGCTTCCTGGTGGAG-3';<br>SEQ ID NO: 411 | 5'-GAGCGGATGGGCTTCTTGATG-3';<br>SEQ ID NO: 412 |
| FARP1 | 5'-AACGTGACCTTGTCTCCCAAC-3';<br>SEQ ID NO: 413 | 5'-GCATGACATCGCCGATTCTT-3';<br>SEQ ID NO: 414 |
| NTRK3 | 5'-TTCAACAAGCCCACCCACTAC-3';<br>SEQ ID NO: 415 | 5'-GTTCTCAATGACAGGGATGCG-3';<br>SEQ ID NO: 416 |
| CSK | 5'-CATGGAATACCTGGAGGGCAAC-3';<br>SEQ ID NO: 417 | 5'-CAGGTGCCAGCAGTTCTTCAT-3';<br>SEQ ID NO: 418 |
| CD44 | 5'-TCTCAGAGCTTCTCTACATCAC-3';<br>SEQ ID NO: 419 | 5'-CTGACGACTCCTTGTTCACCA-3';<br>SEQ ID NO: 420 |
| SNX17 | 5'-TCACCTCCTCTGTACCATTGC-3';<br>SEQ ID NO: 421 | 5'-CTCATCTCCAATGCCCTCGA-3';<br>SEQ ID NO: 422 |
| PLAT | 5'-TGCAATGAAGAGAGGGCTCTG-3';<br>SEQ ID NO: 423 | 5'-CGTGGCCCTGGTATCTATTTCA-3';<br>SEQ ID NO: 424 |

The PCR reactions were performed using a high-fidelity polymerase (product name: "Phusion," obtained from New England Biolabs). PCR amplification products were checked for correct size and subsequently gel purified using the QIAGEN® Gel Extraction kit. Purified PCR fragments were subcloned into the bacterial expression vector pJET1.2 using a commercially available kit (Fermentas). The subcloned fragments were subsequently checked by restriction digest and DNA sequencing. Bacterial clones harboring the pJET1.2 expression vector with the correct PCR insert (containing the desired amplicon for real time PCR primer pairs) were frozen and stored at −80° C. This was done to regenerate the same real time PCR standards over time.

Bacteria harboring the pJET1.2 expression vector with PCR inserts were cultured to generate sufficient amounts of vector. A small aliquot of the total retrieved expression vector with insert was linearized using the PvuI-HF restriction enzyme (from New England Biolabs). The digest was then purified using the QIAGEN® PCR purification kit. Linearized cDNA was diluted to a concentration of 20 ng/µL. One µL of each of a total of 71 linearized cDNA fragments (each at a 20 ng/µL concentration) were mixed and brought to a final volume of 1 mL to obtain standard S7.

Standard S7 was then diluted six times at a 1:10 ratio to obtained standards 51 to S6. Dilution was performed using ultrapure water obtained from Promega (Cat. No. P1193).

The following was performed to generate cDNA from FFPE samples. FFPE blocks were cut at 20 µm sections using a standard Leica microtome. For large pieces of tissue, 2×20 µm full sections were used for RNA retrieval. For smaller tissues, up to 5×20 µm sections were combined for RNA retrieval. RNA extraction was performed using the QIAGEN® RNA FFPE retrieval kit and a QIAGEN® QIA-CUBE® extraction robot. 0.5 to 1 µg of RNA with a 260/280 ratio of greater than 1.8 were transcribed into cDNA using the BioRad iScript cDNA Synthesis kit. All biospecimens were annotated with clinical data from Mayo Clinic databases. H&E stained sections were obtained for each block analyzed and digitalized using a high-resolution slide scanner.

Fluidigm RT-PCR was performed using a 96×96 format for high-throughput analysis (i.e., 96 cDNAs were analyzed for 96 markers; 9216 data points). The primer pairs and cDNAs were prepared in a 96-well format. Standard curves were calculated for each primer pair. Copy numbers per 100,000 housekeeping genes were calculated for each primer pair and averaged per gene. This was initially done for cDNAs derived from FFPE-embedded skin. To correct for epidermal cell-derived cross-contamination, background signal per one copy of K14 (a basal keratinocyte marker) was calculated from FFPE-embedded normal skin samples for each primer pair and averaged. Experimental samples were then normalized first to 100,000 housekeeping genes and then background-corrected for epidermal cross-contamination based on K14 copy number. In particular, the keratinocyte correction factor used for each gene is set forth in Table E under the column titled "AVG per copy K14."

The study design (Example 1) involved a comparison of the expression profile of "true" benign pigmented skin lesions (nevi, n=73) with "true" malignant melanomas of the skin. The latter comprised i) primary skin melanomas that were documented to metastasize, either to regional lymph nodes, to other areas of skin (in-transit), or to other organs; and ii) in-transit or comparison of nevi to in-transit melanoma metastases (n=54).

Tables C and D summarize the comparisons of the gene expressions between the 73 benign and 54 metastatic. Table A compares the ranked values using the Wilcoxon rank sum test, and Table E compares the dichotomized values (zero vs. >0) using the chi-square test.

A recursive partitioning approach was used to identify cut-points for the genes that would discriminate between these two groups. After partitioning the data at a cut-point of 45 for FN1, no further additional splits in the data based on the other genes were identified by this method.

Using a cutoff of 45 for FN1, the sensitivity was 92.6%, and the specificity was 98.6%. These results are provided in Tables 4 and 5 along with the next possible cutoff for FN1 at 124.

TABLE 4

| Frequency Percent Row Pct Col Pct | Malignant | Benign | Total |
|---|---|---|---|
| FN1 < 45 | 4 | 72 | 76 |
| | 3.15 | 56.69 | 59.84 |
| | 5.26 | 94.74 | |
| | 7.41 | 98.63 | |
| FN1 ≥ 45 | 50 | 1 | 51 |
| | 39.37 | 0.79 | 40.16 |
| | 98.04 | 1.96 | |
| | 92.59 | 1.37 | |
| Total | 54 | 73 | 127 |
| | 42.52 | 57.48 | 100.00 |

TABLE 5

| Frequency Percent Row Pct Col Pct | Malignant | Benign | Total |
|---|---|---|---|
| FN1 < 124 | 8 | 73 | 81 |
| | 6.30 | 57.48 | 63.78 |
| | 9.88 | 90.12 | |
| | 14.81 | 100.00 | |
| FN1 ≥ 124 | 46 | 0 | 46 |
| | 36.22 | 0.00 | 36.22 |
| | 100.00 | 0.00 | |
| | 85.19 | 0.00 | |
| Total | 54 | 73 | 127 |
| | 42.52 | 57.48 | 100.00 |

The ability to further discriminate between the groups was assessed by considering SPP1 or ITGB3 in addition to FN1. Benign Vs. Malignant—Option 1 Using FN1 and SPP1 (FIG. 5)

The results are set forth in Table 6.

TABLE 6

Figure 5:
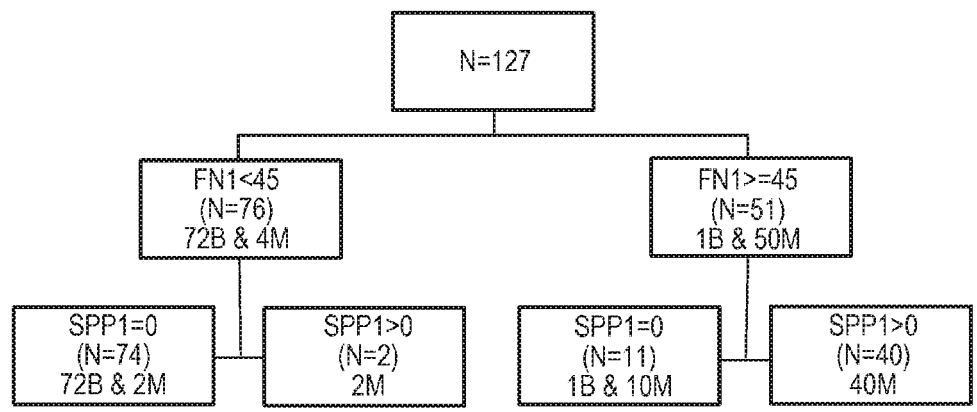
FIG. 5 is a flow chart of an exemplary process for using FN1 and SPP1 expression levels to determine the benign or malignant nature of a skin lesion.

| RULE for FIG. 5 | Malignant | Benign |
|---|---|---|
| FN1 < 45 and SPP1 = 0 | 2 | 72 |
| FN1 ≥ 45 or (FN1 < 45 and SPP1 > 0) | 52 | 1 |
| Total | 54 | 73 |

Benign Vs. Malignant—Option 2 Using FN1 and ITGB3 (FIG. 6)

The results are set forth in Table 7.

TABLE 7

Figure 6:
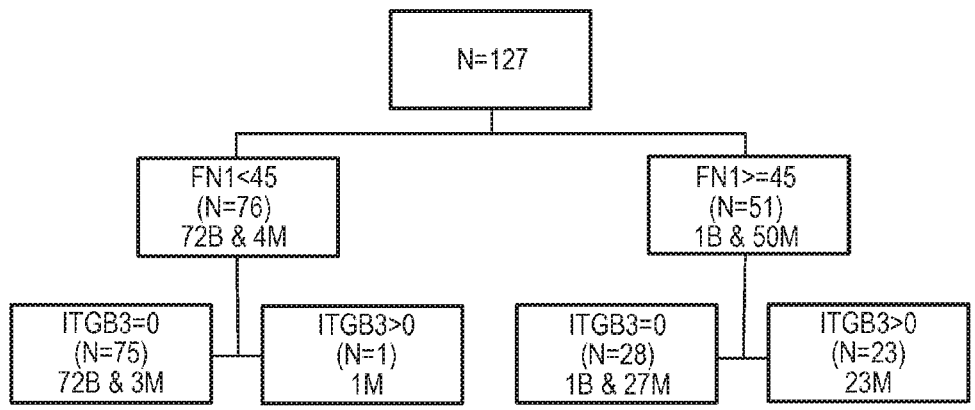
FIG. 6 is a flow chart of an exemplary process for using FN1 and ITGB3 expression levels to determine the benign or malignant nature of a skin lesion.

| RULE for FIG. 6 | Malignant | Benign |
|---|---|---|
| FN1 < 45 and ITGB3 = 0 | 3 | 72 |
| FN1 ≥ 45 or (FN1 < 45 and ITGB3 > 0) | 51 | 1 |
| Total | 54 | 73 |

If all three genes are included, the rule was as follows:

FN1<45 and SPP1=0 and ITGB3=0 denotes a negative test vs. all other combinations denotes a positive test.

This rule resulted in a specificity of 72/73 (98.6%), and a sensitivity of 53/54 (98.2%) (Table 8). Compared to a rule using FN1 alone, the specificity stayed the same but the sensitivity increased from 92.6% to 98.2% using this new rule.

TABLE 8

| FN1 | SPP1 | ITGB3 | malignant | Frequency | |
|---|---|---|---|---|---|
| <45 | Zero | Zero | No | 72 | |
| <45 | Zero | Zero | Yes | 1 | False Neg ID MM150 (case added from the Breslow file) |
| ≥45 | Zero | Zero | No | 1 | False Pos ID N29 |
| ≥45 | Zero | Zero | Yes | 9 | |
| ≥45 | Zero | >0 | Yes | 1 | |
| ≥45 | >0 | Zero | Yes | 18 | |
| ≥45 | >0 | >0 | Yes | 22 | |
| <45 | Zero | >0 | Yes | 1 | |
| <45 | >0 | Zero | Yes | 2 | |

The rule was evaluated using 25 additional malignant patients who did not have mets (from the "Breslow" file). For 19 of these 25 patients, the rule was "negative" (Table 9).

TABLE 9

| FN1 | SPP1 | ITGB3 | Frequency |
|---|---|---|---|
| <45 | Zero | Zero | 19 |
| <45 | >0 | Zero | 1 |
| ≥45 | Zero | Zero | 2 |
| ≥45 | >0 | Zero | 3 |
| <45 | | | 1 |

The rule also was evaluated using 33 thin melanomas (Table 10). For 25 of these 33 patients, the rule was "negative."

TABLE 10

| FN1 | SPP1 | ITGB3 | Frequency |
|---|---|---|---|
| <45 | Zero | Zero | 25 |
| <45 | Zero | >0 | 1 |
| ≥45 | Zero | Zero | 5 |
| ≥45 | >0 | Zero | 2 |

TABLE C

Comparison of gene expression between benign and malignant

| | Benign (N = 73) | Malignant (N = 54) | p value |
|---|---|---|---|
| CXCL1_AVG_NORM | | | <0.0001 |
| N | 73 | 54 | |
| Mean (SD) | 4.8 (18.4) | 20.0 (26.1) | |
| Median | 0.0 | 10.3 | |
| Q1, Q3 | 0.0, 0.0 | 0.3, 31.1 | |
| Range | (0.0-141.7) | (0.0-120.4) | |
| CSF2_AVG_NORM | | | 0.0482 |
| N | 73 | 54 | |
| Mean (SD) | 10.5 (44.1) | 4.3 (8.4) | |
| Median | 2.5 | 1.0 | |
| Q1, Q3 | 0.6, 7.0 | 0.0, 4.0 | |
| Range | (0.0-375.0) | (0.0-41.0) | |
| CCL2_AVG_NORM | | | <0.0001 |
| N | 73 | 54 | |
| Mean (SD) | 37.0 (99.4) | 244.2 (360.9) | |
| Median | 0.0 | 112.8 | |
| Q1, Q3 | 0.0, 9.1 | 7.2, 342.2 | |
| Range | (0.0-572.0) | (0.0-1777.1) | |
| IL8_AVG_NORM | | | <0.0001 |
| N | 73 | 54 | |
| Mean (SD) | 125.5 (671.3) | 53.2 (160.8) | |
| Median | 0.0 | 13.0 | |
| Q1, Q3 | 0.0, 0.0 | 2.1, 52.5 | |
| Range | (0.0-5058.7) | (0.0-1171.7) | |
| IL6_AVG_NORM | | | <0.0001 |
| N | 73 | 54 | |
| Mean (SD) | 9.9(69.1) | 21.6(35.0) | |
| Median | 0.0 | 8.8 | |
| Q1, Q3 | 0.0, 0.0 | 0.3, 25.2 | |
| Range | (0.0-589.1) | (0.0-152.3) | |
| ITGA5_AVG_NORM | | | <0.0001 |
| N | 73 | 54 | |
| Mean (SD) | 0.0 (0.0) | 9.8 (26.8) | |
| Median | 0.0 | 0.0 | |
| Q1, Q3 | 0.0, 0.0 | 0.0, 7.0 | |
| Range | (0.0-0.0) | (0.0-168.0) | |
| ITGA3_AVG_NORM | | | <0.0001 |
| N | 73 | 54 | |
| Mean (SD) | 3.2 (27.5) | 168.2 (313.4) | |
| Median | 0.0 | 50.2 | |
| Q1, Q3 | 0.0, 0.0 | 2.0, 160.5 | |
| Range | (0.0-235.4) | (0.0-1506.0) | |
| ITGA2_AVG_NORM | | | 0.0007 |
| N | 73 | 54 | |
| Mean (SD) | 0.0 (0.0) | 2.6 (10.0) | |
| Median | 0.0 | 0.0 | |
| Q1, Q3 | 0.0, 0.0 | 0.0, 0.0 | |
| Range | (0.0-0.0) | (0.0-69.7) | |
| ITGAV_AVG_NORM | | | <0.0001 |
| N | 73 | 54 | |
| Mean (SD) | 3.3 (23.9) | 22.0 (32.9) | |
| Median | 0.0 | 8.0 | |
| Q1, Q3 | 0.0, 0.0 | 0.0, 31.0 | |
| Range | (0.0-199.9) | (0.0-176.8) | |
| ITGB3_AVG_NORM | | | <0.0001 |
| N | 73 | 54 | |
| Mean (SD) | 0.0 (0.0) | 43.6 (90.3) | |
| Median | 0.0 | 0.0 | |
| Q1, Q3 | 0.0, 0.0 | 0.0, 52.5 | |
| Range | (0.0-0.0) | (0.0-495.3) | |
| ITGB1_AVG_NORM | | | <0.0001 |
| N | 73 | 54 | |
| Mean (SD) | 29.9 (95.1) | 616.2 (742.2) | |
| Median | 0.0 | 400.2 | |
| Q1, Q3 | 0.0, 0.0 | 84.7, 869.0 | |
| Range | (0.0-487.9) | (0.0-3877.9) | |
| FN1_AVG_NORM | | | <0.0001 |
| N | 73 | 54 | |
| Mean (SD) | 2.9 (15.6) | 1570.9 (1949.8) | |
| Median | 0.0 | 898.4 | |
| Q1, Q3 | 0.0, 0.0 | 299.5, 2186.1 | |
| Range | (0.0-123.2) | (0.0-11073.5) | |
| THBS1_AVG_NORM | | | <0.0001 |

TABLE C-continued

Comparison of gene expression between benign and malignant

| | Benign (N = 73) | Malignant (N = 54) | p value |
|---|---|---|---|
| N | 73 | 54 | |
| Mean (SD) | 0.0 (0.0) | 85.1 (136.1) | |
| Median | 0.0 | 16.8 | |
| Q1, Q3 | 0.0, 0.0 | 0.0, 153.8 | |
| Range | (0.0-0.0) | (0.0-786.2) | |
| THBS2_AVG_NORM | | | <0.0001 |
| N | 73 | 54 | |
| Mean (SD) | 25.9 (113.4) | 280.0 (513.5) | |
| Median | 0.0 | 44.1 | |
| Q1, Q3 | 0.0, 0.0 | 0.0, 340.1 | |
| Range | (0.0-729.2) | (0.0-3030.5) | |
| THBS4_AVG_NORM | | | <0.0001 |
| N | 73 | 54 | |
| Mean (SD) | 38.5 (151.2) | 228.2 (663.7) | |
| Median | 0.0 | 22.5 | |
| Q1, Q3 | 0.0, 0.0 | 0.0, 97.9 | |
| Range | (0.0-1130.3) | (0.0-3977.7) | |
| VCAN_AVG_NORM | | | <0.0001 |
| N | 73 | 54 | |
| Mean (SD) | 3.0 (21.7) | 202.4 (262.8) | |
| Median | 0.0 | 103.4 | |
| Q1, Q3 | 0.0, 0.0 | 0.0, 283.5 | |
| Range | (0.0-181.3) | (0.0-1113.2) | |
| BGAN_AVG_NORM | | | <0.0001 |
| N | 73 | 54 | |
| Mean (SD) | 69.3 (121.0) | 422.4 (573.1) | |
| Median | 0.0 | 248.5 | |
| Q1, Q3 | 0.0, 97.9 | 113.5, 462.9 | |
| Range | (0.0-496.3) | (0.0-3348.1) | |
| SPP1_AVG_NORM | | | <0.0001 |
| N | 73 | 54 | |
| Mean (SD) | 0.0 (0.0) | 1490.2 (3397.4) | |
| Median | 0.0 | 338.1 | |
| Q1, Q3 | 0.0, 0.0 | 4.9, 1577.7 | |
| Range | (0.0-0.0) | (0.0-22427.0) | |
| TNC_AVG_NORM | | | <0.0001 |
| N | 73 | 54 | |
| Mean (SD) | 66.4 (240.1) | 800.1 (808.7) | |
| Median | 0.0 | 495.8 | |
| Q1, Q3 | 0.0, 0.0 | 174.5, 1322.9 | |
| Range | (0.0-1393.3) | (0.0-3162.2) | |
| SPARC_AVG_NORM | | | <0.0001 |
| N | 73 | 54 | |
| Mean (SD) | 843.7 (2222.8) | 3208.4 (3182.6) | |
| Median | 0.0 | 2895.8 | |
| Q1, Q3 | 0.0, 0.0 | 407.2, 5216.3 | |
| Range | (0.0-11175.6) | (0.0-13631.9) | |
| AGRN_AVG_NORM | | | <0.0001 |
| N | 73 | 54 | |
| Mean (SD) | 4.7 (18.1) | 51.2 (53.8) | |
| Median | 0.0 | 42.1 | |
| Q1, Q3 | 0.0, 0.0 | 10.7, 69.7 | |
| Range | (0.0-121.7) | (0.0-242.0) | |
| CTGF_AVG_NORM | | | <0.0001 |
| N | 73 | 54 | |
| Mean (SD) | 0.4 (3.6) | 90.9 (231.6) | |
| Median | 0.0 | 22.1 | |
| Q1, Q3 | 0.0, 0.0 | 0.0, 125.9 | |
| Range | (0.0-30.6) | (0.0-1631.4) | |
| CYR61_AVG_NORM | | | <0.0001 |
| N | 73 | 54 | |
| Mean (SD) | 4.8 (13.0) | 27.2 (39.2) | |
| Median | 0.0 | 18.7 | |
| Q1, Q3 | 0.0, 0.0 | 4.9, 32.2 | |
| Range | (0.0-70.4) | (0.0-267.2) | |
| LAMA3_AVG_NORM | | | 0.0004 |
| N | 73 | 54 | |
| Mean (SD) | 1.1 (9.0) | 1.2 (2.9) | |
| Median | 0.0 | 0.0 | |
| Q1, Q3 | 0.0, 0.0 | 0.0, 0.0 | |
| Range | (0.0-76.8) | (0.0-11.3) | |
| LAMC1_AVG_NORM | | | <0.0001 |
| N | 73 | 54 | |
| Mean (SD) | 0.0 (0.0) | 70.6 (159.4) | |
| Median | 0.0 | 28.4 | |
| Q1, Q3 | 0.0, 0.0 | 0.0, 99.3 | |
| Range | (0.0-0.0) | (0.0-1136.2) | |
| LAMB1_AVG_NORM | | | <0.0001 |
| N | 73 | 54 | |
| Mean (SD) | 9.2 (38.4) | 221.1 (354.3) | |
| Median | 0.0 | 73.1 | |
| Q1, Q3 | 0.0, 0.0 | 0.0, 339.8 | |
| Range | (0.0-248.8) | (0.0-1877.6) | |
| LAMA1_AVG_NORM | | | <0.0001 |
| N | 73 | 54 | |
| Mean (SD) | 5.7 (14.5) | 65.4 (149.0) | |
| Median | 0.0 | 10.6 | |
| Q1, Q3 | 0.0, 0.0 | 0.0, 49.0 | |
| Range | (0.0-76.5) | (0.0-754.3) | |
| LAMC2_AVG_NORM | | | 0.0003 |
| N | 73 | 54 | |
| Mean (SD) | 0.0 (0.0) | 4.0 (15.3) | |
| Median | 0.0 | 0.0 | |
| Q1, Q3 | 0.0, 0.0 | 0.0, 0.0 | |
| Range | (0.0-0.0) | (0.0-91.1) | |
| LAMB3_AVG_NORM | | | 0.1473 |
| N | 73 | 54 | |
| Mean (SD) | 33.5 (60.3) | 32.2 (54.5) | |
| Median | 0.0 | 12.1 | |
| Q1, Q3 | 0.0, 44.6 | 0.0, 37.0 | |
| Range | (0.0-323.9) | (0.0-246.0) | |
| COL1A1_AVG_NORM | | | <0.0001 |
| N | 73 | 54 | |
| Mean (SD) | 1534.4 (4365.3) | 4191.6 (5865.9) | |
| Median | 0.0 | 1704.4 | |
| Q1, Q3 | 0.0, 0.0 | 0.0, 6850.9 | |
| Range | (0.0-22510.2) | (0.0-31867.0) | |
| COL4A1_AVG_NORM | | | <0.0001 |
| N | 73 | 54 | |
| Mean (SD) | 0.0 (0.0) | 211.8 (344.1) | |
| Median | 0.0 | 118.4 | |
| Q1, Q3 | 0.0, 0.0 | 2.3, 261.2 | |
| Range | (0.0-0.0) | (0.0-1774.4) | |
| COL18A1_AVG_NORM | | | <0.0001 |
| N | 73 | 54 | |
| Mean (SD) | 94.2 (783.4) | 22.8 (38.8) | |
| Median | 0.0 | 4.1 | |
| Q1, Q3 | 0.0, 0.0 | 0.0, 34.4 | |
| Range | (0.0-6695.7) | (0.0-208.8) | |
| LOX_AVG_NORM | | | 0.0003 |
| N | 73 | 54 | |
| Mean (SD) | 37.7 (132.8) | 65.0 (113.9) | |
| Median | 0.0 | 3.5 | |
| Q1, Q3 | 0.0, 0.0 | 0.0, 58.0 | |
| Range | (0.0-991.2) | (0.0-443.3) | |
| LOXL1_AVG_NORM | | | <0.0001 |
| N | 73 | 54 | |
| Mean (SD) | 0.8 (7.1) | 39.6 (60.3) | |
| Median | 0.0 | 18.5 | |
| Q1, Q3 | 0.0, 0.0 | 0.0, 65.0 | |
| Range | (0.0-60.4) | (0.0-349.0) | |
| LOXL2_AVG_NORM | | | <0.0001 |
| N | 73 | 54 | |
| Mean (SD) | 43.3 (356.8) | 68.5 (129.9) | |
| Median | 0.0 | 22.1 | |
| Q1, Q3 | 0.0, 0.0 | 0.0, 89.1 | |
| Range | (0.0-3048.4) | (0.0-821.4) | |
| LOXL3_AVG_NORM | | | <0.0001 |
| N | 73 | 54 | |
| Mean (SD) | 2.2 (12.3) | 28.4 (71.1) | |
| Median | 0.0 | 9.2 | |
| Q1, Q3 | 0.0, 0.0 | 2.5, 29.4 | |
| Range | (0.0-89.7) | (0.0-507.5) | |
| LOXL4_AVG_NORM | | | 0.0010 |

TABLE C-continued

Comparison of gene expression between benign and malignant

| | Benign (N = 73) | Malignant (N = 54) | p value |
|---|---|---|---|
| N | 73 | 54 | |
| Mean (SD) | 33.8 (91.0) | 129.1 (300.4) | |
| Median | 0.0 | 9.1 | |
| Q1, Q3 | 0.0, 10.2 | 0.0, 67.0 | |
| Range | (0.0-529.2) | (0.0-1230.0) | |
| PLOD1_AVG_NORM | | | <0.0001 |
| N | 73 | 54 | |
| Mean (SD) | 33.7 (116.5) | 420.3 (532.2) | |
| Median | 0.0 | 242.3 | |
| Q1, Q3 | 0.0, 0.0 | 90.2, 659.3 | |
| Range | (0.0-878.2) | (0.0-3336.8) | |
| PLOD2_AVG_NORM | | | <0.0001 |
| N | 73 | 54 | |
| Mean (SD) | 44.5 (151.7) | 314.8 (1284.4) | |
| Median | 0.0 | 53.7 | |
| Q1, Q3 | 0.0, 0.0 | 2.3, 103.3 | |
| Range | (0.0-1124.0) | (0.0-9110.5) | |
| PLOD3_AVG_NORM | | | <0.0001 |
| N | 73 | 54 | |
| Mean (SD) | 2.7 (11.9) | 68.0 (81.2) | |
| Median | 0.0 | 38.3 | |
| Q1, Q3 | 0.0, 0.0 | 4.2, 101.9 | |
| Range | (0.0-87.4) | (0.0-330.2) | |
| PCOLCE2_AVG_NORM | | | 0.0010 |
| N | 73 | 54 | |
| Mean (SD) | 7.7 (25.8) | 6.4 (14.9) | |
| Median | 0.0 | 0.0 | |
| Q1, Q3 | 0.0, 0.0 | 0.0, 3.1 | |
| Range | (0.0-104.8) | (0.0-68.4) | |
| PCOLCE_AVG_NORM | | | 0.0232 |
| N | 73 | 54 | |
| Mean (SD) | 92.1 (159.7) | 170.4 (339.4) | |
| Median | 0.0 | 40.9 | |
| Q1, Q3 | 0.0, 122.2 | 0.0, 175.1 | |
| Range | (0.0-699.2) | (0.0-1945.2) | |
| PTK2_AVG_NORM | | | <0.0001 |
| N | 73 | 54 | |
| Mean (SD) | 2.8 (14.4) | 76.6 (81.8) | |
| Median | 0.0 | 70.0 | |
| Q1, Q3 | 0.0, 0.0 | 0.0, 127.7 | |
| Range | (0.0-116.5) | (0.0-323.3) | |
| CSRC_AVG_NORM | | | 0.0001 |
| N | 73 | 54 | |
| Mean (SD) | 19.0 (40.9) | 45.1 (65.9) | |
| Median | 0.3 | 19.6 | |
| Q1, Q3 | 0.0, 24.8 | 4.2, 46.6 | |
| Range | (0.0-266.6) | (0.0-290.2) | |
| CDKN1A_AVG_NORM | | | 0.0005 |
| N | 73 | 54 | |
| Mean (SD) | 78.5 (150.9) | 181.0 (271.7) | |
| Median | 0.0 | 84.2 | |
| Q1, Q3 | 0.0, 118.9 | 0.0, 253.3 | |
| Range | (0.0-788.2) | (0.0-1083.2) | |
| CDKN2A_AVG_NORM | | | 0.0002 |
| N | 73 | 54 | |
| Mean (SD) | 6.1 (19.6) | 9.7 (25.8) | |
| Median | 0.0 | 1.0 | |
| Q1, Q3 | 0.0, 0.0 | 0.0, 6.9 | |
| Range | (0.0-113.2) | (0.0-175.1) | |
| TP53_AVG_NORM | | | <0.0001 |
| N | 73 | 54 | |
| Mean (SD) | 40.6 (98.6) | 231.2 (289.8) | |
| Median | 0.0 | 166.9 | |
| Q1, Q3 | 0.0, 0.0 | 0.0, 359.9 | |
| Range | (0.0-410.8) | (0.0-1722.4) | |
| YAP_AVG_NORM | | | <0.0001 |
| N | 73 | 54 | |
| Mean (SD) | 7.8 (36.6) | 112.4 (161.4) | |
| Median | 0.0 | 63.1 | |
| Q1, Q3 | 0.0, 0.0 | 0.0, 173.5 | |
| Range | (0.0-246.3) | (0.0-769.0) | |
| TAZ_AVG_NORM | | | <0.0001 |
| N | 73 | 54 | |
| Mean (SD) | 12.2 (27.9) | 32.8 (44.3) | |
| Median | 0.0 | 15.0 | |
| Q1, Q3 | 0.0, 0.7 | 0.0, 49.0 | |
| Range | (0.0-122.7) | (0.0-186.4) | |
| MITF_AVG_NORM | | | <0.0001 |
| N | 73 | 54 | |
| Mean (SD) | 251.0 (399.5) | 569.8 (494.8) | |
| Median | 45.5 | 467.3 | |
| Q1, Q3 | 0.0, 331.5 | 184.9, 777.8 | |
| Range | (0.0-2143.3) | (0.0-2200.0) | |
| MLANA_AVG_NORM | | | 0.1823 |
| N | 73 | 54 | |
| Mean (SD) | 3596.0 (3671.3) | 4865.4 (4966.1) | |
| Median | 2446.8 | 2803.5 | |
| Q1, Q3 | 950.9, 5019.4 | 1210.7, 6773.0 | |
| Range | (14.0-17180.3) | (62.8-19672.1) | |
| TYR_AVG_NORM | | | 0.0040 |
| N | 73 | 54 | |
| Mean (SD) | 349.7 (301.8) | 839.8 (996.3) | |
| Median | 254.3 | 515.1 | |
| Q1, Q3 | 119.5, 527.5 | 161.0, 1244.9 | |
| Range | (0.0-1169.8) | (2.0-5500.0) | |
| POSTN_AVG_NORM | | | 0.0001 |
| N | 73 | 54 | |
| Mean (SD) | 1138.7 (2155.7) | 1933.9 (2318.1) | |
| Median | 191.6 | 1252.0 | |
| Q1, Q3 | 0.0, 1449.9 | 397.4, 2457.4 | |
| Range | (0.0-11078.1) | (0.0-11193.2) | |
| FBLN2_AVG_NORM | | | <0.0001 |
| N | 73 | 54 | |
| Mean (SD) | 2.1 (17.3) | 26.5 (42.2) | |
| Median | 0.0 | 0.0 | |
| Q1, Q3 | 0.0, 0.0 | 0.0, 48.8 | |
| Range | (0.0-148.2) | (0.0-150.9) | |

TABLE D

Comparison of gene expression between benign and malignant

| | Benign (N = 73) | Malignant (N = 54) | p value |
|---|---|---|---|
| CXCL1_AVG_NORM01 | | | <0.0001 |
| Zero | 58 (79.5%) | 12 (22.2%) | |
| >0 | 15 (20.5%) | 42 (77.8%) | |
| CSF2_AVG_NORM01 | | | 0.0398 |
| Zero | 15 (20.5%) | 20 (37.0%) | |
| >0 | 58 (79.5%) | 34 (63.0%) | |
| CCL2_AVG_NORM01 | | | <0.0001 |
| Zero | 53 (72.6%) | 12 (22.2%) | |
| >0 | 20 (27.4%) | 42 (77.8%) | |
| IL8_AVG_NORM01 | | | <0.0001 |
| Zero | 63 (86.3%) | 10 (18.5%) | |
| >0 | 10 (13.7%) | 44 (81.5%) | |
| IL6_AVG_NORM01 | | | <0.0001 |
| Zero | 65 (89.0%) | 13 (24.1%) | |
| >0 | 8 (11.0%) | 41 (75.9%) | |
| ITGA5_AVG_NORM01 | | | <0.0001 |
| Zero | 73 (100.0%) | 38 (70.4%) | |
| >0 | 0 (0.0%) | 16 (29.6%) | |
| ITGA3_AVG_NORM01 | | | <0.0001 |
| Zero | 72 (98.6%) | 13 (24.1%) | |
| >0 | 1 (1.4%) | 41 (75.9%) | |
| ITGA2_AVG_NORM01 | | | 0.0007 |
| Zero | 73 (100.0%) | 46 (85.2%) | |
| >0 | 0 (0.0%) | 8 (14.8%) | |
| ITGAV_AVG_NORM01 | | | <0.0001 |
| Zero | 71 (97.3%) | 24 (44.4%) | |
| >0 | 2 (2.7%) | 30 (55.6%) | |

TABLE D-continued

Comparison of gene expression between benign and malignant

| | Benign (N = 73) | Malignant (N = 54) | p value |
|---|---|---|---|
| ITGB3_AVG_NORM01 | | | <0.0001 |
| Zero | 73 (100.0%) | 30 (55.6%) | |
| >0 | 0 (0.0%) | 24 (44.4%) | |
| ITGB1_AVG_NORM01 | | | <0.0001 |
| Zero | 64 (87.7%) | 11 (20.4%) | |
| >0 | 9 (12.3%) | 43 (79.6%) | |
| FN1_AVG_NORM01 | | | <0.0001 |
| Zero | 69 (94.5%) | 2 (3.7%) | |
| >0 | 4 (5.5%) | 52 (96.3%) | |
| THBS1_AVG_NORM01 | | | <0.0001 |
| Zero | 73 (100.0%) | 24 (44.4%) | |
| >0 | 0 (0.0%) | 30 (55.6%) | |
| THBS2_AVG_NORM01 | | | <0.0001 |
| Zero | 67 (91.8%) | 23 (42.6%) | |
| >0 | 6 (8.2%) | 31 (57.4%) | |
| THBS4_AVG_NORM01 | | | <0.0001 |
| Zero | 58 (79.5%) | 15 (27.8%) | |
| >0 | 15 (20.5%) | 39 (72.2%) | |
| VCAN_AVG_NORM01 | | | <0.0001 |
| Zero | 71 (97.3%) | 16 (29.6%) | |
| >0 | 2 (2.7%) | 38 (70.4%) | |
| BGAN_AVG_NORM01 | | | <0.0001 |
| Zero | 42 (57.5%) | 7 (13.0%) | |
| >0 | 31 (42.5%) | 47 (87.0%) | |
| SPP1_AVG_NORM01 | | | <0.0001 |
| Zero | 73 (100.0%) | 12 (22.2%) | |
| >0 | 0 (0.0%) | 42 (77.8%) | |
| TNC_AVG_NORM01 | | | <0.0001 |
| Zero | 60 (82.2%) | 3 (5.6%) | |
| >0 | 13 (17.8%) | 51 (94.4%) | |
| SPARC_AVG_NORM01 | | | <0.0001 |
| Zero | 57 (78.1%) | 13 (24.1%) | |
| >0 | 16 (21.9%) | 41 (75.9%) | |
| AGRN_AVG_NORM01 | | | <0.0001 |
| Zero | 59 (80.8%) | 5 (9.3%) | |
| >0 | 14 (19.2%) | 49 (90.7%) | |
| CTGF_AVG_NORM01 | | | <0.0001 |
| Zero | 72 (98.6%) | 21 (38.9%) | |
| >0 | 1 (1.4%) | 33 (61.1%) | |
| CYR61_AVG_NORM01 | | | <0.0001 |
| Zero | 56 (76.7%) | 9 (16.7%) | |
| >0 | 17 (23.3%) | 45 (83.3%) | |
| LAMA3_AVG_NORM01 | | | 0.0003 |
| Zero | 72 (98.6%) | 43 (79.6%) | |
| >0 | 1 (1.4%) | 11 (20.4%) | |
| LAMC1_AVG_NORM01 | | | <0.0001 |
| Zero | 73 (100.0%) | 24 (44.4%) | |
| >0 | 0 (0.0%) | 30 (55.6%) | |
| LAMB1_AVG_NORM01 | | | <0.0001 |
| Zero | 66 (90.4%) | 22 (40.7%) | |
| >0 | 7 (9.6%) | 32 (59.3%) | |
| LAMA1_AVG_NORM01 | | | <0.0001 |
| Zero | 57 (78.1%) | 16 (29.6%) | |
| >0 | 16 (21.9%) | 38 (70.4%) | |
| LAMC2_AVG_NORM01 | | | 0.0003 |
| Zero | 73 (100.0%) | 45 (83.3%) | |
| >0 | 0 (0.0%) | 9 (16.7%) | |
| LAMB3_AVG_NORM01 | | | 0.0061 |
| Zero | 45 (61.6%) | 20 (37.0%) | |
| >0 | 28 (38.4%) | 34 (63.0%) | |
| COL1A1_AVG_NORM01 | | | <0.0001 |
| Zero | 60 (82.2%) | 17 (31.5%) | |
| >0 | 13 (17.8%) | 37 (68.5%) | |
| COL4A1_AVG_NORM01 | | | <0.0001 |
| Zero | 73 (100.0%) | 13 (24.1%) | |
| >0 | 0 (0.0%) | 41 (75.9%) | |
| COL18A1_AVG_NORM01 | | | <0.0001 |
| Zero | 64 (87.7%) | 18 (33.3%) | |
| >0 | 9 (12.3%) | 36 (66.7%) | |
| LOX_AVG_NORM01 | | | <0.0001 |
| Zero | 60 (82.2%) | 26 (48.1%) | |
| >0 | 13 (17.8%) | 28 (51.9%) | |
| LOXL1_AVG_NORM01 | | | <0.0001 |
| Zero | 72 (98.6%) | 23 (42.6%) | |
| >0 | 1 (1.4%) | 31 (57.4%) | |
| LOXL2_AVG_NORM01 | | | <0.0001 |
| Zero | 70 (95.9%) | 19 (35.2%) | |
| >0 | 3 (4.1%) | 35 (64.8%) | |
| LOXL3_AVG_NORM01 | | | <0.0001 |
| Zero | 69 (94.5%) | 10 (18.5%) | |
| >0 | 4 (5.5%) | 44 (81.5%) | |
| LOXL4_AVG_NORM01 | | | 0.0006 |
| Zero | 53 (72.6%) | 23 (42.6%) | |
| >0 | 20 (27.4%) | 31 (57.4%) | |
| PLOD1_AVG_NORM01 | | | <0.0001 |
| Zero | 59 (80.8%) | 12 (22.2%) | |
| >0 | 14 (19.2%) | 42 (77.8%) | |
| PLOD2_AVG_NORM01 | | | <0.0001 |
| Zero | 59 (80.8%) | 10 (18.5%) | |
| >0 | 14 (19.2%) | 44 (81.5%) | |
| PLOD3_AVG_NORM01 | | | <0.0001 |
| Zero | 66 (90.4%) | 11 (20.4%) | |
| >0 | 7 (9.6%) | 43 (79.6%) | |
| PCOLCE2_AVG_NORM01 | | | 0.0002 |
| Zero | 66 (90.4%) | 34 (63.0%) | |
| >0 | 7 (9.6%) | 20 (37.0%) | |
| PCOLCE_AVG_NORM01 | | | 0.0036 |
| Zero | 42 (57.5%) | 17 (31.5%) | |
| >0 | 31 (42.5%) | 37 (68.5%) | |
| PTK2_AVG_NORM01 | | | <0.0001 |
| Zero | 67 (91.8%) | 16 (29.6%) | |
| >0 | 6 (8.2%) | 38 (70.4%) | |
| CSRC_AVG_NORM01 | | | 0.0001 |
| Zero | 36 (49.3%) | 9 (16.7%) | |
| >0 | 37 (50.7%) | 45 (83.3%) | |
| CDKN1A_AVG_NORM01 | | | 0.0001 |
| Zero | 48 (65.8%) | 16 (29.6%) | |
| >0 | 25 (34.2%) | 38 (70.4%) | |
| CDKN2A_AVG_NORM01 | | | <0.0001 |
| Zero | 57 (78.1%) | 23 (42.6%) | |
| >0 | 16 (21.9%) | 31 (57.4%) | |
| TP53_AVG_NORM01 | | | <0.0001 |
| Zero | 59 (80.8%) | 16 (29.6%) | |
| >0 | 14 (19.2%) | 38 (70.4%) | |
| YAP_AVG_NORM01 | | | <0.0001 |
| Zero | 68 (93.2%) | 22 (40.7%) | |
| >0 | 5 (6.8%) | 32 (59.3%) | |
| TAZ_AVG_NORM01 | | | <0.0001 |
| Zero | 54 (74.0%) | 19 (35.2%) | |
| >0 | 19 (26.0%) | 35 (64.8%) | |
| MITF_AVG_NORM01 | | | <0.0001 |
| Zero | 26 (35.6%) | 2 (3.7%) | |
| >0 | 47 (64.4%) | 52 (96.3%) | |
| MLANA_AVG_NORM01 | | | |
| >0 | 73 (100.0%) | 54 (100.0%) | |
| TYR_AVG_NORM01 | | | 0.2202 |
| Zero | 2 (2.7%) | 0 (0.0%) | |
| >0 | 71 (97.3%) | 54 (100.0%) | |
| POSTN_AVG_NORM01 | | | <0.0001 |
| Zero | 32 (43.8%) | 4 (7.4%) | |
| >0 | 41 (56.2%) | 50 (92.6%) | |
| FBLN2_AVG_NORM01 | | | <0.0001 |
| Zero | 71 (97.3%) | 31 (57.4%) | |
| >0 | 2 (2.7%) | 23 (42.6%) | |

TABLE E

| | MM79_CN AVG per copy K14 | MM80_CN AVG per copy K14 | MM81_CN AVG per copy K14 | MM82_CN AVG per copy K14 | AVG per copy K14 | STDEV | % STDEV |
|---|---|---|---|---|---|---|---|
| KRT14_AVG_NORM | 1 | 1 | 1 | 1 | 1 | 0.000 | |
| KRT10_AVG_NORM | 2.209 | 2.229 | 2.92 | 3.015 | 2.593 | 0.434 | 17% |
| MITF_AVG_NORM | 0.021 | 0.018 | 0.016 | 0.015 | 0.018 | 0.003 | 15% |
| MLANA_AVG_NORM | 0.021 | 0.018 | 0.016 | 0.015 | 0.018 | 0.003 | 15% |
| TYR_AVG_NORM | 0.004 | 0.002 | 0.002 | 0.001 | 0.002 | 0.001 | 56% |
| PMEL_AVG_NORM | 0.025 | 0.027 | 0.03 | 0.018 | 0.025 | 0.005 | 20% |
| FN1_AVG_NORM | 0.077 | 0.065 | 0.035 | 0.042 | 0.055 | 0.020 | 36% |
| SPARC_AVG_NORM | 1.294 | 1.143 | 0.568 | 1.707 | 1.178 | 0.471 | 40% |
| AGRN_AVG_NORM | 0.004 | 0.006 | 0.003 | 0.002 | 0.004 | 0.002 | 46% |
| THBS1_AVG_NORM | 0.064 | 0.015 | 0.018 | 0.005 | 0.026 | 0.026 | 103% |
| THBS2_AVG_NORM | 0.366 | 0.061 | 0.104 | 0.057 | 0.147 | 0.148 | 100% |
| THBS4_AVG_NORM | 0.018 | 0.006 | 0.005 | 0.001 | 0.008 | 0.007 | 98% |
| VCAN_AVG_NORM | 0.095 | 0.034 | 0.04 | 0.027 | 0.049 | 0.031 | 64% |
| BGAN_AVG_NORM | 0.015 | 0.027 | 0.014 | 0.015 | 0.018 | 0.006 | 35% |
| COL1A1_AVG_NORM | 1.695 | 3.44 | 0.689 | 6.695 | 3.130 | 2.635 | 84% |
| COL4A1_AVG_NORM | 0.069 | 0.026 | 0.03 | 0.016 | 0.035 | 0.023 | 66% |
| COL4A2_AVG_NORM | 0.115 | 0.042 | 0.041 | 0.004 | 0.051 | 0.046 | 92% |
| COL18A1_AVG_NORM | 0.015 | 0.009 | 0.005 | 0.002 | 0.008 | 0.006 | 73% |
| CTGF_AVG_NORM | 0.012 | 0.008 | 0.016 | 0.004 | 0.010 | 0.005 | 52% |
| LOX_AVG_NORM | 0.029 | 0.021 | 0.028 | 0.021 | 0.025 | 0.004 | 18% |
| LOXL1_AVG_NORM | 0.015 | 0.009 | 0.016 | 0.015 | 0.014 | 0.003 | 23% |
| LOXL2_AVG_NORM | 0.016 | 0.011 | 0.008 | 0.006 | 0.010 | 0.004 | 42% |
| LOXL3_AVG_NORM | 0.003 | 0.002 | 0.002 | 0.001 | 0.002 | 0.001 | 41% |
| LOXL4_AVG_NORM | 0.02 | 0.004 | 0.003 | 0.001 | 0.007 | 0.009 | 125% |
| PLOD2_AVG_NORM | 0.018 | 0.014 | 0.007 | 0.001 | 0.010 | 0.008 | 75% |
| PLOD1_AVG_NORM | 0.069 | 0.053 | 0.026 | 0.017 | 0.041 | 0.024 | 58% |
| SPP1_AVG_NORM | 0.092 | 0.002 | 0.007 | 0 | 0.025 | 0.045 | 177% |
| TNC_AVG_NORM | 0.025 | 0.02 | 0.027 | 0.013 | 0.021 | 0.006 | 29% |
| PCOLCE2_AVG_NORM | 0.011 | 0.001 | 0.006 | 0 | 0.005 | 0.005 | 113% |
| PCOLCE_AVG_NORM | 0.028 | 0.049 | 0.032 | 0.04 | 0.037 | 0.009 | 25% |
| PLOD3_AVG_NORM | 0.03 | 0.006 | 0.007 | 0.002 | 0.011 | 0.013 | 113% |
| ITGB3_AVG_NORM | 0.03 | 0.006 | 0.007 | 0.002 | 0.011 | 0.013 | 113% |
| ITGB1_AVG_NORM | 0.164 | 0.054 | 0.074 | 0.038 | 0.083 | 0.056 | 68% |
| FBLN2_AVG_NORM | 0.049 | 0.022 | 0.02 | 0.016 | 0.027 | 0.015 | 56% |
| CYR61_AVG_NORM | 0.006 | 0.002 | 0.003 | 0 | 0.003 | 0.003 | 91% |
| ITGA5_AVG_NORM | 0.011 | 0.005 | 0.007 | 0.003 | 0.007 | 0.003 | 53% |
| ITGA3_AVG_NORM | 0.016 | 0.008 | 0.006 | 0.008 | 0.010 | 0.004 | 47% |
| ITGA2_AVG_NORM | 0.08 | 0.034 | 0.019 | 0.084 | 0.054 | 0.033 | 60% |
| ITGAV_AVG_NORM | 0.013 | 0.005 | 0.003 | 0.003 | 0.006 | 0.005 | 79% |
| CSRC_AVG_NORM | 0.006 | 0.003 | 0.005 | 0.001 | 0.004 | 0.002 | 59% |
| PTK2_AVG_NORM | 0.035 | 0.02 | 0.011 | 0.009 | 0.019 | 0.012 | 63% |
| POSTN_AVG_NORM | 0.077 | 0.092 | 0.117 | 0.193 | 0.120 | 0.052 | 43% |
| YAP_AVG_NORM | 0.079 | 0.029 | 0.033 | 0.031 | 0.043 | 0.024 | 56% |
| CXCL1_AVG_NORM | 0.002 | 0 | 0 | 0 | 0.001 | 0.001 | 200% |
| CSF2_AVG_NORM | 0.002 | 0 | 0 | 0 | 0.001 | 0.001 | 200% |
| CCL2_AVG_NORM | 0.039 | 0.018 | 0.013 | 0.008 | 0.020 | 0.014 | 70% |
| IL8_AVG_NORM | 0.003 | 0 | 0.001 | 0 | 0.001 | 0.001 | 141% |
| IL6_AVG_NORM | 0.001 | 0 | 0 | 0 | 0.000 | 0.001 | 200% |
| LAMA3_AVG_NORM | 0.038 | 0.012 | 0.021 | 0.011 | 0.021 | 0.013 | 61% |
| TP53_AVG_NORM | 0.08 | 0.04 | 0.039 | 0.052 | 0.053 | 0.019 | 36% |
| CDKN1A_AVG_NORM | 0.057 | 0.029 | 0.037 | 0.014 | 0.034 | 0.018 | 52% |
| CDKN2A_AVG_NORM | 0.003 | 0.001 | 0.001 | 0 | 0.001 | 0.001 | 101% |
| TAZ_AVG_NORM | 0.026 | 0.008 | 0.008 | 0.003 | 0.011 | 0.010 | 90% |
| LAMC1_AVG_NORM | 0.062 | 0.013 | 0.016 | 0.008 | 0.025 | 0.025 | 101% |
| LAMB1_AVG_NORM | 0.046 | 0.019 | 0.026 | 0.008 | 0.025 | 0.016 | 65% |
| LAMA1_AVG_NORM | 0.007 | 0 | 0.001 | 0 | 0.002 | 0.003 | 168% |
| LAMC2_AVG_NORM | 0.034 | 0.009 | 0.012 | 0.016 | 0.018 | 0.011 | 63% |
| LAMB3_AVG_NORM | 0.042 | 0.016 | 0.026 | 0.017 | 0.025 | 0.012 | 48% |
| PLAT_AVG_NORM | 0.032 | 0.02 | 0.034 | 0.04 | 0.032 | 0.001 | 27% |
| CSK_AVG_NORM | 0.027 | 0.034 | 0.021 | 0.041 | 0.031 | 0.001 | 28% |
| GDF15_AVG_NORM | 0.029 | 0.019 | 0.033 | 0.019 | 0.025 | 0.001 | 28% |
| FARP1_AVG_NORM | 0.019 | 0.029 | 0.022 | 0.031 | 0.025 | 0.001 | 22% |
| ARPC1B_AVG_NORM | 0.015 | 0.03 | 0.042 | 0.018 | 0.026 | 0.012 | 47% |
| NES_AVG_NORM | 0.114 | 0.125 | 0.112 | 0.084 | 0.109 | 0.017 | 16% |
| NTRK3_AVG_NORM | 0.021 | 0.025 | 0.022 | 0.033 | 0.025 | 0.001 | 25% |
| SNX17_AVG_NORM | 0.112 | 0.099 | 0.089 | 0.123 | 0.106 | 0.015 | 14% |
| L1CAM_AVG_NORM | 0.017 | 0.04 | 0.01 | 0.024 | 0.023 | 0.013 | 56% |
| CD44_AVG_NORM | 0.112 | 0.089 | 0.09 | 0.123 | 0.104 | 0.017 | 16% |

The results provided herein demonstrate the development of a method for determining absolute levels (copy numbers) of genes of interest (e.g., FN-associated genes) from paraffin-embedded tissue by generating a highly defined internal standard that can be regenerated indefinitely. This standardization approach can allow for the comparison of results from independent experiments and thus, allows for extensive validation. The RT-PCR not only produced strong signals from highly degraded RNA due to FFPE embedding, but also was amendable to high-throughput analysis and was highly cost effective. While the methods provided herein were validated for melanoma, these methods are likely applicable to other human cancers. The results provided herein also demonstrate the discrimination between benign and malignant pigmented lesions based on multiple markers.

Example 3—Additional Marker Panel

A test kit panel was designed to include primers for assessing expression levels of eight marker genes (ITGB3, TNC, SPP1, SPARC, PLAT, COL4A1, PLOD3, and PTK2) as well as three housekeeping genes (ACTB, RPLP0, and RPL8), one keratinocyte markers (K14) to assess keratinocyte contamination, and two melanocyte markers (MLANA and MITF) to assess melanocyte content in the skin sections. The primers designed for this collection are set forth in Table 11.

TABLE 11

Primers for marker panel kit.

| Gene | Primer pair name | Direction | Sequence | SEQ ID NO: |
|---|---|---|---|---|
| ACTB | ACTB-G | -F | TGCTATCCCTGTACGCCTCT | 433 |
|  | ACTB-G | -R | GAGTCCATCACGATGCCAGT | 434 |
| ACTB | ACTB-H | -F | GGACTTCGAGCAAGAGATGG | 435 |
|  | ACTB-H | -R | CTTCTCCAGGGAGGAGCTG | 436 |
| ACTB | ACTB-I | -F | GGCTACAGCTTCACCACCAC | 425 |
|  | ACTB-I | -R | TAATGTCACGCACGATTTCC | 426 |
| RPLP0 | RPLP0-B | -F | AACTCTGCATTCTCGCTTCC | 9 |
|  | RPLP0-B | -R | GCAGACAGACACTGGCAACA | 10 |
| RPLP0 | RPLP0-C | -F | GCACCATTGAAATCCTGAGTG | 11 |
|  | RPLP0-C | -R | GCTCCCACTTTGTCTCCAGT | 12 |
| RPL8 | RPL8-B | -F | ACAGAGCTGTGGTTGGTGTG | 19 |
|  | RPL8-B | -R | TTGTCAATTCGGCCACCT | 20 |
| RPL8 | RPL8-E | -F | ACTGCTGGCCACGAGTACG | 17 |
|  | RPL8-E | -R | ATGCTCCACAGGATTCATGG | 18 |
| KRT14 | KRT14-D | -F | TCCGCACCAAGTATGAGACA | 39 |
|  | KRT14-D | -R | ACTCATGCGCAGGTTCAACT | 40 |
| KRT14 | KRT14-F | -F | GATGCAGATTGAGAGCCTGA | 437 |
|  | KRT14-F | -R | TTCTTCAGGTAGGCCAGCTC | 438 |
| MLANA | MLANA-C | -F | GAGAAAAACTGTGAACCTGTGG | 53 |
|  | MLANA-C | -R | ATAAGCAGGTGGAGCATTGG | 54 |
| MITF | MITF-B | -F | CGGCATTTGTTGCTCAGAAT | 47 |
|  | MITF-B | -R | GAGCCTGCATTTCAAGTTCC | 48 |
| ITGB3 | ITGB3-A | -F | AAGAGCCAGAGTGTCCCAAG | 159 |
|  | ITGB3-A | -R | ACTGAGAGCAGGACCACCA | 160 |
| ITGB3 | ITGB3-B | -F | CTTCTCCTGTGTCCGCTACAA | 161 |
|  | ITGB3-B | -R | CATGGCCTGAGCACATCTC | 162 |

TABLE 11-continued

Primers for marker panel kit.

| Gene | Primer pair name | Direction | Sequence | SEQ ID NO: |
|---|---|---|---|---|
| PLAT | PLAT-C | -F | CCCAGCCAGGAAATCCAT | 427 |
|  | PLAT-C | -R | CTGGCTCCTCTTCTGAATCG | 428 |
| PLAT | PLAT-D | -F | CAGTGCCTGTCAAAAGTTGC | 429 |
|  | PLAT-D | -R | CCCCGTTGAAACACCTTG | 430 |
| PLAT | PLAT-E | -F | GAAGGATTTGCTGGGAAGTG | 441 |
|  | PLAT-E | -R | CGTGGCCCTGGTATCTATTT | 442 |
| PLOD3 | PLOD3-D | -F | GGAAGGAATCGTGGAGCAG | 111 |
|  | PLOD3-D | -R | CAGCAGTGGGAACCAGTACA | 112 |
| PTK2 | PTK2-D | -F | GAGACCATTCCCCTCCTACC | 119 |
|  | PTK2-D | -R | GCTTCTGTGCCATCTCAATCT | 120 |
| CDKN2A | CDKN2A1-C | -F | AGGAGCCAGCGTCTAGGG | 219 |
|  | CDKN2A1-C | -R | CTGCCCATCATCATGACCT | 220 |
| CDKN2A | CDKN2A2-C | -F | AACGCACCGAATAGTTACGG | 221 |
|  | CDKN2A2-C | -R | CATCATCATGACCTGGATCG | 222 |

One purpose of the kit was to differentiate between melanoma with high and low risk of regional metastasis, and to appropriately select patients for surgical procedures such as sentinel lymph node biopsy (SLNB) or total lymphadenectomy. Another purpose of this kit was to estimate disease-free survival, disease relapse, or likelihood of death from melanoma. To study the ability of these methods to discriminate between melanoma with high and low risk of metastasis and to establish superiority to established methods, a cohort of 158 patients between October 1998 and June 2013 were identified as having been diagnosed with high-risk melanoma and as having underwent SLNB with the intention to assess metastatic potential of the tumor. Of note, high-risk melanoma by current criteria are defined as melanoma with an invasion depth (Breslow depth) of ≥1 mm; or melanoma with an invasion depth of 0.75 to 0.99 mm plus the presence of either one of the following three risk factors: >0 mitotic figures/mm$^2$; tumor ulceration present; patient age<40 years.

All 158 patients met the criteria for high risk. 136 patients had a Breslow Depth≥1 mm. 22 patients had a Breslow Depth between 0.75 and 0.99 and had at least one of the aforementioned three risk factors (ulceration, mitotic rate>0, age<40). Of the 158 patients, 36 (22.8%) had a melanoma-positive SLNB.

To select genes for a test kit from a pool of genes, the expression level of 52 genes (variables) was initially determined and dichotomized as zero vs. >zero and evaluated for an association with positive SLNB using the chi-square test for a 2×2 contingency level. The genes are ordered based on the value of the chi-square test statistic (Table 12).

TABLE 12

| Value of the chi-square test statistic | variable |
|---|---|
| ITGB3 | 68.3522 |
| SPP1 | 25.8460 |
| LOXL3 | 16.7683 |
| PLAT | 16.5721 |
| LAMB1 | 15.7544 |
| YAP | 13.4049 |
| PLOD3 | 12.6062 |

TABLE 12-continued

| Value of the chi-square test statistic | variable |
|---|---|
| TP53 | 12.3662 |
| COL4A1 | 11.8336 |
| TNC | 11.3862 |
| IL8 | 10.4697 |
| ITGA5 | 10.3561 |
| COL1A1 | 10.0006 |
| VCAN | 9.3250 |
| PLOD1 | 8.6959 |
| FN1 | 8.4857 |
| PTK2 | 7.9874 |
| ITGAV | 7.7181 |
| LOXL1 | 7.2109 |
| LOXL2 | 6.6348 |
| ITGB1 | 6.3556 |
| CDKN1A | 6.3117 |
| CTGF | 6.2588 |
| GDF15 | 5.96939 |
| CSRC | 5.4435 |
| ITGA2 | 5.0326 |
| ITGA3 | 4.0603 |
| LOX | 3.8697 |
| COL18A1 | 3.3392 |
| IL6 | 3.0435 |
| DSPP | 2.7822 |
| NTRK3 | 2.7822 |
| LOXL4 | 2.7279 |
| THBS2 | 2.5110 |
| SPARC | 1.9884 |
| PCOLCE2 | 1.6499 |
| AGRN | 1.6118 |
| CXCL1 | 1.3483 |
| TAZ | 1.3458 |
| THBS4 | 1.1281 |
| PCOLCE | 0.9198 |
| FBLN2 | 0.9198 |
| LAMC2 | 0.9157 |
| CCL2 | 0.8701 |
| CDKN2A | 0.6047 |
| CSF2 | 0.5408 |
| CYR61 | 0.4713 |
| BGAN | 0.4364 |
| LAMA3 | 0.3455 |
| POSTN | 0.1902 |
| LAMB3 | 0.1058 |
| PLOD2 | 0.0152 |

As can be deduced from the chi-square test statistic, ITGB3 was highly discriminatory between melanoma with and without regional lymph node metastasis. The n (%) with a positive SLNB for those with no expression vs. expression level>0 was summarized (Table 13).

TABLE 13

| | Overall No. (% of 158) | Positive No. (% of each row) |
|---|---|---|
| FN1_01 | | |
| Zero | 110 (69.6%) | 18 (16.4%) |
| >0 | 48 (30.4%) | 18 (37.5%) |
| SPP1_01 | | |
| Zero | 93 (58.9%) | 8 (8.6%) |
| >0 | 65 (41.1%) | 28 (43.1%) |
| ITGB3_01 | | |
| Zero | 107 (67.7%) | 4 (3.7%) |
| >0 | 51 (32.3%) | 32 (62.7%) |
| TNC_01 | | |
| Zero | 114 (72.2%) | 18 (15.8%) |
| >0 | 44 (27.8%) | 18 (40.9%) |
| PLAT_01 | | |
| Missing | 18 | 0 |
| Zero | 83 (59.3%) | 11 (13.3%) |
| >0 | 57 (40.7%) | 25 (43.9%) |
| COL4A1_01 | | |
| Zero | 111 (70.3%) | 17 (15.3%) |
| >0 | 47 (29.7%) | 19 (40.4%) |
| SPARC_01 | | |
| Missing | 4 | 0 |
| Zero | 138 (89.6%) | 30 (21.7%) |
| >0 | 16 (10.4%) | 6 (37.5%) |
| AGRN_01 | | |
| Missing | 4 | 0 |
| Zero | 23 (14.9%) | 3 (13.0%) |
| >0 | 131 (85.1%) | 33 (25.2%) |
| THBS1_01 | | |
| Missing | 135 | 33 |
| Zero | 18 (78.3%) | 0 (0.0%) |
| >0 | 5 (21.7%) | 3 (60.0%) |
| THBS2_01 | | |
| Missing | 4 | 0 |
| Zero | 114 (74.0%) | 23 (20.2%) |
| >0 | 40 (26.0%) | 13 (32.5%) |
| THBS4_01 | | |
| Missing | 4 | 0 |
| Zero | 136 (88.3%) | 30 (22.1%) |
| >0 | 18 (11.7%) | 6 (33.3%) |
| VCAN_01 | | |
| Missing | 4 | 0 |
| Zero | 137 (89.0%) | 27 (19.7%) |
| >0 | 17 (11.0%) | 9 (52.9%) |
| BGAN_01 | | |
| Missing | 4 | 0 |
| Zero | 97 (63.0%) | 21 (21.6%) |
| >0 | 57 (37.0%) | 15 (26.3%) |
| COL1A1_01 | | |
| Missing | 4 | 0 |
| Zero | 145 (94.2%) | 30 (20.7%) |
| >0 | 9 (5.8%) | 6 (66.7%) |
| COL18A1_01 | | |
| Missing | 4 | 0 |
| Zero | 146 (94.8%) | 32 (21.9%) |
| >0 | 8 (5.2%) | 4 (50.0%) |
| CTGF_01 | | |
| Missing | 4 | 0 |
| Zero | 128 (83.1%) | 25 (19.5%) |
| >0 | 26 (16.9%) | 11 (42.3%) |
| LOX_01 | | |
| Missing | 4 | 0 |
| Zero | 149 (96.8%) | 33 (22.1%) |
| >0 | 5 (3.2%) | 3 (60.0%) |
| LOXL1_01 | | |
| Missing | 4 | 0 |
| Zero | 146 (94.8%) | 31 (21.2%) |
| >0 | 8 (5.2%) | 5 (62.5%) |
| LOXL2_01 | | |
| Missing | 4 | 0 |
| Zero | 115 (74.7%) | 21 (18.3%) |
| >0 | 39 (25.3%) | 15 (38.5%) |
| LOXL3_01 | | |
| Missing | 4 | 0 |
| Zero | 67 (43.5%) | 5 (7.5%) |
| >0 | 87 (56.5%) | 31 (35.6%) |
| LOXL4_01 | | |
| Missing | 4 | 0 |
| Zero | 122 (79.2%) | 25 (20.5%) |
| >0 | 32 (20.8%) | 11 (34.4%) |
| PLOD2_01 | | |
| Missing | 4 | 0 |
| Zero | 136 (88.3%) | 32 (23.5%) |
| >0 | 18 (11.7%) | 4 (22.2%) |
| PLOD1_01 | | |
| Missing | 4 | 0 |
| Zero | 111 (72.1%) | 19 (17.1%) |
| >0 | 43 (27.9%) | 17 (39.5%) |
| PCOLCE2_01 | | |
| Missing | 4 | 0 |
| Zero | 144 (93.5%) | 32 (22.2%) |
| >0 | 10 (6.5%) | 4 (40.0%) |
| PCOLCE_01 | | |
| Missing | 4 | 0 |
| Zero | 139 (90.3%) | 31 (22.3%) |

TABLE 13-continued

| | Overall No. (% of 158) | Positive No. (% of each row) |
|---|---|---|
| >0 | 15 (9.7%) | 5 (33.3%) |
| PLOD3_01 | | |
| Missing | 4 | 0 |
| Zero | 109 (70.8%) | 17 (15.6%) |
| >0 | 45 (29.2%) | 19 (42.2%) |
| ITGB1_01 | | |
| Missing | 4 | 0 |
| Zero | 62 (40.3%) | 8 (12.9%) |
| >0 | 92 (59.7%) | 28 (30.4%) |
| FBLN2_01 | | |
| Missing | 4 | 0 |
| Zero | 139 (90.3%) | 31 (22.3%) |
| >0 | 15 (9.7%) | 5 (33.3%) |
| CYR61_01 | | |
| Missing | 4 | 0 |
| Zero | 50 (32.5%) | 10 (20.0%) |
| >0 | 104 (67.5%) | 26 (25.0%) |
| ITGA5_01 | | |
| Missing | 4 | 0 |
| Zero | 135 (87.7%) | 26 (19.3%) |
| >0 | 19 (12.3%) | 10 (52.6%) |
| ITGA3_01 | | |
| Missing | 4 | 0 |
| Zero | 56 (36.4%) | 8 (14.3%) |
| >0 | 98 (63.6%) | 28 (28.6%) |
| ITGA2_01 | | |
| Missing | 4 | 0 |
| Zero | 139 (90.3%) | 29 (20.9%) |
| >0 | 15 (9.7%) | 7 (46.7%) |
| ITGAV_01 | | |
| Missing | 4 | 0 |
| Zero | 120 (77.9%) | 22 (18.3%) |
| >0 | 34 (22.1%) | 14 (41.2%) |
| CSRC_01 | | |
| Missing | 4 | 0 |
| Zero | 90 (58.4%) | 15 (16.7%) |
| >0 | 64 (41.6%) | 21 (32.8%) |
| PTK2_01 | | |
| Missing | 4 | 0 |
| Zero | 61 (39.6%) | 7 (11.5%) |
| >0 | 93 (60.4%) | 29 (31.2%) |
| POSTN_01 | | |
| Missing | 4 | 0 |
| Zero | 103 (66.9%) | 23 (22.3%) |
| >0 | 51 (33.1%) | 13 (25.5%) |
| YAP_01 | | |
| Missing | 4 | 0 |
| Zero | 137 (89.0%) | 26 (19.0%) |
| >0 | 17 (11.0%) | 10 (58.8%) |
| CXCL1_01 | | |
| Missing | 4 | 0 |
| Zero | 94 (61.0%) | 19 (20.2%) |
| >0 | 60 (39.0%) | 17 (28.3%) |
| CSF2_01 | | |
| Missing | 4 | 0 |
| Zero | 131 (85.1%) | 32 (24.4%) |
| >0 | 23 (14.9%) | 4 (17.4%) |
| CCL2_01 | | |
| Missing | 4 | 0 |
| Zero | 112 (72.7%) | 24 (21.4%) |
| >0 | 42 (27.3%) | 12 (28.6%) |
| IL8_01 | | |
| Missing | 4 | 0 |
| Zero | 99 (64.3%) | 15 (15.2%) |
| >0 | 55 (35.7%) | 21 (38.2%) |
| IL6_01 | | |
| Missing | 4 | 0 |
| Zero | 62 (40.3%) | 10 (16.1%) |
| >0 | 92 (59.7%) | 26 (28.3%) |
| LAMA3_01 | | |
| Missing | 4 | 0 |
| Zero | 148 (96.1%) | 34 (23.0%) |
| >0 | 6 (3.9%) | 2 (33.3%) |
| TP53_01 | | |
| Missing | 4 | 0 |
| Zero | 125 (81.2%) | 22 (17.6%) |
| >0 | 29 (18.8%) | 14 (48.3%) |
| CDKN1A_01 | | |
| Missing | 4 | 0 |
| Zero | 118 (76.6%) | 22 (18.6%) |
| >0 | 36 (23.4%) | 14 (38.9%) |
| CDKN2A_01 | | |
| Missing | 4 | 0 |
| Zero | 103 (66.9%) | 26 (25.2%) |
| >0 | 51 (33.1%) | 10 (19.6%) |
| TAZ_01 | | |
| Missing | 4 | 0 |
| Zero | 133 (86.4%) | 29 (21.8%) |
| >0 | 21 (13.6%) | 7 (33.3%) |
| LAMC1_01 | | |
| Missing | 136 | 33 |
| Zero | 19 (86.4%) | 0 (0.0%) |
| >0 | 3 (13.6%) | 3 (100.0%) |
| LAMB1_01 | | |
| Missing | 4 | 0 |
| Zero | 109 (70.8%) | 16 (14.7%) |
| >0 | 45 (29.2%) | 20 (44.4%) |
| LAMA1_01 | | |
| Missing | 4 | 0 |
| Zero | 128 (83.1%) | 30 (23.4%) |
| >0 | 26 (16.9%) | 6 (23.1%) |
| LAMC2_01 | | |
| Missing | 5 | 0 |
| Zero | 145 (94.8%) | 33 (22.8%) |
| >0 | 8 (5.2%) | 3 (37.5%) |
| LAMM_01 | | |
| Missing | 4 | 0 |
| Zero | 139 (90.3%) | 33 (23.7%) |
| >0 | 15 (9.7%) | 3 (20.0%) |
| GDF15_01 | | |
| Missing | 28 | 4 |
| Zero | 65 (50.0%) | 10 (15.4%) |
| >0 | 65 (50.0%) | 22 (33.8%) |
| DSPP_01 | | |
| Missing | 73 | 13 |
| Zero | 16 (18.8%) | 7 (43.8%) |
| >0 | 69 (81.2%) | 16 (23.2%) |
| NTRK3_01 | | |
| Missing | 28 | 4 |
| Zero | 130 (100.0%) | 32 (24.6%) |

To formulate a model that distinguishes melanoma that presents with regional metastasis at the time of diagnosis vs. no metastasis, logic regression was used. Logic regression is a machine learning technique that uses Boolean explanatory variables. There was not a typical technique to create good cut points for logic regression. To assign cut points in the variables, recursive partitioning followed by standardization of cut point levels was used. These were arbitrarily set at 0, 50, 250, and 500. Cut points derived by logic regression were adjusted to the next highest standard level. The cut point for ITGB3 was maintained at 0. The selected model for predicting metastasis was the following:

IF(OR(ITGB3>0,(AND(OR(PTK2>250,PLAT>500, PLOD3>250),CDKN2A<-;50)))=TRUE then predict metastasis Cut point ITGB3=0
Cut point PLAT=500
Cut point PTK2=250
Cut point PLOD3=250
Cut point CDKN2A=50

As can be seen from the formula, the risk of melanoma metastasis was high if ITGB3, PLAT, PTK2 or PLOD3 levels are increased and CDKN2A is low.

This model predicted regional metastasis (defined as a positive SLN biopsy at the time of primary cancer diagnosis) with a specificity of 80.3% and sensitivity of 97.3%.

Example 4—Use of Integrin Adhesions as a Biomarker of Melanoma Sentinel Lymph Node Metastasis Patient Sample
Model Development Cohort All patients with a diagnosis of malignant primary skin melanoma who had a SLN biopsy performed within 90 days of their diagnosis at Mayo Clinic Rochester, Mayo Clinic Arizona, or Mayo Clinic Florida were identified. The diagnosis of melanoma and all related histopathology data were established by ≥2 board-certified Mayo Clinic dermatopathologists. Patients evaluated at Mayo Clinic Rochester were excluded if they had denied access to their medical records for research purposes. The medical records were reviewed, and patients were excluded if they had a "thick" melanoma (Breslow depth>4 mm; T classification T4). The following four variables were used to identify lesions of sufficient risk for inclusion: Breslow depth, presence of ulceration, mitotic rate>0 and age<40 years. A patient was included if i) Breslow depth>1 to <4 mm, or ii) Breslow depth between 0.75 and <1 mm with one or more of the other three risk factors, or iii) Breslow depth between 0.50 and <0.75 mm with two or more of the other three risk factors. Patients with ambiguous pathology or SLN biopsy findings were also excluded. The tissue blocks were reviewed, and patients were excluded if i) the blocks were not retrievable, or ii) sufficient material was not dispensable for research, or iii) only partial primary biopsy samples were available (i.e., biopsies with <80% of total Breslow depth), or iv) available tissue was limited to re-excision specimens in lieu of the original biopsy, or v) the quality of retrievable RNA was poor.

Model Validation Cohort

The model validation cohort consisted of patients who met the same criteria as described for the model development cohort. These patients had a SLN biopsy performed within 90 days of their diagnosis at either Mayo Clinic Rochester or Mayo Clinic Florida.

Data Collection

The following demographic, diagnosis, and pathologic information was abstracted from the medical record: gender, date of birth, date of malignant melanoma diagnosis, date of SLN biopsy, SLN biopsy finding, Breslow depth, mitotic rate (absent, 1-6, >6) presence of ulceration, presence of tumor invading lymphocytes, and presence of angiolymphatic invasion. For analysis purposes, Breslow depth was categorized using recent AJCC guidelines (Balch et al., *J. Clin. Oncol.*, 27:6199 (2009)).

Block Processing

All tissue used was routinely processed, formalin-fixed and paraffin-embedded (FFPE). Preferred starting material for RNA purification was from freshly cut sections of FFPE tissue, each with a thickness of 20 µm. If a tissue was available only as unstained sections mounted on glass slides, RNA retrieval was attempted but typically yielded lower concentrations and poorer quality.

Microfluidic RT-PCR

The Fluidigm BioMark HD System was used for quantitative RT-PCR using EvaGreen DNA binding dye (Biotium) and 96.96 dynamic array integrated fluid circuits (Fluidigm). 77 specific targets in 62 genes (54 experimental and 8 control genes) were amplified per cDNA (standards, controls and experimental samples). Genes included: house-keeping (ACTB, RPLP0, RPL8), melanocyte lineage (MLANA, MITF, TYR, PMEL), basal keratinocyte lineage (KRT14), integrin cell adhesion receptors (ITGB1, ITGB3, ITGA2, ITGA3, ITGA5, ITGAV), integrin trafficking (SNX17, SNX31), fibronectin-related (FN1, THBS1, THBS2, THBS4, SPP1, PLAT, TNC, SPARC, POSTN, FBLN2, DSPP1), collagen-related (COL1A1, COL4A1, COL18A1, PLOD1, PLOD2, PLOD3, LOX, LOXL1, LOXL3, PCOLCE, PCOLCE2), laminins (LAMA1, LAMB1, LAMC1, LAMA3, LAMB3, LAMC2), other extracellular matrix (AGRN, VCAN, GDF15, BGAN, CTGF, CYR61, CSF2, CXCL1, CCL2, IL8, IL6), adhesion signaling (PTK2, CSRC), and cell cycle (CDKN1A, CDKN2A, TP53, YAP, TAZ). The following cDNA were run per array: standards, i.e., linearized cDNA mixes of targets ranging from 5 to 500,000 in copy number and prepared as 1:10 dilutions (a total of six standards), run in triplicates; control cDNA (nevi and melanoma metastases); experimental cDNA; the latter two were in duplicates. All cDNA was pre-amplified in a 14 cycle reaction (TAQMAN® Preamp Master Mix, Applied Biosystems). Array-based quantitative PCR was with the help of the TAQMAN® Gene Expression Master Mix (Applied Biosystems). After thermal cycling, raw Ct data was exported for further analysis. Standards were checked for linear amplification, i.e., a drop in Ct value by approximately $\log_2 10$ per 1:10 dilution. Copy numbers for negative and positive controls were normalized to 25,000 copies of total housekeeping genes. Averaged, normalized gene copy numbers were compared to an internal standard for inter-experiment variation. Data from arrays that did not pass both linear amplification and reproducibility checks were discarded.

To account for sample contamination from keratinocyte-derived RNA, the gene copy number of KRT14, a basal keratinocyte marker, was determined. This number was multiplied with a gene-specific contamination factor, i.e., a value of gene copy number contamination per copy of KRT14. Expression profiling of normal skin devoid of melanocyte nests was performed to establish a contamination factor. The calculated number of keratinocyte-derived RNA contamination was then deducted from the averaged, normalized gene copy number. The final averaged, normalized and background-corrected gene copy number was used for further analysis.

To assess for melanocyte content, at least two melanocyte lineage markers were amplified: MLANA and MITF. Sufficient melanocyte content was assumed if the sum of their averaged, normalized and background-corrected copy numbers was 1,000. If this was not the case, presence of melanocytic tumor had to be confirmed on tissue recuts followed by histologic review. Samples from tissue blocks exhausted of tumor were discarded. Expression data from samples that passed all quality controls were combined with pathology and clinical data and used for statistical modeling.

Chemicals, Antibodies and cDNA

Isopropyl β-D-1-thiogalactopyranoside (IPTG), 4',6-Di-amidino-2-phenylindole dihydrochloridemitomycin (DAPI), blebbistatin and PF-573228 were purchased from Sigma-Aldrich. Dabrafenib (GSK2118436) was purchased from Selleckchem. FAK antibody (06-543) was from EMD MILLIPORE®. FAK pY397 (44624G) antibody was from Life Technologies. Total ERK (9102) and phospho-ERK (4370) antibodies were from Cell Signaling. Paxillin (610051), ITGB3 (555754), ITGB1 (555443) and mouse IgG$_1$ kappa (555749) antibodies were from BD Transduction Labs. Drugs were used at 5 µM final concentration. EGFP control cDNA was from (Lonza). FAK cDNA was obtained from A. Huttenlocher, Addgene plasmid number 35039 (Chan et al., *J. Biol. Chem.*, 285:11418-26 (2010)).

Cell Lines

WM858 were purchased from the Meenhard Herlyn lab (Wistar Institute). WM278 and WM1617 lines were purchased from Coriell Cell Repositories. KN lines were isolated from lymph node metastases using a gentle MACS dissociator and tumor dissociation kit (Miltenyi Biotec). WM and KN lines were propagated exclusively in vitro. M lines were isolated from melanoma brain metastases using previously described methods (Carlson et al., Curr. Prot. Pharmacology, 14.6.1-14.6, 23 (2011)). Some M lines were propagated in mice. Cells were cultured in vitro using DermaLife M Medium (Lifeline Cell Technology).

Generation of IPTG-Inducible FAK shRNA Cells

Five TRC clones were cloned into the pLKO-puro-IPTG-1XLacO vector. The same vector format was used for the non-target negative control (NC) shRNA SHC312V (Sigma-Aldrich). TRC identifiers were as follows: TRCN0000121207, TRCN0000121318, TRCN0000121129, TRCN0000194984, and TRCN0000196310. Lentivirus was produced for each TRC clone and multiple pools of WM858 cells were transduced per clone. The first three TRC sequences did not induce significant FAK knockdown in WM858 cells. The latter two (abbreviated as shRNA 841 and 102) were effective and used for experiments. Selection of successfully transduced cells was with puromycin (Sigma-Aldrich).

Focal Adhesion Visualization on Fibronectin Micropatterns

Cells were plated on micropatterned disks of fluorescent fibronectin surrounded by a cytophobic surface (CYTOO). Cells were allowed to adhere for 1 hour in serum-free medium, and then were fixed and incubated with anti-paxillin antibody followed by a fluorescent secondary antibody and DAPI. Images of fluorescent cells were obtained with a laser scanning confocal microscope (Zeiss LSM780). Max intensity overlays of 15 representative cells per cell type were generated using a plug-in ImageJ macro from CYTOO.

Cell Proliferation

Automated quantification of cell proliferation was by the INCUCYTE™ kinetic imaging system (Essen Bioscience). Approximately 2,000 cells were seeded into a 96-well cell culture dish, eight replicates per condition over the indicated time. Data analysis was with the INCUCYTE ZOOM software package.

Western Blotting by Protein Simple

Western blotting was by standard techniques or automated with a Wes device from ProteinSimple. The automated work-flow was according to the manufacturer's instructions. Image analysis was with the ProteinSimple Compass software.

Gene Expression by Next-Generation Sequencing

Sequencing of FFPE-derived RNA was performed using standard methods. Briefly, RNA-derived cDNA libraries were prepared using the NuGen OVATION® RNAseq FFPE library system. Concentration and size distribution of the resulting libraries were determined on an AGILENT BIOANALYZER® DNA 1000 chip and confirmed by QUBIT® fluorometry (Life Technologies, Grand Island, N.Y.). Unique indexes were incorporated at the adaptor ligation phase for 3-plex sample loading. Libraries were loaded onto paired end flow cells to generate cluster densities of 700,000/mm$^2$ following Illumina's standard protocol. The flow cells were sequenced as 51×2 paired end reads on an ILLUMINA® HISEQ® 2000. For differential gene expression analysis, the edgeR bioconductor software package was used. Because scaling by total lane counts (e.g., by the "reads per kilobase of exon model per million mapped reads" (RPKM) method) can bias estimates of differential expression, quantile-based normalization was used on read counts to determine if genes are differentially expressed (Bullard et al., BMC bioinformatics, 11:94 (2010)) using the negative binomial method (Anders and Huber, Genome Biol., 11:R106 (2010)) requiring an adjusted p-value of <0.01 controlled for multiple testing using the Benjamini and Hochberg correction.

Statistical Methods

Model Development

The primary outcome measure for this study is a positive SLN within 90 days of the primary melanoma diagnosis. Clinical and pathologic characteristics were evaluated univariately for an association with SLN positivity using the chi-square test for categorical variables and the two-sample t-test for continuous variables. A prediction model was constructed from these characteristics using multivariable logistic regression. Associations were summarized using the odds ratio (OR) and corresponding 95% confidence intervals (CI) derived from the model estimates.

When evaluating gene expression data as potential predictors of outcomes, it is useful to model interactions between the genes. Logic regression can be used to discover and model interactions of binary explanatory variables, and combinations are created using Boolean operators ("and," "or" and "not") (Ruczinski et al., J. Comput. Graph. Stat., 12:475-511 (2003)). Since logic regression is limited to using binary explanatory variables, reasonable cutoff values needed to be established for each of the 54 experimental genes. For each gene, a separate Classification and Regression Tree (CART) model was fit to identify the best gene expression cutoffs to differentiate between patients with positive and negative SLN using the Gini rule for splitting, prior probabilities proportional to the observed data frequencies, and 0/1 losses. The AUC for these models ranged from 0.50 to 0.781. A total of 147 binary variables were created using all the breakpoints generated by the CART models and these breakpoints were then used to fit the logic regression.

Receiver operating characteristic (ROC) curves were constructed for the final prediction models. The predictive ability of each model was summarized by the area under curve (AUC), and the AUC estimates were compared between models using the DeLong, DeLong, and Clarke-Pearson non-parametric method for comparing the AUC for correlated ROC curves.

Model Validation

The performance of the prognostic model developed using the development cohort was validated in a new cohort by assessing the discrimination and calibration. Discrimination was assessed by quantifying the model's ability to discriminate between patients in the new cohort who do and do not have a positive SLNB using the area under the ROC curve. Calibration was assessed by grouping patients into 5 quintiles based on their predicted probabilities estimated by the model and comparing the median predicted probability in each quintile with the observed proportion of patients with a positive SNLB in that quintile.

The statistical analysis was performed SAS version 9.2 and R version 3.0.1. The CART analysis was performed using the rpart package (rpart: Recursive Partitioning, Version 4.1-1; Therneau and Atkinson). An introduction to recursive partitioning using the RPART routines: Technical Report 61, Section of Biostatistics, Mayo Clinic, Rochester). The logic regression used LogicReg package (LogicReg: Logic Regression, Version 1.5.5; Ruczinski et al., J. Comput. Graph. Stat., 12:475-511 (2003)).

Logic Regression

Logic regression fits regression models using one to five trees, and the trees can be composed of many leaves. Simulated annealing was used to explore possible logic regression models to find a good model. The technique starts by fitting a model built randomly using a specified number of leaves and trees. A new model is created by randomly permuting the current model by changing a leaf or Boolean operator. The performance of the current model is then compared to the new model. If the new model performs better, then it becomes the current model, and the process is repeated. Simulated annealing avoids local optima by controlling when inferior models were chosen. The null model randomization test was used to determine if there was a relationship between the 147 binary gene expression variables and SLN positivity. The optimal number of leafs and trees was determined using cross validation and permutation techniques.

Figure 8A:
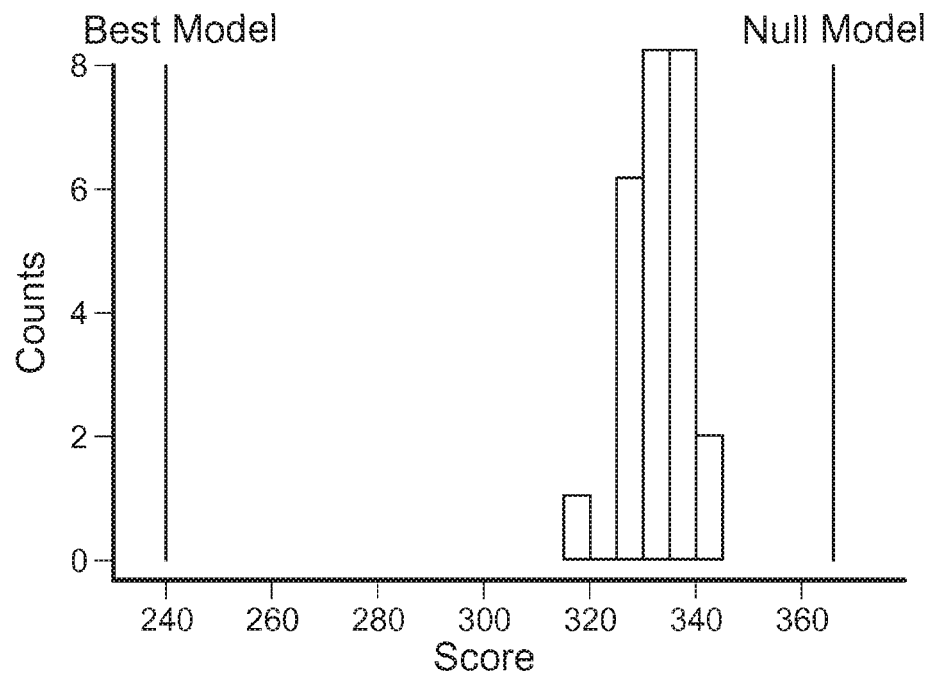
FIGS. 8A-8D depict logic regression.

The null model randomization test was used to determine if there was a relationship between the 147 binary gene expression variables and SLN positivity. First, the best model was fit for all biopsy samples using logic regression. Next, the SLN positivity outcome for all the patients was randomly reassigned and fit another model. The process of randomly reassigning the SLN positivity outcome and fitting a model was performed 25 times. FIG. 8A shows the histogram of the deviance scores from the models built using the randomized outcomes. The null model randomization test demonstrated there was a relationship between SLN positivity and gene expression since the deviance scores were all worse than the best model deviance scores.

Figure 8B:
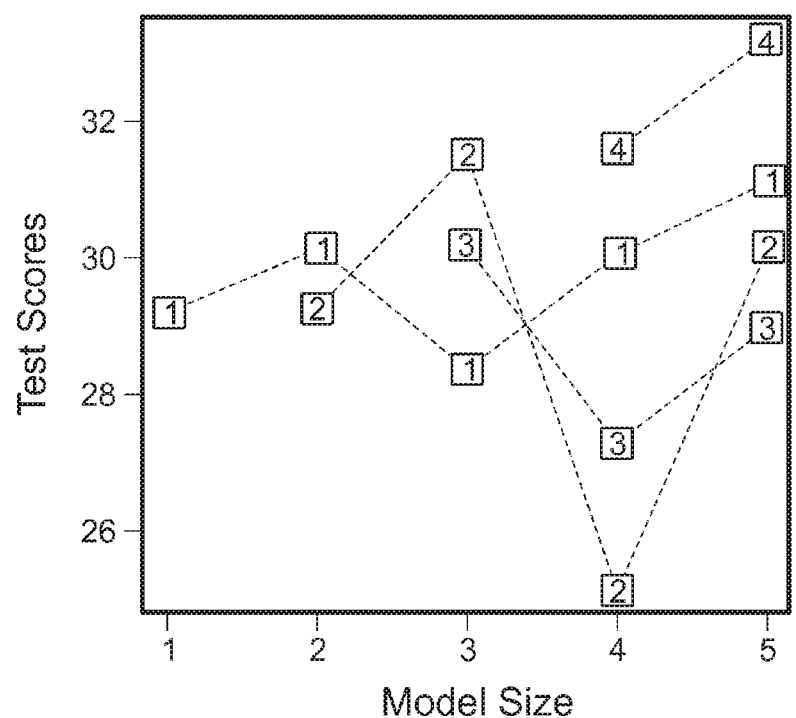
Figures 8C, 8D:
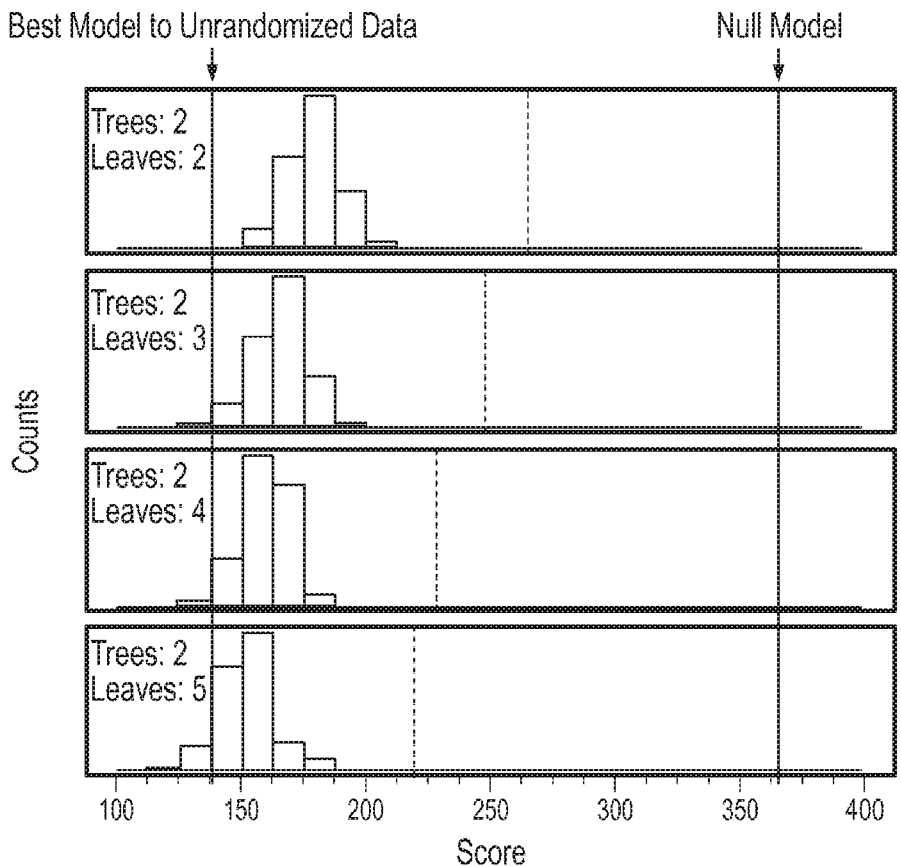

The optimal number of leafs and trees in the logic regression model was determined using cross validation and permutation techniques. Ten-fold cross validation was used to help determine the ideal model size given the data. FIG. 8B shows the deviance score for the test samples for different model configurations. The label in the square represents the number of trees used in the model. The x-axis indicates the number of binary variables or leaves used in the model. The best deviance score was obtained using a two-tree model using four binary explanatory variables. When more than four explanatory variables were used in the model, there may be an over-fitting issue since the test data deviance scores degrade when there are more than four explanatory variables. The permutation test was also used to confirm ideal model size given the data. The permutation test fits the best model given the model size. In each tree the binary variables are put together using "and," "or" and "not." It follows that each logic tree has a binary outcome. For a model having n trees the sample could be partitioned into 2n groups. With two trees, the sample was partitioned into four groups. The SLN outcomes were permuted by randomly reassigning the outcome within each of the four groups. The model was refit based on permuted data. Notice that the exact same model can be found within the permuted data. Models scoring better than the best model were likely because of fitting on noise. Models scores worse than the best model were likely caused by the model being too small. FIG. 8C shows this process repeated 1,000 times for each model size. Most of the permuted models with two leaves performed worse than the best model, indicating a larger model would be optimal. About 10% of the models using five leaves fit using permuted data outperformed the best model. It was recommended to choose the model size where the permuted outcome variables outperform the best model 5% to 20% of the time (Ruczinski et al., *J. Comput. Graph. Stat.*, 12:475-511 (2003)). The cross validation test and the permutation test indicate that the optimum model size was two trees using four or five binary variables. The formulas for the best fitting models involved two trees with a model size of 4 or 5 (FIG. 8D). The best four-leaf model considered $\beta 3$ integrin (ITGB3), cellular tumor antigen p53 (TP53), the laminin B1 chain (LAMB1), and tissue-type plasminogen activator (PLAT). The best five-leaf model considered the same four genes plus agrin (AGRN). Notice that the composition for one tree was exactly the same for both models ((LAMB1>250) or (PLAT>427)).

Results

Figure 9:
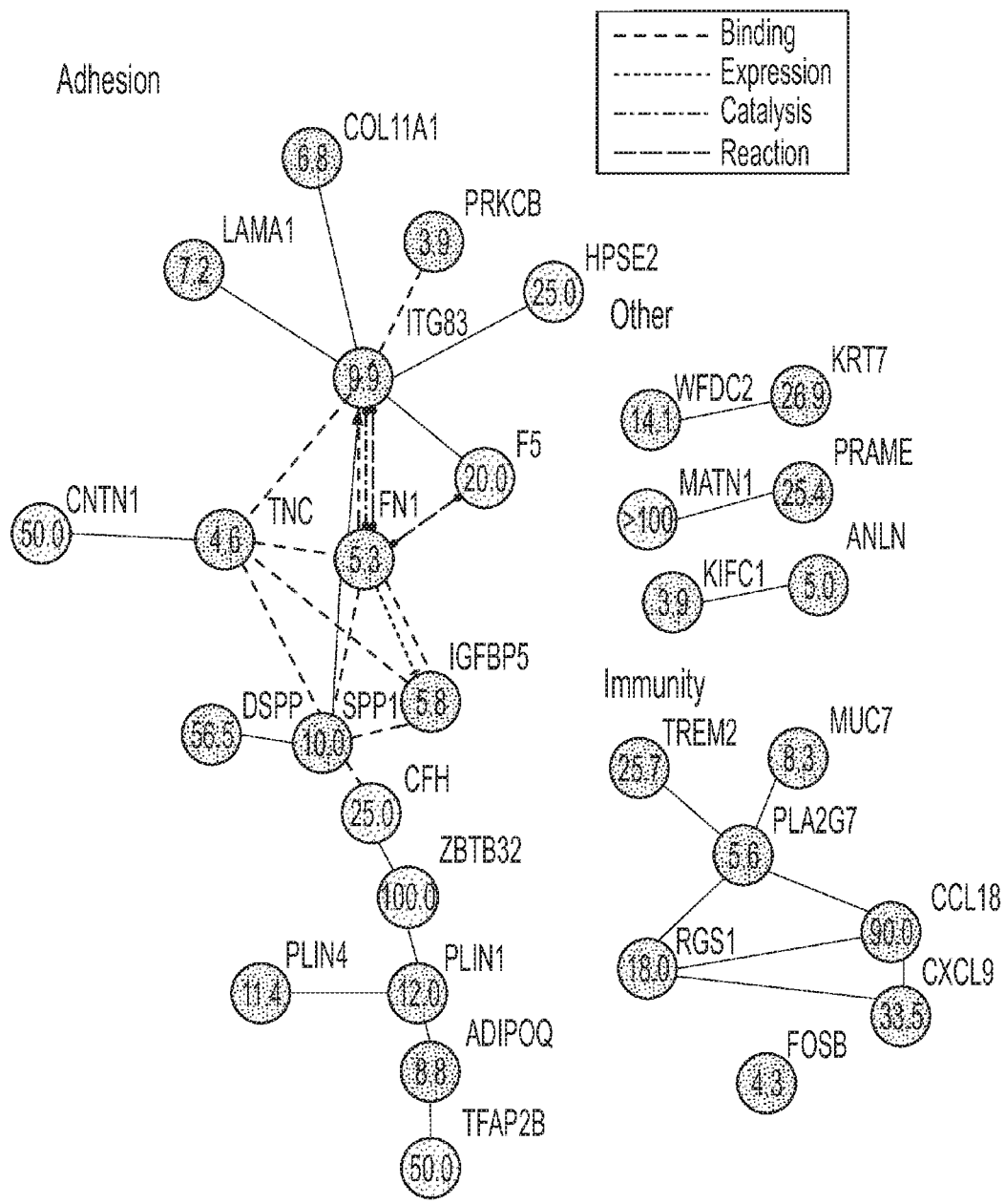
FIG. 9 depicts differential expression analysis by next-generation sequencing reveals that integrin adhesion genes are up-regulated in benign nevi vs. invasive melanoma. 160 of 15,413 genes were significantly regulated in benign nevi vs. invasive melanoma (FDR<0.01) as determined by next-generation sequencing (NGS). Functional relationships between these genes were mapped by the STRING database. Two main functional clusters emerged; the largest was related to integrin-linked cell adhesion. The particularly indicated circles indicate gene up-regulation; other circles indicate down-regulation. Numbers indicate fold-change, malignant over benign.

This investigation started by identifying functional networks of differentially expressed genes in benign melanocytic lesions vs. invasive melanoma. In a pilot study, three patients with benign nevi were age and gender-matched one-to-one to a patient with a primary skin melanoma that had metastasized regionally. A total of 15,413 genes were identified and measured by next-generation sequencing (NGS) of patient biopsy-derived RNA. Differential gene expression analysis yielded 160 genes with a false-discovery rate (FDR)<0.01. These were entered into the STRING database to identify functional gene networks. Genes that were without known functional relationships to other genes were hidden. Two clusters with more than two nodes emerged; the largest was linked to integrin cell adhesion (FIG. 9). Within that cluster, ($\beta 3$ integrin (ITGB3) had the lowest FDR and the highest connectivity.

Figure 10:
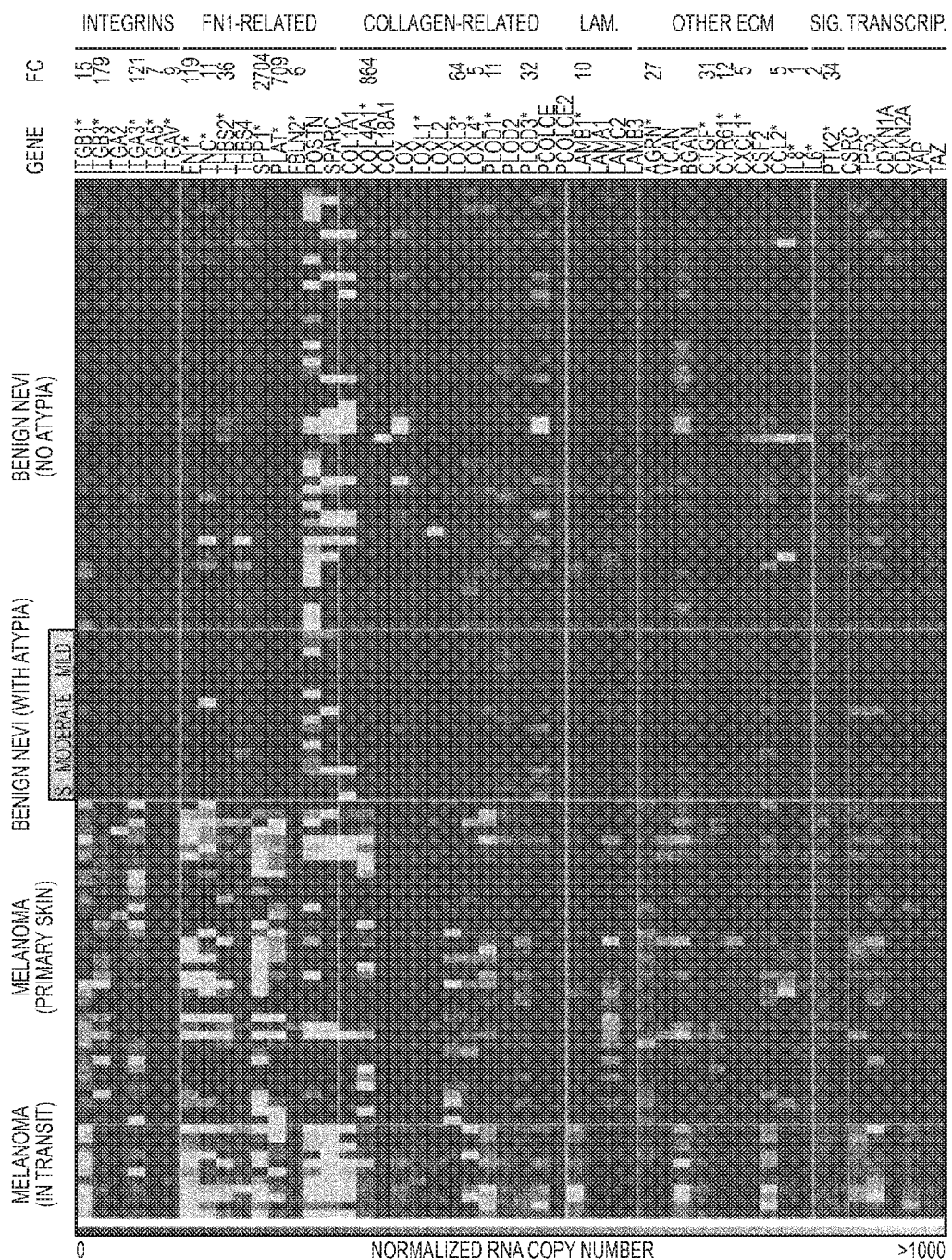
FIG. 10 illustrates that integrin adhesion genes are overexpressed in invasive melanoma vs. non-invasive precursor lesions. Confirmation of NGS results by quantitative PCR. Genes with significant regulation (p<0.001, Mann-Whitney U Test) are bolded and marked with an asterisk. FC, fold change; S, severe atypia.

Next, the objective was to confirm that genes involved in integrin cell adhesion are up-regulated in invasive melanoma. A test set of 73 benign nevi (53 were without histological atypia, 7 were with mild, 11 with moderate and two with severe atypia), 38 primary skin melanoma that had metastasized regionally (median Breslow depth of 3 mm; IQR, 2 to 4 mm), and 11 in-transit regional melanoma metastases was assembled. A method for determining copy number of 77 specific targets in 62 genes (54 experimental and 8 control genes) by quantitative PCR was established as described herein. Genes were categorized as follows: i) integrin adhesion receptor subunits; ii) FN1 and related extracellular matrix (ECM) components; iii) collagen genes and enzymes that facilitate the cross-linking of collagens; iv) laminin subunits; v) other ECM components including those of a pro-inflammatory DNA damage response (Coppe et al., *PLoS biology*, 6:e301 (2008)); vi) integrin-activated kinases, and vii) cell cycle related. Genes with significant regulation between benign and malignant were mainly in the categories of integrins and FN1 and related ECM components, thus confirming NGS results (FIG. 10). ($\beta 3$ integrin was with the highest fold change of all tested integrin subunits.

The following was performed to assess whether adhesion gene expression in tissue sections predicted metastasis to SLN and to determine whether the method outperformed the current clinical gold standard for predicting metastasis risk, i.e., Breslow invasion depth (Breslow, *Annals of Surg.*, 172:902 (1970)). The model development cohort consisted of a total of 360 thin and intermediate thickness primary melanoma (Breslow depth≤4 mm) of all histologic types with a SLN biopsy within 90 days of their diagnosis (Table 14). To exclude minimal risk lesions, thin melanoma (Breslow depth≤1 mm; T classification 1) without additional risk factors (ulceration, mitoses, patient age<40) were not considered. Thick melanoma (Breslow depth>4 mm; T classification 4) were excluded because they frequently metastasize to SLN and the clinical utility of a molecular test is low.

TABLE 14

Summary of histologic types of melanoma that triggered a SLN biopsy.

| Histologic Type | No. (%) |
|---|---|
| Superficial Spreading | 180 (50.0%) |
| Nodular | 70 (19.4%) |
| Unclassifiable | 30 (8.3%) |
| Desmoplastic | 16 (4.4%) |
| Lentigo Maligna | 15 (4.2%) |
| Spindled | 13 (3.6%) |
| Acral Lentiginous | 9 (2.5%) |
| Spitzoid | 4 (1.1%) |
| Nevoid | 3 (0.8%) |
| Dermal | 1 (0.3%) |
| Not documented | 19 (5.3%) |

Table 15 summarizes the clinical and pathologic factors that were evaluated univariately for an association with SLN positivity. Ulceration, Breslow depth, and age were identified as independently associated with SLN positivity (Table 16, Model A). Logic regression models were fit utilizing 147 binary variables derived from 54 experimental genes and evaluated using the breakpoints generated by the CART models for the 54 genes. The best four-leaf model considered 3 integrin (ITGB3), cellular tumor antigen p53 (TP53), the laminin B1 chain (LAMB1), and tissue-type plasminogen activator (PLAT). SLN positivity within each of these four categories is summarized at the bottom of Table 15. The model results for a combined model including both the clinical/pathologic factors and the gene expression parameters are presented as model B in Table 16.

TABLE 15

Summary of the association of clinical and pathologic factors with SLN positivity based on 360 SLN biopsies.

| Factor | Positive SLNB N (%) | Chi-square test p value |
|---|---|---|
| Gender | | 0.84 |
| Male (N = 225) | 47 (20.9%) | |
| Female (N = 135) | 27 (20.0%) | |
| Age (years) | | <0.001 |
| 16- <40 (N = 55) | 16 (29.1%) | |
| 40- <59 (N = 112) | 33 (29.5%) | |
| 60+ (N = 193) | 25 (13.0%) | |
| Ulceration | | <0.001 |
| No (N = 295) | 50 (16.9%) | |
| Yes (N = 65) | 24 (36.9%) | |
| Breslow depth (mm) | | <0.001 |
| 0.50-1 (N = 93) | 6 (6.4%) | |
| 1.01-2 (N = 177) | 31 (17.5%) | |
| 2.01-4 (N = 90) | 37 (41.1%) | |
| Mitotic rate | | 0.12 † |
| Missing (N = 14) | 4 | |
| Absent (N = 42) | 4 (9.5%) | |
| 1-6 (N = 246) | 51 (20.7%) | |
| >6 (N = 58) | 15 (25.9%) | |
| Tumor invading lymphocytes | | 0.37 † |
| Missing (N = 31) | 12 | |
| No (N = 86) | 19 (22.1%) | |
| Yes (N = 243) | 43 (17.7%) | |
| Angiolymphatic invasion | | 0.28 |
| No (N = 344) | 69 (20.1%) | |
| Yes (N = 16) | 5 (31.3%) | |
| 4-level gene score | | <0.001 |
| A: NOT (lamb1 >250 or plat >427) and NOT (itgb3 >10 and tp53 ≤50) (N = 237) | 10 (4.2%) | |
| B: (lamb1 >250 or plat >427) but NOT (itgb3 >10 and tp53 ≤50) (N = 68) | 26 (38.2%) | |
| C: (itgb3 >10 and tp53 ≤50) but NOT (lamb1 >250 or plat >427) (N = 34) | 18 (52.9%) | |
| D: (lamb1 >250 or plat >427) AND (itgb3 >10 and tp53 ≤50) (N = 21) | 20 (95.2%) | |

† P-values were calculated based on the subset of patients with non-missing values.

TABLE 16

Multivariable logistic regression analyses of characteristics associated with SLN positivity.

| | Model A | | Model B | | Model C | |
|---|---|---|---|---|---|---|
| Factor | Adjusted OR (95% CI) | p-value | Adjusted OR (95% CI) | p-value | Adjusted OR (95% CI) | p-value |
| Ulceration | | 0.026 | | 0.25 | | 0.39 |
| No | Referent | | Referent | | Referent | |
| Yes | 2.11 (1.10, 4.06) | | 1.58 (0.73, 3.44) | | 1.38 (0.66, 2.88) | |
| Breslow depth (mm) | | <0.001 | | 0.13 | | 0.036 |
| 0.50-1 | Referent | | Referent | | Referent | |
| 1.01-2 | 3.33 (1.31, 8.44) | | 1.28 (0.46, 3.59) | | 1.50 (0.54, 4.21) | |
| 2.01-4 | 11.46 (4.34, 30.27) | | 2.52 (0.84, 7.58) | | 3.30 (1.11, 9.77) | |
| Patient age (years) | | <0.001 | | 0.001 | | 0.001 |
| 16-<40 | 3.85 (1.75, 8.50) | | 6.18 (2.24, 17.06) | | 5.14 (1.99, 13.25) | |
| 40-<59 | 3.47 (1.83, 6.59) | | 2.92 (1.31, 6.52) | | 2.91 (1.41, 6.00) | |
| 60+ | Referent | | Referent | | Referent | |
| Gene score | | | | <0.001 | | <0.001 |
| A | — | | Referent | | Referent | |
| B | — | | 13.17 (5.53, 31.39) | | | |
| C | — | | 12.27 (4.52, 33.33) | | 17.32 (8.02, 37.41) | |
| D | — | | 236.60 (36.95, >999) | | | |

Figure 11A:
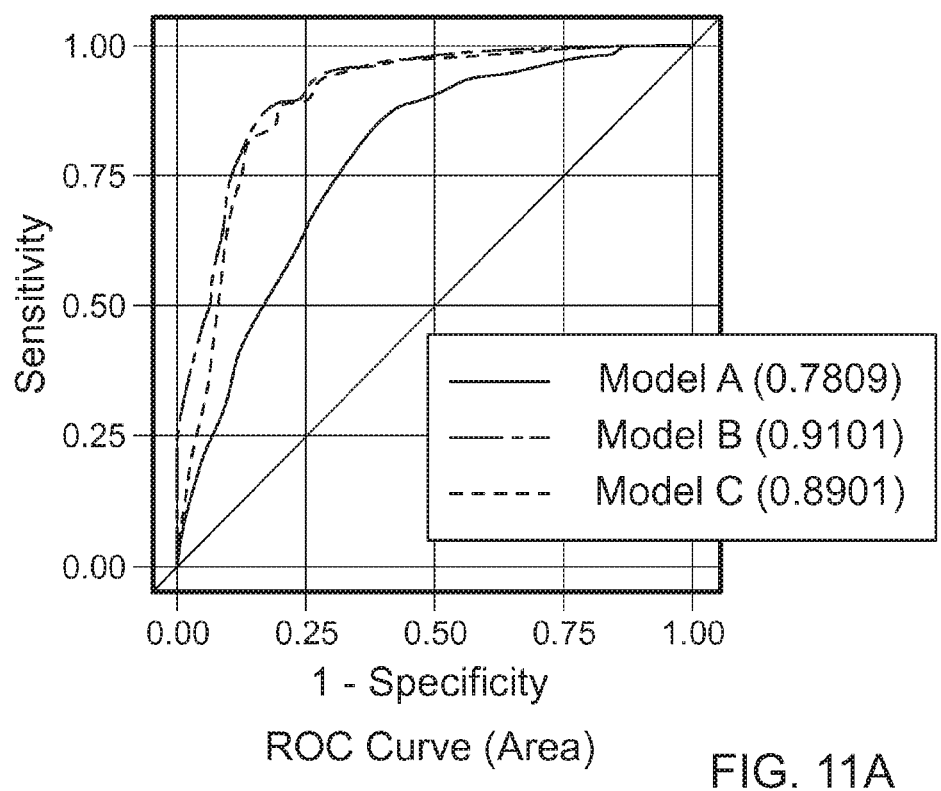
FIGS. 11A-11C illustrate that integrin adhesion genes predict SLN metastasis.
Figure 11B:
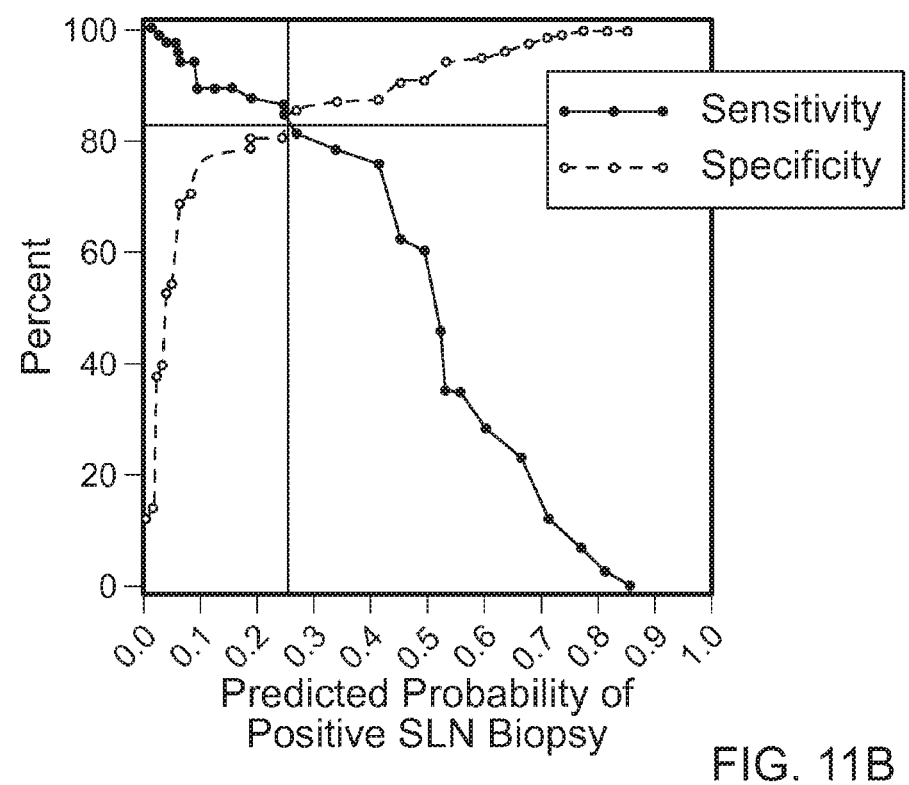
Figure 11C:
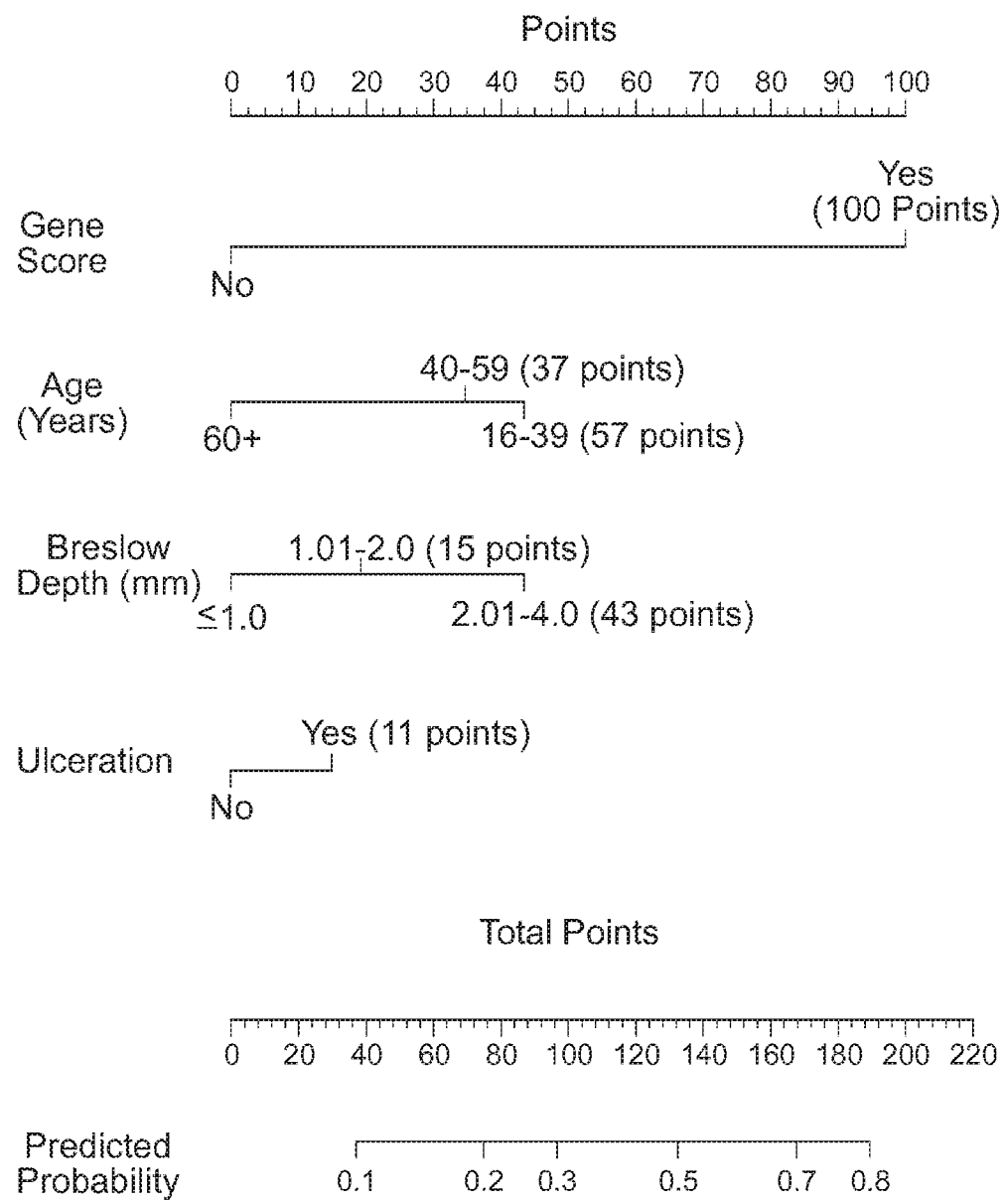

It was subsequently decided to collapse the four categories in the gene model into two categories, which yielded a simpler model without loss of overall predictive ability (Table 16, model C). The receiver operating characteristic (ROC) curves for the three models are displayed in FIG. 11A. The overall predictive ability of the combined model as measured by the area under the curve (AUC) or c-index was significantly greater for model C compared to model A (0.89 vs. 0.77, p<0.001). FIG. 11B depicts the sensitivity and specificity of model C as the level of the predicted probability of a positive SLNB used to define a positive test was varied. A predicted probability of 0.255 corresponds to a sensitivity and specificity of 82%. A nomogram constructed from model C is presented in FIG. 11C. For a given patient, points were assigned to each of the variables, and a total score was derived. The total points score corresponded to a predicted probability of positive SLN biopsy.

The model validation cohort included 104 patients. Table 17 summarizes the association of the clinical and pathologic factors with SLN positivity, separately for the two cohorts. The discriminative ability of the predictive model was excellent when applied to the validation cohort (AUC 0.92, 95% CI 0.87-0.97). Table 18 compares the predicted and observed rate of positive SLNB for the 5 quintiles defined by the distribution of the predicted probabilities. The two rates track consistently across the 5 quintiles suggesting reasonable calibration.

TABLE 17

Summary of the association of clinical and pathologic factors with SLN positivity, separately for the model development and model validation cohorts.

| Factor | Model development cohort | | Model validation cohort | |
|---|---|---|---|---|
| | Positive SLNB N (%) | p value† | Positive SLNB N (%) | p value† |
| Gender | | 0.84 | | 0.54 |
| Male | 47/225 (20.9) | | 22/78 (28.2) | |
| Female | 27/135 (20.0) | | 9/26 (34.6) | |
| Age (years) | | <0.001 | | 0.17 |
| 16- <40 | 16/55 (29.1) | | 3/5 (60.0) | |
| 40- <59 | 33/112 (29.5) | | 12/34 (35.3) | |
| 60+ | 25/193 (13.0) | | 16/65 (24.6) | |
| Ulceration | | <0.001 | | 0.35 |
| No | 50/295 (16.9) | | 23/83 (27.7) | |
| Yes | 24/65 (36.9) | | 8/21 (38.1) | |
| Breslow depth (mm) | | <0.001 | | 0.035 |
| 0.50-1 | 6/93 (6.4) | | 5/28 (17.9) | |
| 1.01-2 | 31/177 (17.5) | | 10/41 (24.4) | |
| 2.01-4 | 37/90 (41.1) | | 16/35 (45.7) | |
| Mitotic rate | | 0.12 | | 0.21 |
| Missing | 4/14 | | 5/14 | |
| Absent | 4/42 (9.5) | | 0/7 (0.0) | |
| 1-6 | 51/246 (20.7) | | 21/68 (30.9) | |
| >6 | 15/58 (25.9) | | 5/15 (33.3) | |
| Tumor invading lymphocytes | | 0.37 | | 0.011 |
| Missing | 12/31 | | 8/26 | |
| No | 19/86 (22.1) | | 10/19 (52.6) | |
| Yes | 43/243 (17.7) | | 13/59 (22.0) | |
| Angiolymphatic invasion | | 0.28 | | 0.89 |
| No | 69/344 (20.1) | | 30/101 (29.7) | |
| Yes | 5/16 (31.3) | | 1/3 (33.3) | |
| 4-level gene score | | <0.001 | | <0.001 |
| A: NOT (lamb1 >250 or plat >427) and NOT (itgb3 >10 and tp53 ≤50) | 10/237 (4.2%) | | 1/63 (1.6) | |
| B: (lamb1 >250 or plat >427) but NOT (itgb3 >10 and tp53 ≤50) | 26/68 (38.2%) | | 18/25 (72.0) | |
| C: (itgb3 >10 and tp53 ≤50) but NOT (lamb1 >250 or plat >427) | 18/34 (52.9%) | | 3/4 (75.0) | |
| D: (lamb1 >250 or plat >427) AND (itgb3 >10 and tp53 ≤50) | 20/21 (95.2%) | | 9/12 (75.0) | |

†P-values were calculated using the chi-square rest based on the subset of patients with non-missing values.

TABLE 18

Summary of the predicted and observed rate of positive SLNB for the 5 quintiles defined by the distribution of the predicted probabilities.

| Quintile defined based on the predicted probability | Predicted rate of positive SLNB† | Observed rate of positive SLNB |
| --- | --- | --- |
| ≤0.02 | 1.4% | 0/15 (0%) |
| >0.02-0.04 | 2.1% | 0/23 (0%) |
| >0.04-0.16 | 5.9% | 0/24 (0%) |
| >0.16-0.45 | 30.7% | 17/22 (77.3%) |
| >0.45 | 65.4% | 14/20 (70.0%) |

†Median predicted probability in each quintile

Figure 12A:
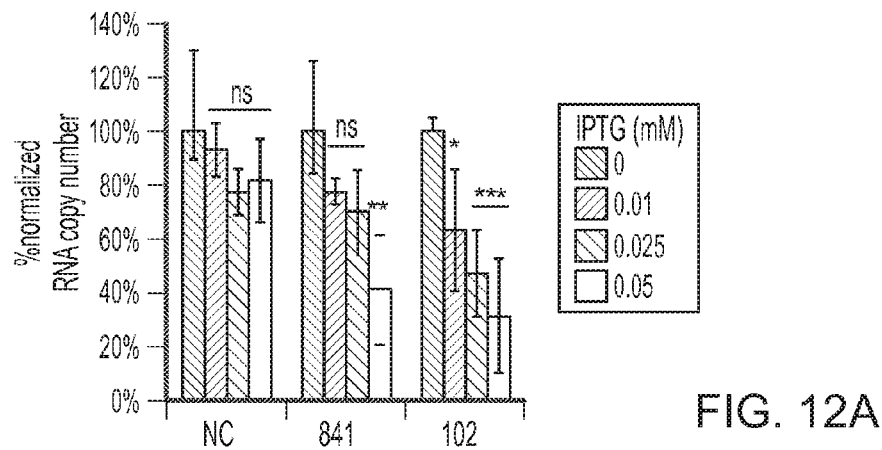
FIGS. 12A-12D illustrate that IPTG-inducible shRNA effectively knocks down FAK in a B-rafV600E melanoma cell line.
Figure 12B:
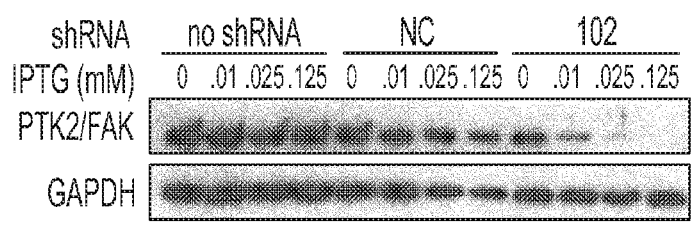
Figure 12C:
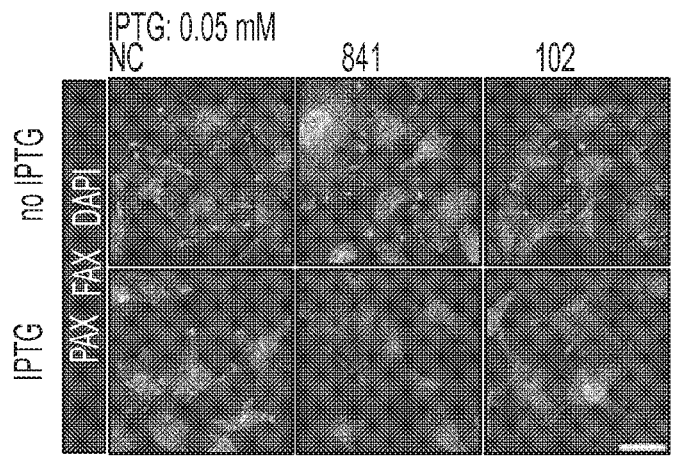
Figure 12D:
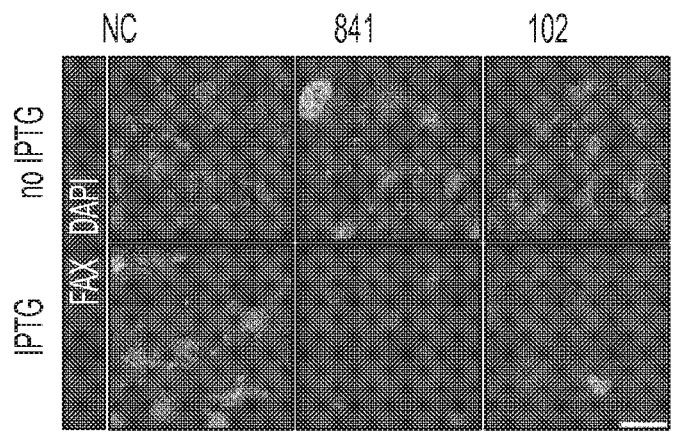
Figure 13A:
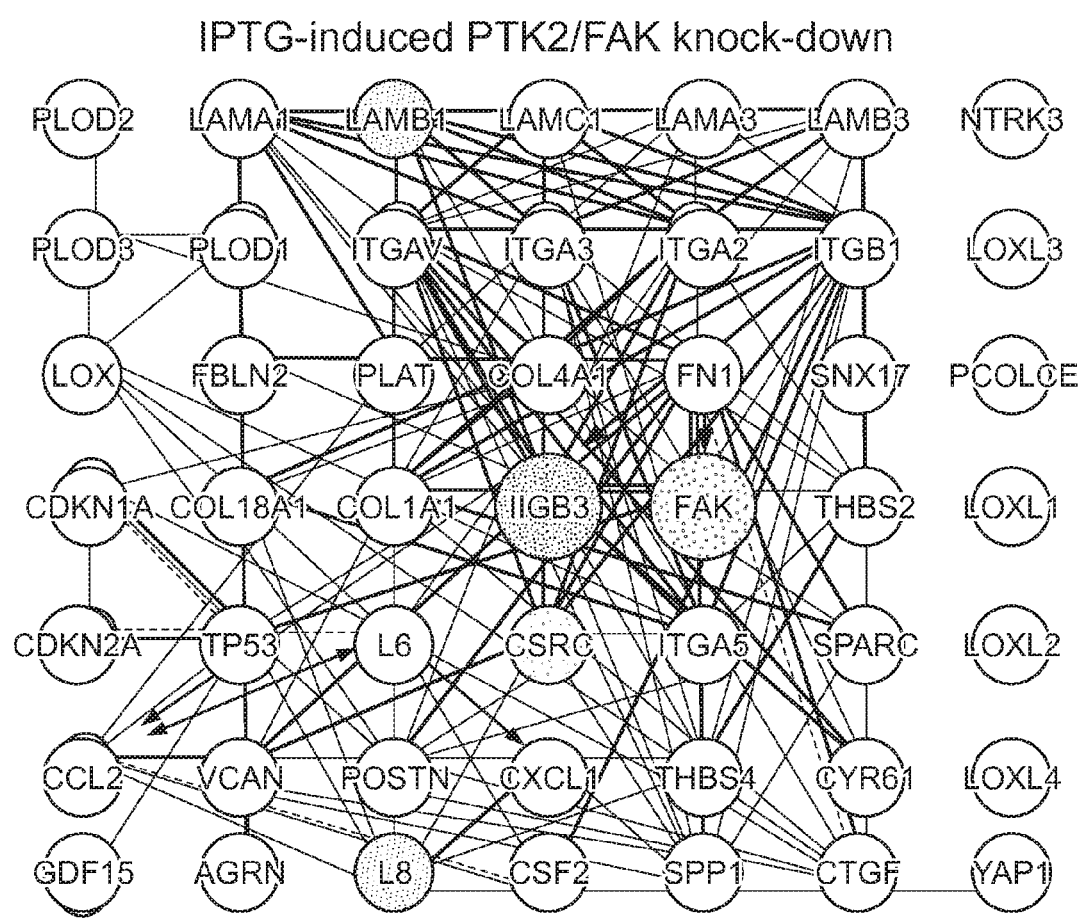
FIGS. 13A-13P illustrate B-raf$^V$600E inhibits FAK to promote integrin surface expression.
Figure 13B:
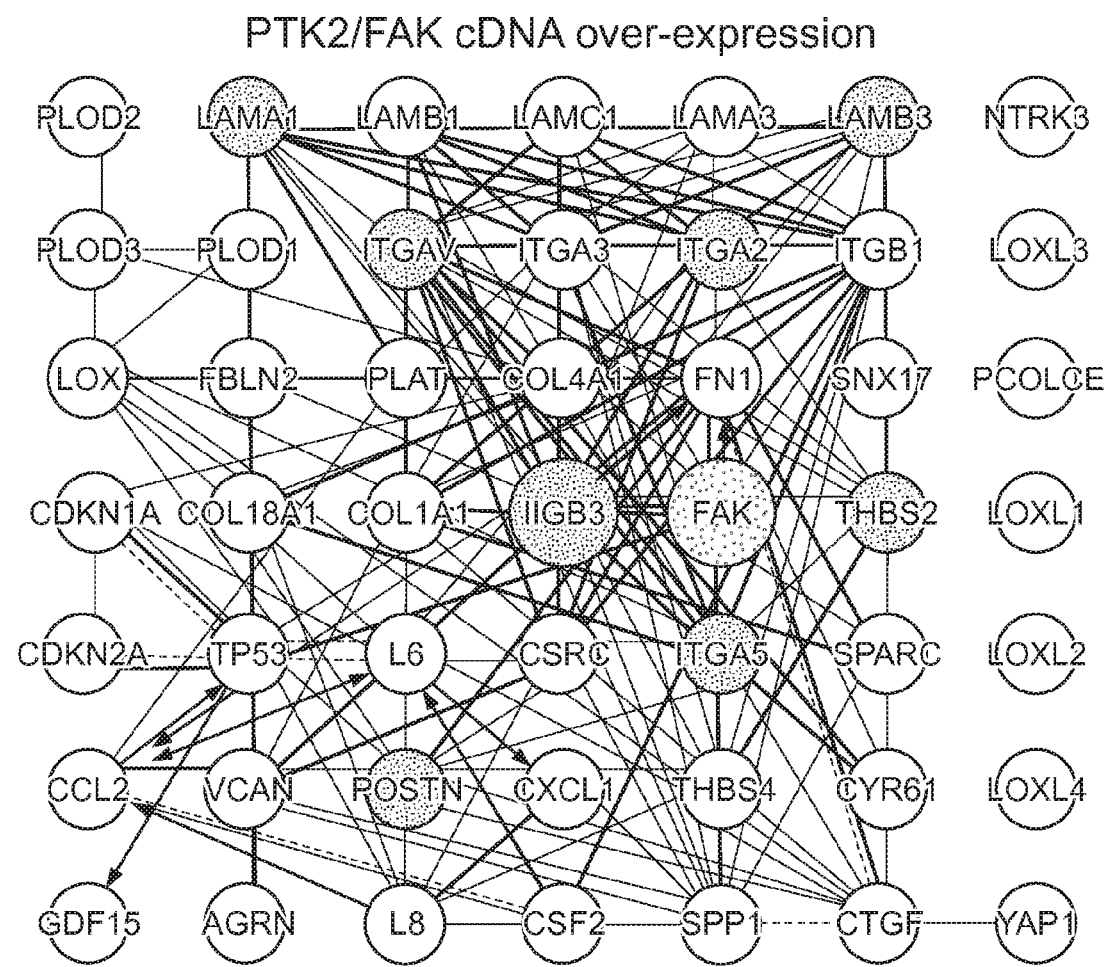
FIG. 13B: WM858 cells were transfected with FAK or EGFP cDNA. Regulated genes, FAK over EGFP cells, are shown in orange (up) or blue (down) (n=4).
Figure 13F:
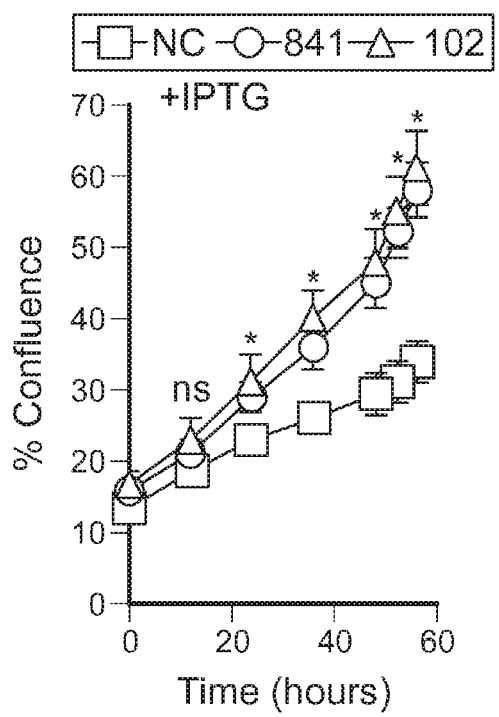
FIGS. 13F and 13G: Proliferation speed in the absence (FIG. 13F) or presence (FIG. 13G) of FAK shRNAs; mean.+−.s.d.; n=8; *, p<0.05; p values, Student's t-test; ns, not significant.
Figure 13G:
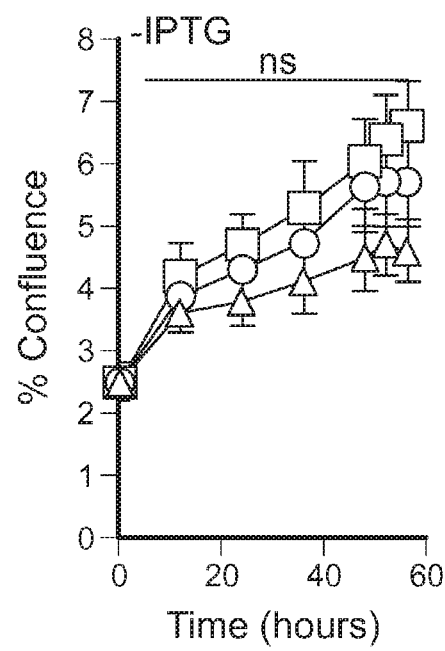
Figure 13H:
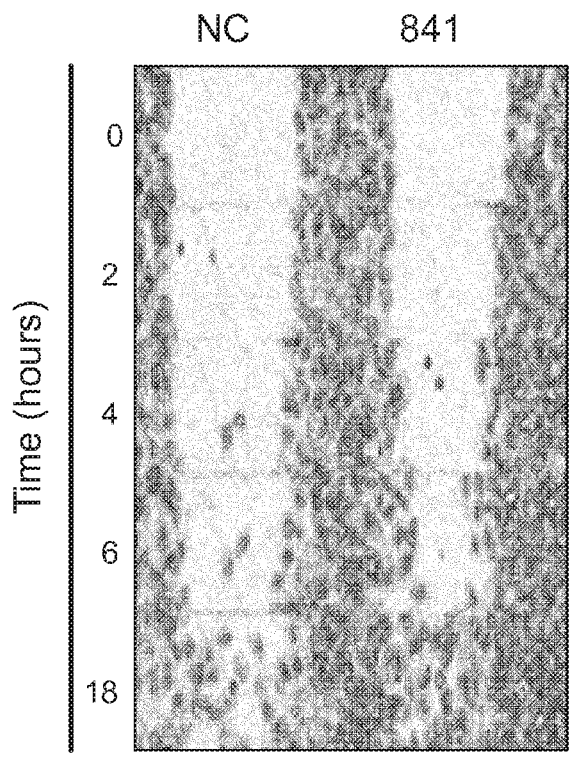
FIGS. 13H and 13I: Scratch wound healing in IPTG-induced cells; representative experiment (n=3).
Figure 13I:
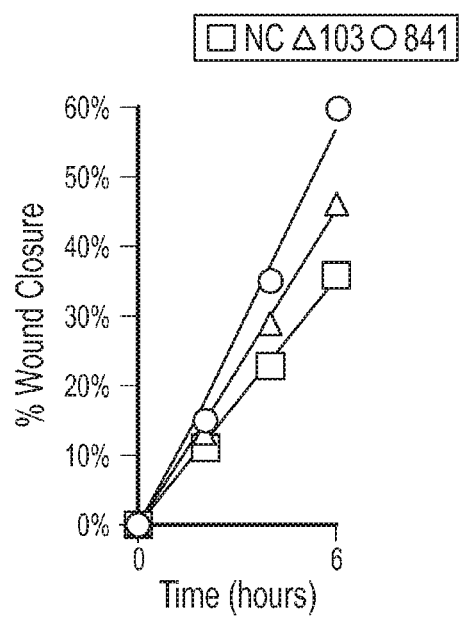
Figure 13J:
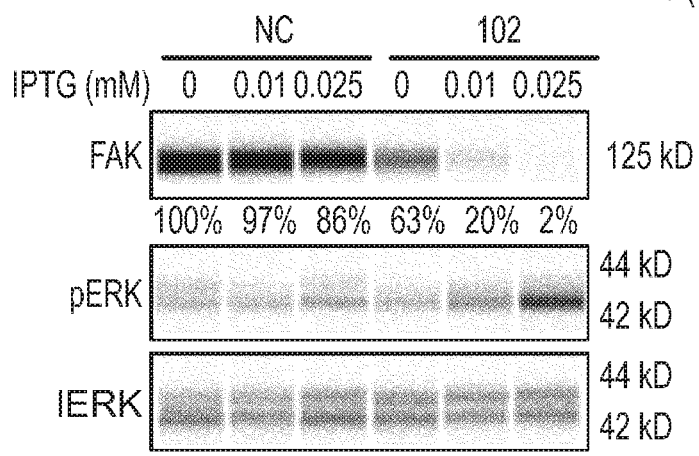
FIGS. 13J and 13K: Effect of IPTG-induced FAK knock-down on total (t) and phospho (p)-ERK; mean.+−.s.d.; n=4; *, p<0.05; p values, Student's t-test.
Figure 13K:
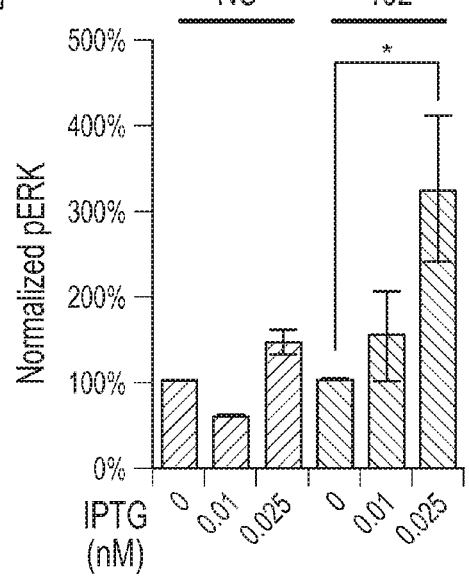
Figure 13L:
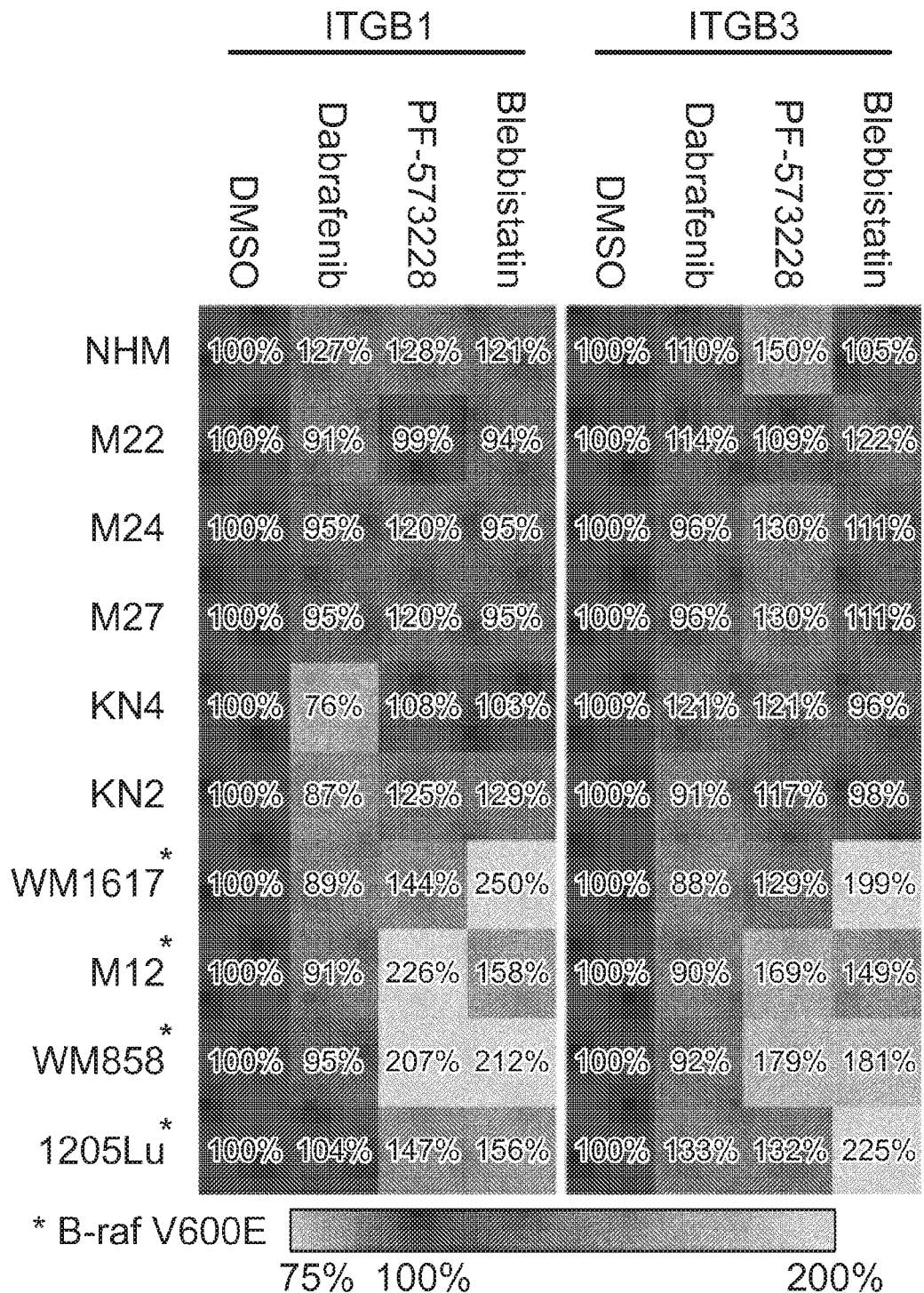
FIG. 13L: Cell surface β1 and β3 integrin expression (flow cytometry) in B-raf$^V$600E and wild-type cells after overnight drug incubation; % expression relative to DMSO is shown.
Figure 13M:
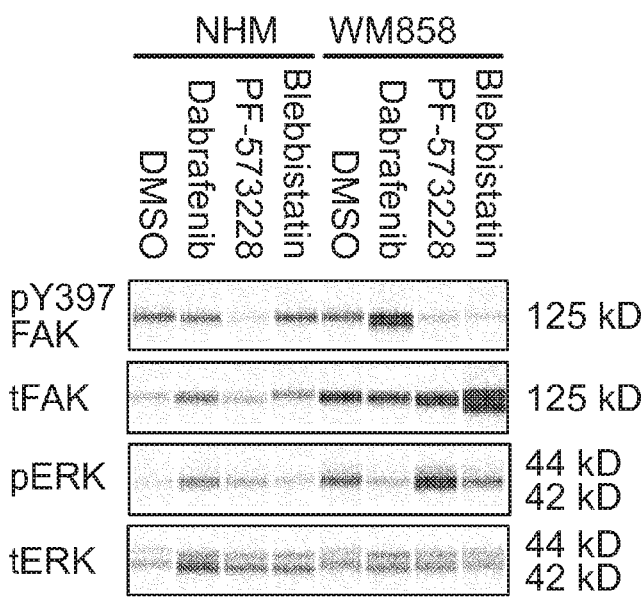
FIGS. 13M-13O: FAK/ERK levels in NHM and WM858 after overnight drug incubation (FIG. 13M); quantification of FAK (FIG. 13N) and ERK phosphorylation (FIG. 13O); mean.+−.s.d.; n=4; *, p<0.05; p values, Student's t-test.
Figure 13N:
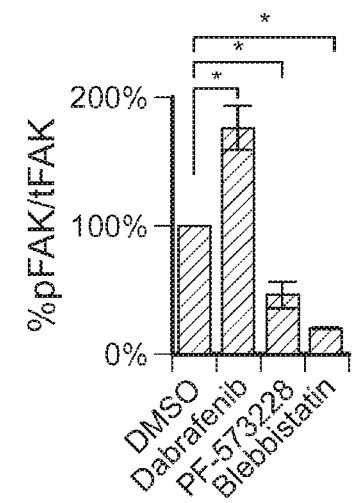
Figure 13O:
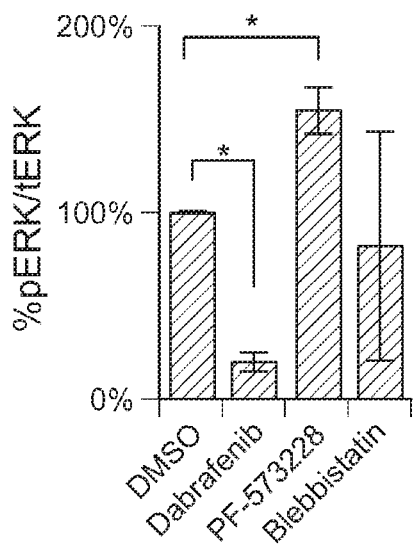
Figure 13P:
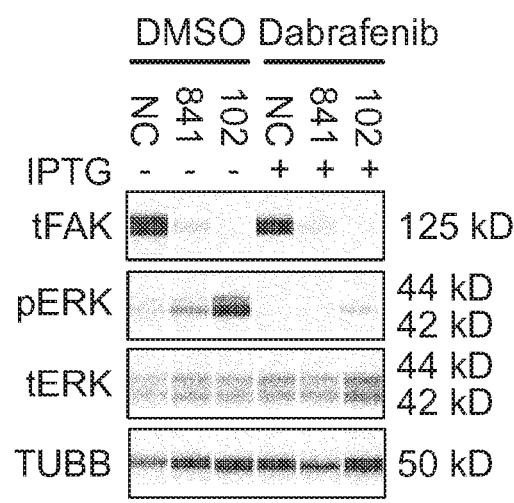

The following was performed to determine whether the expression of β3 integrin and other adhesion-related genes in melanoma is influenced by focal adhesion kinase (FAK), a key transducer of integrin signals and novel cancer therapy target (Infante et al., *J. Clin. Oncol.* 30:1527-33 (2012)). To test whether FAK controls adhesion gene expression, B-rafV600E WM858 cells were engineered to contain IPTG-inducible short hairpin RNA (shRNA) against FAK. FAK knock-down was highly effective at the RNA and protein level at concentrations equal to or exceeding 0.025 mM IPTG (Figure S3A-B). FAK could not be visualized in focal adhesions after 0.05 mM IPTG for 5 days (FIGS. 12C and 12D). PYK2, a FAK-like tyrosine kinase, could not be detected in WM858 cells, irrespective of endogenous FAK levels. WM858 cells carrying control (NC) or FAK-specific shRNAs (841 and 102) were then exposed to IPTG for 5 days, and changes in adhesion gene expression were subsequently quantified by PCR. FAK-specific shRNA increased β3 integrin expression 2-fold (FIG. 13A). Vice versa, over-expression of a FAK cDNA led to a 2-fold down-regulation of β3 integrin and other integrin subunits (FIG. 13B). At the protein level, FAK knock-down led to an increase in cell surface β3 integrin (FIGS. 13C and 13D), which was accompanied by a noticeable increase in focal adhesion size and number (FIG. 13E). An increase in proliferation was observed when FAK levels were reduced (FIGS. 13F and 13G) as was a faster scratch wound healing (FIGS. 13H and 13I). In line with these data, FAK knock-down was found to induce extracellular regulated kinases (ERK) activity (FIGS. 13J and 13K). FAK inhibition by the small molecule FAK kinase inhibitor PF-573228 or blebbistatin, a drug that inhibits FAK by blocking myosin II-dependent contractile forces (Seo et al., *Biomaterials* 32:9568-75 (2011)), induced β3 and also β1 integrin surface levels in B-rafV600E, but not B-raf wild-type melanoma cells (FIG. 13L). In contrast, Dabrafenib, a B-raf inhibitor and established single agent therapeutic of metastatic melanoma, reduced integrin levels in most melanoma cells but not in NHM (FIG. 13L). While FAK inhibitors effectively suppressed FAK tyrosine (Y) 397 auto-phosphorylation in melanoma cells, Dabrafenib increased FAK phosphorylation (FIG. 13M), suggesting that in melanoma B-raf promotes integrin expression by inhibiting FAK, which in turn provides a scaffold for active ERK. In line with this hypothesis, PF-573228 was found to induce ERK activity (FIGS. 13M-13O). Moreover, Dabrafenib-induced blockage of ERK activity could be partially reversed by a complete FAK knock-down in 102 cells (FIG. 13P).

As described herein, a completely customizable high-density microfluidic PCR platform was used to allow for the quantification of multiple genes by repeat measurements. For example, at least 26 individual PCR reactions were performed per patient sample to measure house-keeping genes. To account for RNA contamination by basal keratinocytes—a cell type with stem cell-like features and high levels of adhesion gene expression—keratin 14 (KRT14), a basal keratinocyte marker, was quantified. KRT14 copy number was multiplied with a gene specific, per-copy-of-KRT14 contamination factor that was pre-determined by analyzing normal skin; and the product of this calculation was used to correct for keratinocyte background. In addition, melanocyte markers were routinely assayed to quantify melanocyte content in processed tissue. Aside from through-put, the methods provided herein have several other advantages. First, they are quantitative. This is an advantage over IHC or fluorescent in-situ hybridization (FISH), where the signal intensity is difficult to normalize and/or image analysis is subjective and time consuming. Second, they are based on the quantitation of RNA, which in contrast to DNA carries epigenetic information. Third, they are devoid of array-based hybridization steps, which can lead to hybridization errors and noise. Fourth, they are easily adjusted to include additional genes of interest.

The results provided herein demonstrate that the best four-leaf molecular model for predicting SLN metastasis considered β3 integrin, the laminin B1 chain, tissue-type plasminogen activator and tumor antigen p53. The overall predictive ability of a combined model that included molecular parameters was significantly greater than a model that only included clinical/pathologic factors (0.89 vs. 0.77, $p<0.001$).

The results provided herein also demonstrate that FAK inhibition induces the expression of integrins, induces the size of focal adhesions, and stimulates proliferation and mitogen activated kinases. These effects were strongest in B-raf$^V$600E cells, likely because mutant B-raf inhibits FAK to trigger integrin expression.

The two-tree two-leaf model was generated using logic regression and slow cooling on simulated annealing parameters.

Figure 16:
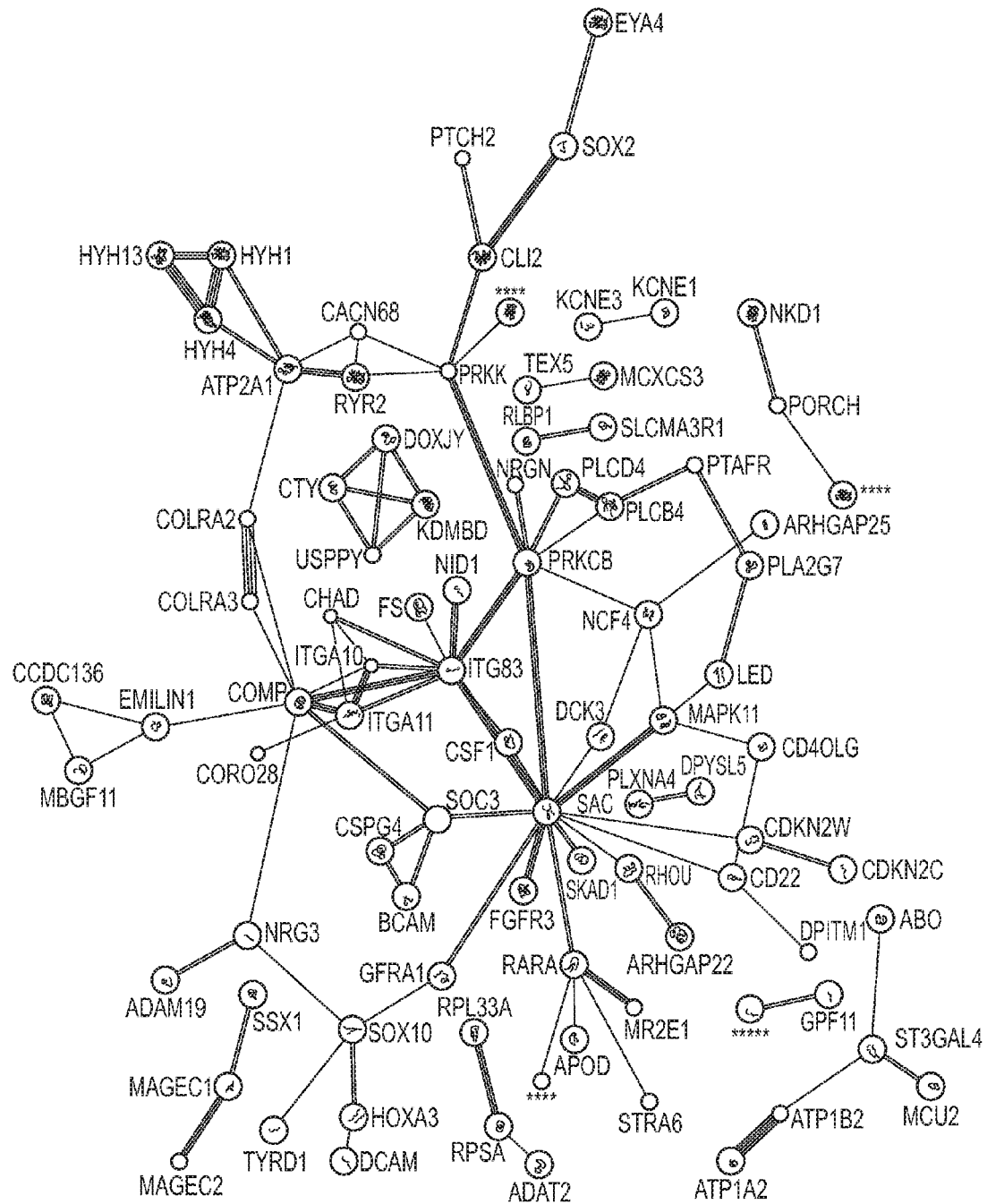
FIG. 16 illustrates differential gene expression by NGS in a cohort of four patients with primary skin melanoma that had not metastasized (median Breslow depth: 2.6 mm) and three patients that had metastasized regionally (median Breslow depth: 2.3 mm). Out of a total of 15,196 genes, 208 genes were identified with a FDR<0.01. ITGB3 as well as SRC, a downstream effector of β3 integrin, one formed the center of a functional network deregulated in regionally metastatic vs. non-metastatic melanoma. Genes (nodes) functionally disconnected to any of the other genes were hidden. Functional relationships between genes are indicated by lines and were plotted using the STRING database.

Additional analysis of samples by next generation sequencing using a cohort of four patients with primary skin melanoma that had not metastasized (median Breslow depth: 2.6 mm) and three patients that had metastasized regionally (median Breslow depth: 2.3 mm) yielded a total of 208 differentially regulated genes out of a total of 15,196 measured genes. ITGB3 as well as SRC, a key downstream effector of β3 integrin, formed the center of a functional network deregulated in regionally metastatic vs. non-metastatic melanoma (FIGS. 16 and 17).

Figure 17:
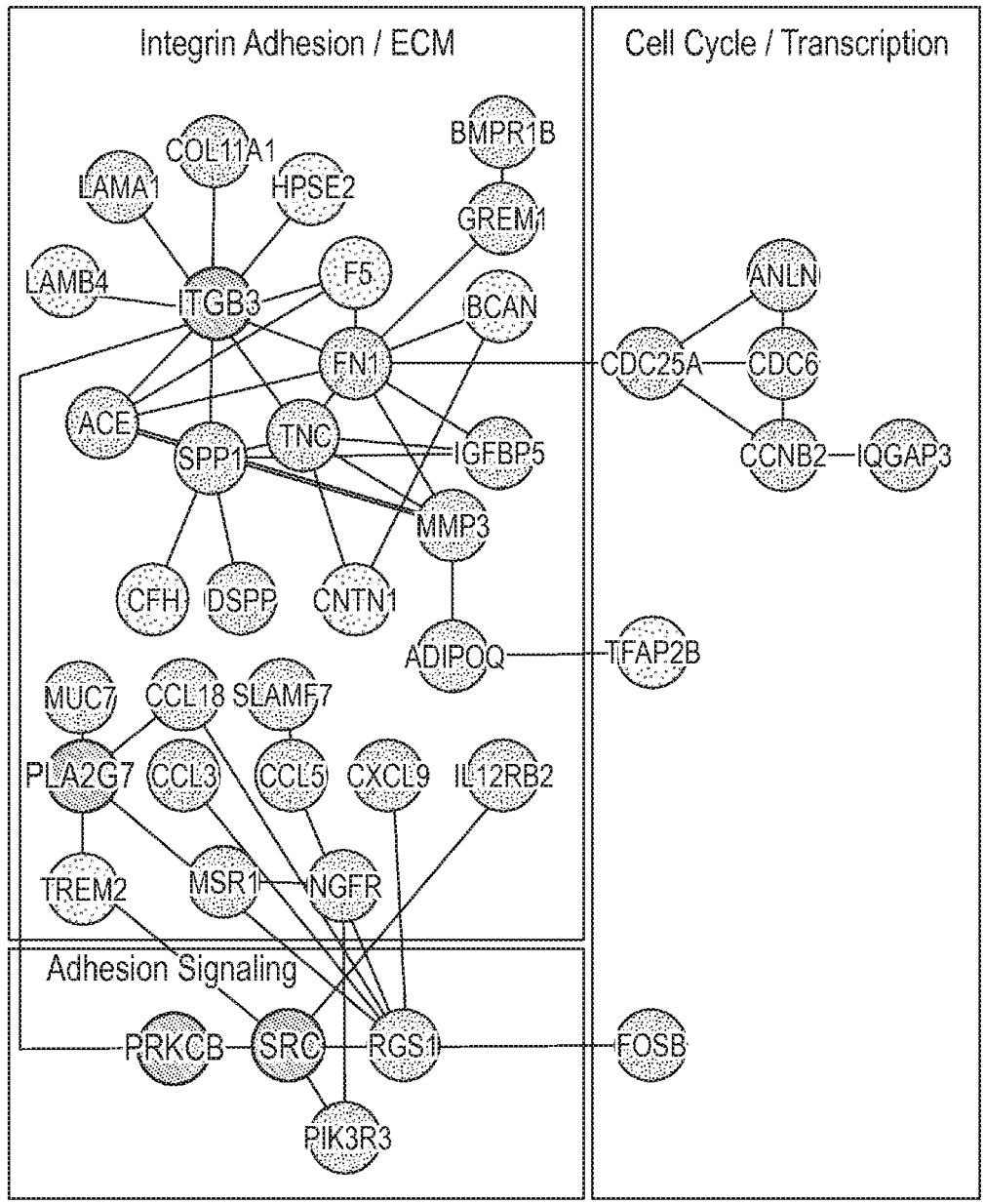
FIG. 17 shows integrin cell adhesion is a cellular system differentially expressed in metastatic melanoma vs. non-metastatic pigmented lesions. 164 of 16,029 genes were significantly regulated in benign nevi vs. regionally metastatic melanoma (FDR<0.01) as determined by next-generation sequencing (NGS). Functional relationships between these genes were mapped by the STRING database. Genes without known functional relationships to other genes (i.e., disconnected nodes) or networks with <3 genes were hidden. A large cluster emerged that was functionally related to integrin cell adhesion and the extracellular space (ECM). Additional NGS-based comparison of samples from patients with regional metastasis vs. non-metastatic melanoma revealed the deregulation of an ITGB3/protein kinase C/SRC network in regionally metastatic melanoma. The particularly indicated circles indicate gene up-regulation, regionally metastatic melanoma vs. nevi; blue circles indicate down-regulation, regionally metastatic melanoma vs. nevi. The particularly indicated rings indicate up-regulation, regionally metastatic vs. non-metastatic melanoma.

Expanding the sample size of the model validation cohort from 104 to 146 resulted in excellent discriminative ability of the clinicopathologic+molecular model with an AUC of 0.93, 95% CI 0.87-0.97 (FIG. 17). Using the suggested cutoff of 10% (Balch et al., *J Am. Acad. Dermatol.*, 60:872-875 (2009)), the false positive rate was 22%, and the false negative rate was 0%. These results demonstrate that data obtained by gene expressing profiling can be combined with Breslow depth, tumor ulceration, and patient age to calculate the predicted probability of SLN positivity at the time of primary diagnosis. These results also can be used to improve patient care by avoiding unnecessary SLN procedures.

Example 5—Identifying Inhibitors of Integrin Cell Adhesion Remodeling

Osteopontin (SPP1) is a proto-typical cancer-associated extracellular matrix gene and ligand of αv and α5β1 integrins. SPP1 is highly overexpressed in melanoma (Talantov et al., *Clin. Cancer Res.* 11:7234-42 (2005)) and its upregulation correlates with metastasis risk (Conway et al., *Clin.*

Figure 14:
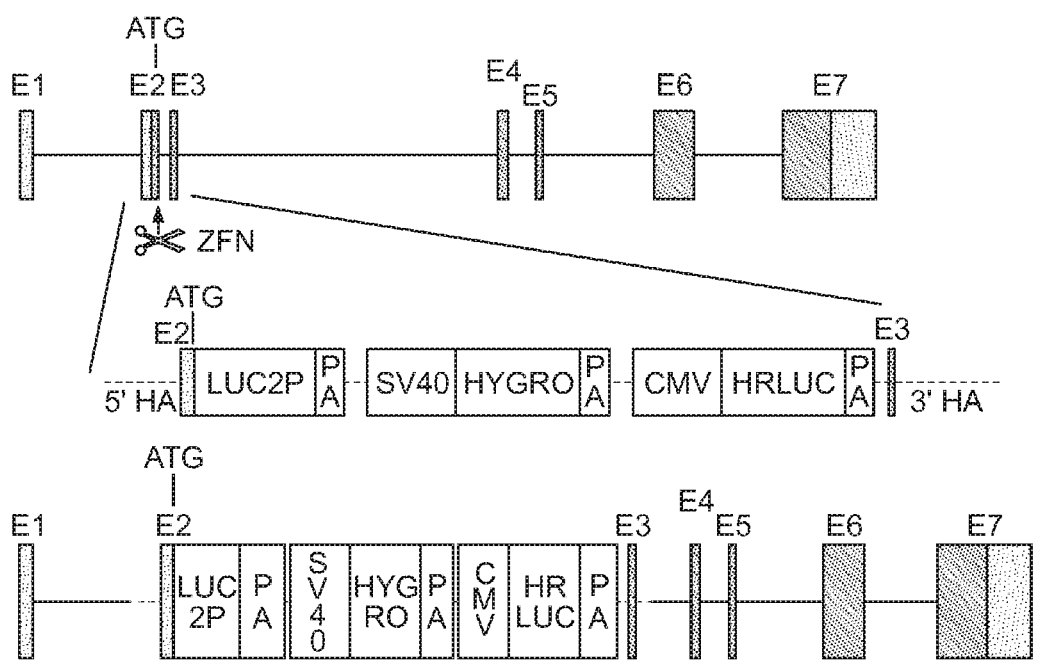
FIG. 14 depict the luciferase construct for high-throughput screening. Genomic structure of the SPP1 gene is shown as well as a targeting approach. A DNA double-strand break was induced in exon (E) 2 of SPP1, 3' of the ATG start codon by a custom-made zinc finger nuclease (ZFN), arrow. A targeting vector with 500 bp homology arms (HA, middle), Hygromycin resistance (HYGRO), a target promoter-driven firefly luciferase (LUC2P), and a CMV-pomoter driven renilla luciferase (HRLUC) was offered for repair at the time of the double-strand break. PA, PA terminator signal. Blue boxes, untranslated region; black boxes, translated region.

Cancer Res. 15:6939-6946 (2009) and Mitra et al., Br. J. Cancer 103:1229-1236 (2010)). To rapidly screen chemical compounds for their ability to inhibit SPP1 expression in vitro, the endogenous SPP1 promoter of WM858 melanoma cells was tagged with a dual luciferase system using zinc finger nucleases. The SPP1-promoter drives firefly luciferase tagged with a protein degradation sequence (hPEST). A CMV-promoter driven renilla luciferase was used as a loading control (FIG. 14). Assaying both luciferase signals was fast and amendable to high-throughput screening.

The investigation was started by screening a 1280 compound library of pharmaceutically active compounds (LOPAC; Sigma-Aldrich). The firefly signal was first normalized to the renilla signal, then to DMSO-treated control wells (FIG. 15A). Normalized ratios<0.25 were observed for a handful of compounds, including Pentamidine (FIG. 15B). Pentamidine is an FDA approved antimicrobial drug that is used in the prevention and treatment of Pneumocystis pneumonia. It appears to possess other activities as well. See, e.g., Pathak et al., Molecular Cancer Therapeutics, 1:1255-1264 (2002); Smith et al., Anti-Cancer Drugs, 21:181 (2010); and Sun and Zhang, Nucleic Acids Res., 36:1654-1664 (2008).

Figure 15F:
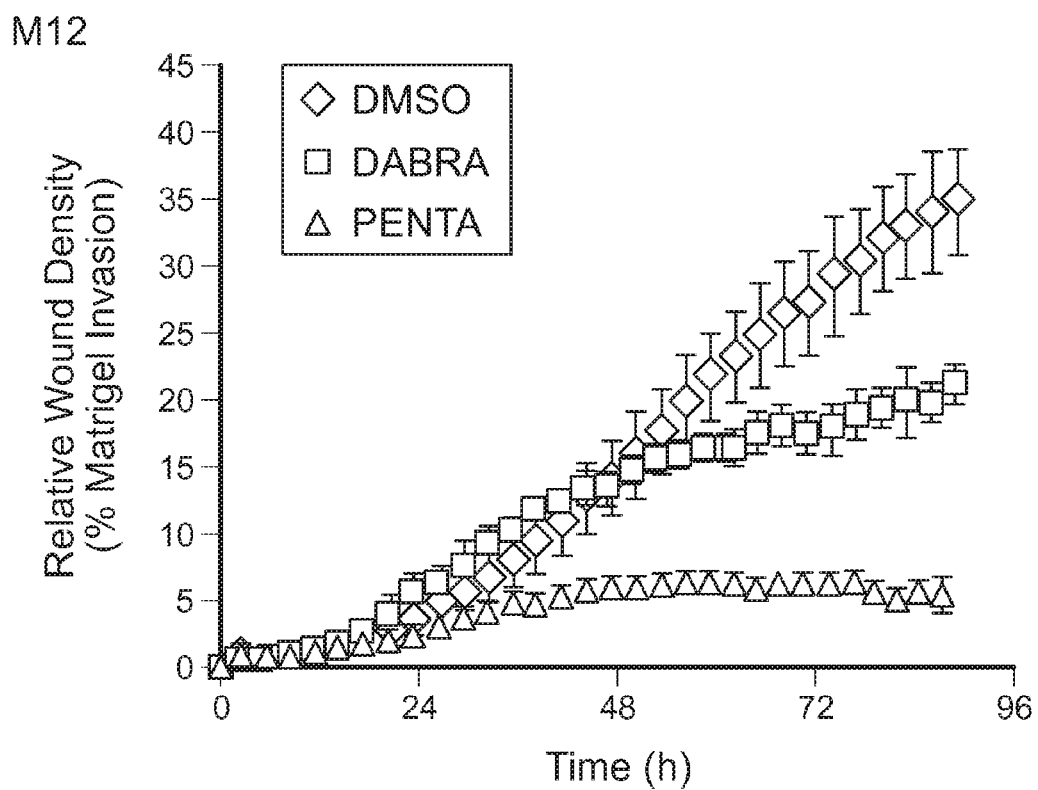
Figure 15G:
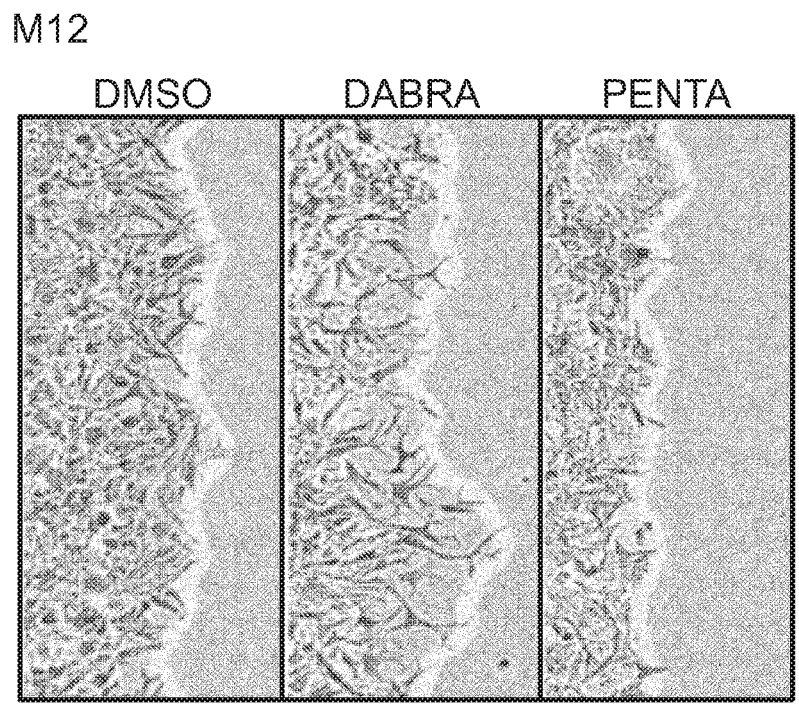

Pentamidine exhibited little cytotoxicity in WM858 and M12 cells with $ED_{50's}$>100 µM (M12 cells are metastatic B-raf$^V$600E melanoma cells that were recently established from a patient). Pentamidine inhibited SPP1 mRNA in both WM858 (FIG. 15C) and M12 cells (FIG. 15D). Pentamidine also reduced expression of β integrin and t-PA (PLAT) (FIG. 15E). Next, a red-fluorescent nuclear protein was stably expressed in M12 cells to automatically count nuclei over time (using the IncuCyte ZOOM system, Essen Bioscience), a surrogate measure of cell proliferation. Pentamidine reduced M12 proliferation with an $ED_{50}$ of 40 µM. When M12 cells were allowed to migrate into Matriger-embedded scratch wounds, Pentamidine inhibited Matrigel® invasion more effectively than Dabrafenib (FIGS. 15F and 15G).

Figure 15H:
Figure 15I:
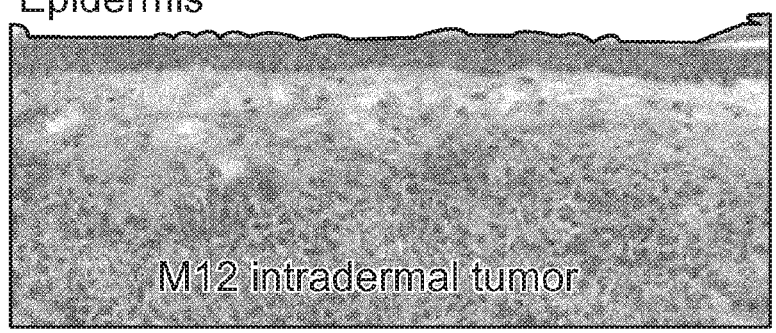
Figure 15J:
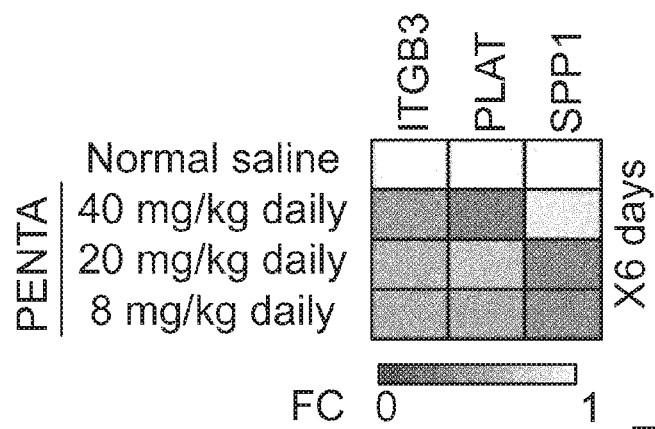

To determine whether Pentamidine reduces SPP1 expression in vivo, M12 cells were injected intradermally into female nude mice and left to grow until xenograft tumors formed (FIGS. 15H and 15I). Then, four different doses of Pentamidine were injected intramuscularly (i.m.) into groups of three mice for six consecutive days. It was previously shown that serum concentration in patients injected with 4 mg/kg Pentamidine i.m. daily (FDA labeling) range from 0.2-1.4 µg/mL (0.3-2.4 µM). In rats, slightly lower levels can be achieved using 10 mg/kg i.m. daily (0.1-0.4 µg/mL) (Bernard et al., J. Inf. Dis. 152:750-754 (1985) and Waalkes et al., Clin. Pharma. Therap. 11:505-512 (1969)). In the current study, at the highest Pentamidine dose (80 mg/kg/daily), all mice died. Mice survived at 40 mg/kg/day, but appeared sick. The other two doses, specifically the 8 mg/kg/day dose, were well tolerated. Tumors were subsequently harvested, lysed, and analyzed by quantitative PCR. All doses of Pentamidine led to a reduction of SPP1, β3 integrin, and t-PA (PLAT) mRNA expression in tumor tissue (FIG. 15J).

These results demonstrate that pentamidine can be used to reduce the expression of ITGB3, PLAT, and SPP1.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method for identifying whether a mammal's skin lesion is metastatic malignant and treating the skin lesion, wherein said method comprises:
   (a) measuring, within a test sample of the skin lesion taken from the mammal, the expression level of a marker gene selected from the group consisting of PLAT, ITGB3, LAMB1, and TP53 to obtain a measured expression level of said marker gene for said test sample;
   (b) identifying said test sample as containing a metastatic malignant skin lesion based, at least in part, on said value of said marker gene expression for said test sample;
   (c) measuring, within the test sample, the expression level of a keratinocyte marker gene to obtain a measured expression level of the keratinocyte marker gene for the test sample;
   (d) removing, from the measured expression level of the marker gene for the test sample, a level of expression attributable to keratinocytes present in the test sample using the measured expression level of the keratinocyte marker gene for the test sample and a keratinocyte correction factor to obtain a corrected value of the marker gene expression for the test sample;
   (e) identifying the test sample as containing a metastatic malignant skin lesion based, at least in part, on the corrected value of the marker gene expression for the test sample; and
   (f) administering pentamidine to the mammal to treat the skin lesion.

2. The method of claim 1, wherein said keratinocyte marker gene is K14.

3. The method of claim 1, wherein said marker gene is PLAT or ITGB3.

4. The method of claim 1, wherein the method further comprises
   (i) multiplying said measured expression level of said keratinocyte marker gene for said test sample by said keratinocyte correction factor to obtain a correction value; and
   (ii) subtracting said correction value from said measured expression level of said marker gene for said test sample to obtain said corrected value of marker gene expression for said test sample.

5. The method of claim 1, wherein said method comprises determining, within said test sample, the expression level of at least two marker genes selected from the group consisting of PLAT, ITGB3, LAMB1, and TP53 to obtain measured expression levels of said at least two marker genes for said test sample.

6. The method of claim 1, wherein said method comprises determining, within said test sample, the expression level of at least three marker genes selected from the group consisting of PLAT, ITGB3, LAMB1, and TP53 to obtain measured expression levels of said at least three marker genes for said test sample.

7. The method of claim 1, wherein said method comprises determining, within said test sample, the expression level of PLAT, ITGB3, LAMB1, and TP53 to obtain measured expression levels of said PLAT, ITGB3, LAMB1, and TP53 for said test sample.

8. The method of claim 1, wherein the marker gene is LAMB1 or TP53.

9. The method according to claim 1, wherein the pentamidine is administered in an amount of from about 0.01 mg/kg to about 4 mg/kg based upon the mammal's body mass.

* * * * *